US012686948B2

(12) United States Patent
Zhou

(10) Patent No.: US 12,686,948 B2
(45) Date of Patent: Jul. 21, 2026

(54) CONSTRUCTION METHOD AND APPLICATION OF ANTIGEN-SPECIFIC BINDING POLYPEPTIDE GENE DISPLAY VECTOR

(71) Applicant: DDBIO.CO, LTD., (SHANG HAI), Shanghai (CN)

(72) Inventor: Chen Zhou, Shanghai (CN)

(73) Assignee: DDBIO.CO, LTD., (SHANG HAI), Shanghai (CN)

( * ) Notice: Subject to any disclaimer, the term of this patent is extended or adjusted under 35 U.S.C. 154(b) by 936 days.

(21) Appl. No.: 17/914,650

(22) PCT Filed: Mar. 26, 2021

(86) PCT No.: PCT/CN2021/083246
§ 371 (c)(1),
(2) Date: Sep. 26, 2022

(87) PCT Pub. No.: WO2021/190629
PCT Pub. Date: Sep. 30, 2021

(65) Prior Publication Data
US 2023/0124855 A1 Apr. 20, 2023

(30) Foreign Application Priority Data
Mar. 27, 2020 (CN) .......................... 202010231148.1

(51) Int. Cl.
*C40B 30/04* (2006.01)
*C12N 15/10* (2006.01)

(52) U.S. Cl.
CPC .......... *C40B 30/04* (2013.01); *C12N 15/1037* (2013.01); *C07K 2317/55* (2013.01)

(58) Field of Classification Search
None
See application file for complete search history.

(56) References Cited

U.S. PATENT DOCUMENTS

| | | | |
|---|---|---|---|
| 8,685,896 B2 | 4/2014 | Enzelberger et al. | |
| 2012/0101000 A1 | 4/2012 | Zhou | |

FOREIGN PATENT DOCUMENTS

| | | |
|---|---|---|
| CN | 101210241 A | 7/2008 |
| WO | 2010059981 A2 | 5/2010 |
| WO | 2019231276 A1 | 12/2019 |

OTHER PUBLICATIONS

EP 21776379.6 Extended European Search Report dated Apr. 15, 2024.

(Continued)

*Primary Examiner* — Christian C Boesen
(74) *Attorney, Agent, or Firm* — Sughrue Mion, PLLC

(57) ABSTRACT

Disclosed in the present application is a method for constructing an antigen-specific binding polypeptide gene display vector. The method comprises processing by using a restriction endonuclease that specifically recognizes a restriction site to obtain four nucleic acid fragments having specific sticky ends, and then enabling the nucleic acid fragments to directionally ligate. Further disclosed in the present application are an antigen-specific binding polypeptide gene display vector produced according to the method and a bacterial library. The method described in the present application can be used for effectively screening antigen-specific antigen-binding polypeptides or fragments thereof.

10 Claims, 9 Drawing Sheets

Specification includes a Sequence Listing.

(56) References Cited

OTHER PUBLICATIONS

Zhou, I., et al., Four-way ligation for construction of a mammalian cell-based full-length antibody display library, Acta Biochimica Biophysica Sinica, vol. 43, No. 3, pp. 232-238, The Author, Jan. 21, 2011.

Search Report issued Nov. 25, 2025 in Chinese Patent Application No. 2021800241434.

PCT/CN2021/083246 International Search Report dated Jun. 4, 2021.

Zhou et al., "Simultaneous Expression of Displayed and Secreted Antibodies for Antibody Screen", PLOS ONE, vol. 8, Issue 11, Nov. 2013, pp. 1-6.

Communication issued Jan. 28, 2025 in Japanese application No. 2022-558484.

Solforosi L. et al., A phage display vector optimized for the generation of human antibody combinatorial libraries and the molecular cloning of monoclonal antibody fragments, New Microbiol, 2012, vol. 35, N. 3, pp. 289-294, see abstract.

Li T. et al., A nuetralization scFv antibody against IL-1b isolated from a NIPA-based bacterial display library, Curr Pharm Biotechnol, 2013, vol. 14, N. 6, pp. 571-581, see abstract.

RU 2022127693 Search Report dated Jul. 24, 2024. Translation provided.

SEQUENCE LISTING

<160> NUMBER OF SEQ ID NOS: 175

<210> SEQ ID NO 1
<211> LENGTH: 50
<212> TYPE: DNA
<213> ORGANISM: Artificial Sequence
<220> FEATURE:
<223> OTHER INFORMATION: DDB214

<400> SEQUENCE: 1
tccagacatc taatggcgtc tcagtggttc agctagcacc aagggcccat          50

<210> SEQ ID NO 2
<211> LENGTH: 50
<212> TYPE: DNA
<213> ORGANISM: Artificial Sequence
<220> FEATURE:
<223> OTHER INFORMATION: DDB215

<400> SEQUENCE: 2
accagtcttc tattggctga tgagacgtta tcatttaccc ggagacaggg          50

<210> SEQ ID NO 3
<211> LENGTH: 40
<212> TYPE: DNA
<213> ORGANISM: Artificial Sequence
<220> FEATURE:
<223> OTHER INFORMATION: DDB216

<400> SEQUENCE: 3
atggggccac aggggcctca gctagcacca agggcccatc          40

<210> SEQ ID NO 4
<211> LENGTH: 39
<212> TYPE: DNA
<213> ORGANISM: Artificial Sequence
<220> FEATURE:
<223> OTHER INFORMATION: DDB217

<400> SEQUENCE: 4
ttgggccgtg caggccttat catttacccg gagacaggg          39

-continued

```
<210> SEQ ID NO 5
<211> LENGTH: 657
<212> TYPE: DNA
<213> ORGANISM: Artificial Sequence
<220> FEATURE:
<223> OTHER INFORMATION: PD1-LC

<400> SEQUENCE: 5
gaaattgtgc tgacccagag ccctgccaca ctcagcctga gccctggaga gagggccacc      60
ctgtcctgca gagccagcaa gggcgtgagc accagcggct acagctacct gcactggtac     120
cagcagaagc ccggccaggc tcccagactg ctgatctacc tggcttctta tttagaaagc     180
ggcgtgcctg ctagattcag cggctccggc tccggcaccg actttaccct gaccatcagc     240
tccctggagc ccgaggactt cgccgtgtac tactgccagc acagcaggga cctgcccctg     300
acctttggcg gaggcaccaa ggtggagatc aagaggaccg tggccgctcc cagcgtgttc     360
atcttccccc ccagcgacga gcagctgaag agcggaaccg ccagcgtggt gtgcctgctg     420
aacaacttct accccaggga ggccaaggtg cagtggaagg tcgacaacgc cctgcagagc     480
ggcaatagcc aggagtccgt gaccgagcag gacagcaagg acagcaccta cagcctgagc     540
agcaccctca ccctgtccaa ggccgactac gagaagcata aggtgtacgc ctgtgaggtg     600
acccaccagg gcctgtccag ccctgtgacc aaaagcttta ccgcggcga atgctga        657

<210> SEQ ID NO 6
<211> LENGTH: 360
<212> TYPE: DNA
<213> ORGANISM: Artificial Sequence
<220> FEATURE:
<223> OTHER INFORMATION: PD1-VH

<400> SEQUENCE: 6
caggtgcagc tggtgcagag cggcgtggag gtgaaaaagc ccggcgccag cgtgaaggtg      60
tcctgtaagg cctccggcta cacattcacc aactactaca tgtactgggt gaggcaagcc     120
cctggccagg gactggaatg gatgggcgga atcaaccccct ccaatggagg caccaacttt     180
aacgagaagt tcaagaacag ggtgacactg acaaccgaca gcagcacaac aaccgcttac     240
atggagctga gagcctgca gttcgatgac accgccgtgt actactgcgc caggagggac     300
tacaggttcg acatgggctt tgattactgg ggccagggca ccaccgtgac cgtctcatca     360

<210> SEQ ID NO 7
<211> LENGTH: 9109
<212> TYPE: DNA
<213> ORGANISM: Artificial Sequence
<220> FEATURE:
<223> OTHER INFORMATION: pDGB4

<400> SEQUENCE: 7
tctggctaac tagagaaccc actgcttact ggcttatcga aattaatacg actcactata      60
gggagaccca agctggctag gccacatagg cctgaaccac catggtgttg cagacccagg     120
tcttcatttc tctgttgctc tggatctctg tgattacagg tgccgacggg gacatcgtga     180
tgacccagtc tccagactcc ctggctgtgt ctctgggcga gagggccacc atcaactgca     240
agtccagcca gagtgtttta tacagcccca caatgagaa cttcttagct tggtaccaac     300
agaagccagg acagtctcct aagttgctca tttactgggc gtctacccgg gaatccgggg     360
tccctgaccg attcagtggc agcgggtctg ggacagattt cactctcacc atcagcaacc     420
```

-continued

```
tgcaggctga agatgtggca gtttactact gtcaacaata ttatagtgct cctatcactt    480
tcggcggagg gaccaaggtg gagatcaaac gaactgtggc tgcaccatct gtcttcatct    540
tcccgccatc tgatgagcag ttgaaatctg gaactgcctc tgttgtgtgc ctgctgaata    600
acttctatcc cagagaggcc aaagtacagt ggaaggtgga taacgccctc caatcgggta    660
actcccagga gagtgtcaca gagcaggaca gcaaggacag cacctacagc ctcagcagca    720
ccctgacgct gagcaaagca gactacgaga aacacaaact ctacgcctgc gaagtcaccc    780
atcagggcct gagctcgccc gtcacaaaga gcttcaacag gggagagtct tgataaggcc    840
tgcacggccc tcgagtctag agggcccgtt taaacccgct gatcagcctc gactgtgcct    900
tctagttgcc agccatctgt tgtttgcccc tcccccgtgc cttccttgac cctggaaggt    960
gccactccca ctgtcctttc ctaataaaat gaggaaattg catcgcattg tctgagtagg   1020
tgtcattcta ttctgggggg tggggtgggg caggacagca aggggagga ttgggaagac    1080 aatagcaggc atgctgggga tgcggtgggc tctatggctt ctgaggcgga aagaaccagc   1140
tggggctcta gggggtatcc ccacgcgccc tgtagcggcg cattaagcgc ggcgggtgtg   1200
gtggttacgc gcagcgtgac cgctacactt gccagcgccc tagcgcccgc tcctttcgct   1260
ttcttccctt cctttctcgc cacgttcgcc ggctttcccc gtcaagctct aaatcggggg   1320 ctcccttttag ggttccgatt tagtgcttta cggcacctcg accccaaaaa acttgattag   1380
ggtgatggtt cacgtaccta gaagttccta ttccgaagtt cctattctct agaaagtata   1440
ggaacttcct tggccaaaaa gcctgaactc accgcgacgt ctgtcgagaa gtttctgatc   1500
gaaaagttcg acagcgtgtc cgacctgatg cagctctcgg agggcgaaga tctcgtgct   1560 ttcagcttcg atgtaggagg gcgtggatat gtcctgcggg taaatagctg cgccgatggt   1620
ttctacaaag atcgttatgt ttatcggcac tttgcatcgg ccgcgctccc gattccggaa   1680
gtgcttgaca ttggggaatt cagcgagagc ctgacctatt gcatctcccg ccgtgcacag   1740
ggtgtcacgt tgcaagacct gcctgaaacc gaactgcccg ctgttctgca gccggtcgcg   1800
gaggccatgg atgcgatcgc tgcggccgat cttagccaga cgagcgggtt cggcccattc   1860
ggaccgcaag gaatcggtca atacactaca tggcgtgatt tcatatgcgc gattgctgat   1920
ccccatgtgt atcactggca aactgtgatg gacgacaccg tcagtgcgtc cgtcgcgcag   1980
gctctcgatg agctgatgct ttgggccgag gactgccccg aagtccggca cctcgtgcac   2040
gcggatttcg gctccaacaa tgtcctgacg gacaatggcc gcataacagc ggtcattgac   2100
tggagcgagg cgatgttcgg ggattcccaa tacgaggtcg ccaacatctt cttctggagg   2160
ccgtggttgg cttgtatgga gcagcagacg cgctacttcg agcggaggca tccggagctt   2220
gcaggatcgc cgcggctccg gcgtatatg ctccgcattg gtcttgacca actctatcag   2280
agcttggttg acggcaattt cgatgatgca gcttgggcgc agggtcgatg cgacgcaatc   2340
gtccgatccg gagccgggac tgtcgggcgt acacaaatcg cccgcagaag cgcggccgtc   2400
tggaccgatg ctgtgtaga agtactcgcc gatagtggaa accgacgccc cagcactcgt   2460
ccgagggcaa aggaatagca cgtactacga gatttcgatt ccaccgccgc cttctatgaa   2520
aggttgggct tcggaatcgt tttccgggac gccggctgga tgatcctcca gcgcggggat   2580
ctcatgctgg agttcttcgc ccaccccaac ttgtttattg cagcttataa tggttacaaa   2640
taaagcaata gcatcacaaa tttcacaaat aaagcatttt tttcactgca ttctagttgt   2700
ggtttgtcca aactcatcaa tgtatcttat catgtctgta taccgtcgac ctctagctag   2760
agcttggcgt aatcatggtc atagctgttt cctgtgtgaa attgttatcc gctcacaatt   2820
```

-continued

```
ccacacaaca tacgagccgg aagcataaag tgtaaagcct ggggtgccta atgagtgagc   2880
taactcacat taattgcgtt gcgctcactg cccgctttcc agtcgggaaa cctgtcgtgc   2940
cagctgcatt aatgaatcgg ccaacgcgcg gggagaggcg gtttgcgtat tgggcgctct   3000
tccgcttcct cgctcactga ctcgctgcgc tcggtcgttc ggctgcggcg agcggtatca   3060
gctcactcaa aggcggtaat acggttatcc acagaatcag gggataacgc aggaaagaac   3120
atgtgagcaa aaggccagca aaaggccagg aaccgtaaaa aggccgcgtt gctggcgttt   3180
ttccataggc tccgcccccc tgacgagcat cacaaaaatc gacgctcaag tcagaggtgg   3240
cgaaacccga caggactata aagataccag gcgtttcccc ctggaagctc cctcgtgcgc   3300
tctcctgttc cgaccctgcc gcttaccgga tacctgtccg cctttctccc ttcgggaagc   3360
gtggcgcttt ctcatagctc acgctgtagg tatctcagtt cggtgtaggt cgttcgctcc   3420
aagctgggct gtgtgcacga acccccgtt cagcccgacc gctgcgcctt atccggtaac   3480
tatcgtcttg agtccaaccc ggtaagacac gacttatcgc cactggcagc agccactggt   3540
aacaggatta gcagagcgag gtatgtaggc ggtgctacag agttcttgaa gtggtggcct   3600
aactacggct acactagaag aacagtattt ggtatctgcg ctctgctgaa gccagttacc   3660
ttcggaaaaa gagttggtag ctcttgatcc ggcaaacaaa ccaccgctgg tagcggtggt   3720 tttttgttt gcaagcagca gattacgcgc agaaaaaaag gatctcaaga agatcctttg   3780
atcttttcta cggggtctga cgctcagtgg aacgaaaact cacgttaagg gattttggtc   3840
atgagattat caaaaaggat cttcacctag atccttttaa attaaaaatg aagttttaaa   3900
tcaatctaaa gtatatatga gtaaacttgg tctgacagtt accaatgctt aatcagtgag   3960
gcacctatct cagcgatctg tctatttcgt tcatccatag ttgcctgact ccccgtcgtg   4020
tagataacta cgatacggga gggcttacca tctggcccca gtgctgcaat gataccgcga   4080
gacccacgct caccggctcc agatttatca gcaataaacc agccagccgg aagggccgag   4140
cgcagaagtg gtcctgcaac tttatccgcc tccatccagt ctattaattg ttgccgggaa   4200
gctagagtaa gtagttcgcc agttaatagt ttgcgcaacg ttgttgccat tgctacaggc   4260
atcgtggtgt cacgctcgtc gtttggtatg gcttcattca gctccggttc ccaacgatca   4320
aggcgagtta catgatcccc catgttgtgc aaaaaagcgg ttagctcctt cggtcctccg   4380
atcgttgtca gaagtaagtt ggccgcagtg ttatcactca tggttatggc agcactgcat   4440
aattctctta ctgtcatgcc atccgtaaga tgcttttctg tgactggtga gtactcaacc   4500
aagtcattct gagaatagtg tatgcggcga ccgagttgct cttgcccggc gtcaatacgg   4560
gataataccg cgccacatag cagaacttta aaagtgctca tcattggaaa acgttcttcg   4620
gggcgaaaac tctcaaggat cttaccgctg ttgagatcca gttcgatgta acccactcgt   4680
gcacccaact gatcttcagc atcttttact ttcaccagcg tttctgggtg agcaaaaaca   4740
ggaaggcaaa atgccgcaaa aaagggaata agggcgacac ggaaatgttg aatactcata   4800
ctcttccttt ttcaatatta ttgaagcatt tatcagggtt attgtctcat gagcggatac   4860
atatttgaat gtatttagaa aaataaacaa ataggggttc cgcgcacatt tccccgaaaa   4920
gtgccacctg acgtcgacgg atcgggagat ctcccgatcc cctatggtgc actctcagta   4980
caatctgctc tgatgccgca tagttaagcc agtatctgct ccctgcttgt gtgttggagg   5040
tcgctgagta gtgcgcgagc aaaatttaag ctacaacaag caaggcttg accgacaatt   5100 gcatgaagaa tctgcttagg gttaggcgtt ttgcgctgct tcgcgatgta cgggccagat   5160
```

-continued

```
atacgcgttg acattgatta ttgactagtt attaatagta atcaattacg gggtcattag      5220
ttcatagccc atatatggag ttccgcgtta cataacttac ggtaaatggc ccgcctggct      5280
gaccgcccaa cgacccccgc ccattgacgt caataatgac gtatgttccc atagtaacgc      5340
caatagggac tttccattga cgtcaatggg tggagtattt acggtaaact gcccacttgg      5400
cagtacatca agtgtatcat atgccaagta cgccccctat tgacgtcaat gacggtaaat      5460
ggcccgcctg gcattatgcc cagtacatga ccttatggga ctttcctact tggcagtaca      5520
tctacgtatt agtcatcgct attaccatgg tgatgcggtt ttggcagtac atcaatgggc      5580
gtggatagcg gtttgactca cggggatttc caagtctcca ccccattgac gtcaatggga      5640
gtttgttttg gcaccaaaat caacgggact ttccaaaatg tcgtaacaac tccgccccat      5700
tgacgcaaat gggcggtagg cgtgtacggt gggaggtcta tataagcaga gctctctggc      5760
taactagaga acccactgct tactggctta tcgaaattaa tacgactcac tatagggaga      5820
gggagaccca agctggctag ccacctgatt ggcgtctcta gtccaccatg gactttgggc      5880
tgagctggct ttttcttgtg gctattttaa aaggtgtcca gtgtgaggtg cagctgttgg      5940
agtctggggg aggcttggta cagcctgggg ggtccctgag actcctctgt gcagcctctg      6000
gattcacctt tagcagctat gccatgagct gggtccgcca ggctccaggg aaggggctgg      6060
agtgggtctc aggtattact gggagtggtg gtagtacata ctacgcagac tccgtgaagg      6120
gccggttcac catctccaga gacaattcca agaacacgct gtatctgcaa atgaacagcc      6180
tgagagccga ggacacggcc gtatattact gtgcgaaaga tccagggact acggtgatta      6240
tgagttggtt cgacccctgg ggccagggaa ccctggtcac cgtctcctca gctagcacca      6300
agggcccatc ggtcttcccc ctggcgccct gctccaggag cacctccgag agcacagcgg      6360
ccctgggctg cctggtcaag gactacttcc ccgaaccggt gacggtgtcg tggaactcag      6420
gcgctctgac cagcggcgtg cacaccttcc cagctgtcct acagtcctca ggactctact      6480
ccctcagcag cgtggtgacc gtgccctcca gcaacttcgg cacccagacc tacacctgca      6540
acgtagatca caagcccagc aacaccaagg tggacaagac agttgagcgc aaatgttgtg      6600
tcgagtgccc accgtgccca gcaccacctg tggcaggacc gtcagtcttc ctcttccccc      6660
caaaacccaa ggacaccctc atgatctccc ggacccctga ggtcacgtgc gtggtggtgg      6720
acgtgagcca cgaagacccc gaggtccagt tcaactggta cgtggacggc gtggaggtgc      6780
ataatgccaa gacaaagcca cgggaggagc agttcaacag cacgttccgt gtggtcagcg      6840
tcctcaccgt tgtgcaccag gactggctga acggcaagga gtacaagtgc aaggtctcca      6900
acaaaggcct cccagccccc atcgagaaaa ccatctccaa aaccaaaggg cagccccgag      6960
aaccacaggt gtacaccctg cccccatccc gggaggagat gaccaagaac caggtcagcc      7020
tgacctgcct ggtcaaaggc ttctacccca gcgacatcgc cgtggagtgg gagagcaatg      7080
ggcagccgga gaacaactac aagaccacac ctcccatgct ggactccgac ggctccttct      7140
tcctctacag caagctcacc gtggacaaga gcaggtggca gcaggggaac gtcttctcat      7200
gctccgtgat gcatgaggct ctgcacaacc actacacgca gaagagcctc tccctgtctc      7260
cgggtaaaaa tgctgtgggc caggacacgc aggaggtcat cgtggtgcca cactccttgc      7320
cctttaaggt ggtggtgatc tcagccatcc tggccctggt ggtgctcacc atcatctccc      7380
ttatcatcct catcatgctt tggcagaaga gccacgttg ataaccatga ctctggacca      7440
tgggaaatgt cagagtggag aaccacaccg agtgccactg cagcacttgt tattatcaca      7500
aatcctaata gtttgcagtg ggccttgctg atgatggctg acttgctcaa aaggaaaatt      7560
```

```
aatttgtcca gtgtctatgg ctttgtgaga taaaaccctc cttttccttg ccataccatt    7620
tttaacctgc tttgagaata tactgcagct ttattgcttt tctccttatc ctacaatata    7680
atcagtagtc ttgatctttt catttggaat gaaatatggc atttagcatg accataaaaa    7740
gctgattcca ctggaaataa agtcttttaa atcatcactc tatcactgaa ttctaatttt    7800
ttctgaaaag tttcaagcca gttacttttg ataggattaa cggaagggag tgagccagtg    7860
ggtgaggtgg gttcccatgt agtcaatggc ctaatactgg agaatcttat tctaaccaag    7920
ccttccagag caagctgtga gcccctcaga cagtgggcta ctcatgagac agtccattgg    7980
ggtaaaggaa gaaatataa cttctatttc tattcatttg cacattgtct ttagatgccc    8040
atttgggtga gttttataga agtacagcta cattaaaaaa tagaactgat aatagataag    8100
gctttaaaaa aacttcattc atcaccagtt tgtcaagatt ccatttcaaa gtgaaaaacc    8160
aatttctaac gggttggtaa acacagcaga tggcagggtg aaaaattaaa gtgagtgcat    8220
gtacctttaa agaaacactg aaatgcacac acattactta acctgctcat tcatttattt    8280
acatatagtc ttgggtgtac aaaatttaga aataaataca tagatctccc gatcccctat    8340
ggtgcactct cagtacaatc tgctctgatg ccgcatagtt aagccagtat ctgctccctg    8400
cttgtgtgtt ggagcaaaat ttaagctaca acaaggcaag gcttgaccga caattgcatg    8460
aagaatctgc ttagggttag gcgttttgcg ctgcttcgcg atgtacgggc cagatatacg    8520
cgttgacatt gattattgac tagttattaa tagtaatcaa ttacggggtc attagttcat    8580
agcccatata tggagttccg cgttacataa cttacggtaa atggcccgcc tggctgaccg    8640
cccaacgacc cccgcccatt gacgtcaata atgacgtatg ttcccatagt aacgccaata    8700
gggactttcc attgacgtca atgggtggag tatttacggt aaactgccca cttggcagta    8760
catcaagtgt atcatatgcc aagtacgccc cctattgacg tcaatgacgg taaatggccc    8820
gcctggcatt atgcccagta catgacctta tgggactttc ctacttggca gtacatctac    8880
gtattagtca tcgctattac catggtgatg cggttttggc agtacatcaa tgggcgtgga    8940
tagcggtttg actcacgggg atttccaagt ctccacccca ttgacgtcaa tgggagtttg    9000
ttttggcacc aaaatcaacg ggactttcca aaatgtcgta acaactccgc cccattgacg    9060
caaatgggcg gtaggcgtgt acggtgggag gtctatataa gcagagctc                9109
```

```
<210> SEQ ID NO 8
<211> LENGTH: 12
<212> TYPE: DNA
<213> ORGANISM: Artificial Sequence
<220> FEATURE:
<223> OTHER INFORMATION: B2

<400> SEQUENCE: 8
cgtctcagtg gt                                                         12

<210> SEQ ID NO 9
<211> LENGTH: 12
<212> TYPE: DNA
<213> ORGANISM: Artificial Sequence
<220> FEATURE:
<223> OTHER INFORMATION: B3

<400> SEQUENCE: 9
cgtctcatca gc                                                         12

<210> SEQ ID NO 10
```

```
<211> LENGTH: 13
<212> TYPE: DNA
<213> ORGANISM: Artificial Sequence
<220> FEATURE:
<223> OTHER INFORMATION: S5

<400> SEQUENCE: 10
ggccacaggg gcc                                                      13

<210> SEQ ID NO 11
<211> LENGTH: 13
<212> TYPE: DNA
<213> ORGANISM: Artificial Sequence
<220> FEATURE:
<223> OTHER INFORMATION: S6

<400> SEQUENCE: 11
ggcctgcacg gcc                                                      13

<210> SEQ ID NO 12
<211> LENGTH: 57
<212> TYPE: DNA
<213> ORGANISM: Artificial Sequence
<220> FEATURE:
<223> OTHER INFORMATION: SP1

<400> SEQUENCE: 12
atgccctggg ctctgctcct cctgaccctc ctcactcact ctgccgtctc agtggtc    57

<210> SEQ ID NO 13
<211> LENGTH: 19
<212> TYPE: PRT
<213> ORGANISM: Artificial Sequence
<220> FEATURE:
<223> OTHER INFORMATION: SP1

<400> SEQUENCE: 13

Met Pro Trp Ala Leu Leu Leu Leu Thr Leu Leu Thr His Ser Ala Val
1               5                   10                  15

Ser Val Val

<210> SEQ ID NO 14
<211> LENGTH: 57
<212> TYPE: DNA
<213> ORGANISM: Artificial Sequence
<220> FEATURE:
<223> OTHER INFORMATION: SP2

<400> SEQUENCE: 14
atggactgga cctggaggat cctcttcttg gtggcagcgg ccacaggggc ccactcc    57

<210> SEQ ID NO 15
<211> LENGTH: 19
<212> TYPE: PRT
<213> ORGANISM: Artificial Sequence
<220> FEATURE:
<223> OTHER INFORMATION: SP2

<400> SEQUENCE: 15

Met Asp Trp Thr Trp Arg Ile Leu Phe Leu Val Ala Ala Ala Thr Gly
1               5                   10                  15

Ala His Ser

<210> SEQ ID NO 16
<211> LENGTH: 37
```

```
<212> TYPE: DNA
<213> ORGANISM: Artificial Sequence
<220> FEATURE:
<223> OTHER INFORMATION: P1

<400> SEQUENCE: 16
aaggcctgca cggccctcga gtctagaggg cccgttt                              37

<210> SEQ ID NO 17
<211> LENGTH: 86
<212> TYPE: DNA
<213> ORGANISM: Artificial Sequence
<220> FEATURE:
<223> OTHER INFORMATION: P2

<400> SEQUENCE: 17
gggagaccca agctggctag tagtccacca tgccctgggc tctgctcctc ctgaccctcc     60
tcactcactc tgccgtctca gtggtc                                         86

<210> SEQ ID NO 18
<211> LENGTH: 43
<212> TYPE: DNA
<213> ORGANISM: Artificial Sequence
<220> FEATURE:
<223> OTHER INFORMATION: P3

<400> SEQUENCE: 18
caccgtgacc gtctcatcag ctagcaccaa gggcccatcg gtc                       43

<210> SEQ ID NO 19
<211> LENGTH: 83
<212> TYPE: DNA
<213> ORGANISM: Artificial Sequence
<220> FEATURE:
<223> OTHER INFORMATION: P4

<400> SEQUENCE: 19
tgggcccctg tggccgctgc caccaagaag aggatcctcc aggtccagtc catggtggtt     60
catagccagc ttgggtctcc cta                                            83

<210> SEQ ID NO 20
<211> LENGTH: 49
<212> TYPE: DNA
<213> ORGANISM: Artificial Sequence
<220> FEATURE:
<223> OTHER INFORMATION: P5

<400> SEQUENCE: 20
tggcagcggc cacaggggcc cactccgaaa ttgtgctgac ccagagccc                 49

<210> SEQ ID NO 21
<211> LENGTH: 54
<212> TYPE: DNA
<213> ORGANISM: Artificial Sequence
<220> FEATURE:
<223> OTHER INFORMATION: P6

<400> SEQUENCE: 21
tagactcgag ggccgtgcag gccttatcag cattcgccgc ggttaaagct tttg           54

<210> SEQ ID NO 22
<211> LENGTH: 45
<212> TYPE: DNA
<213> ORGANISM: Artificial Sequence
<220> FEATURE:
```

-continued

```
<223> OTHER INFORMATION: P7

<400> SEQUENCE: 22
ctcactctgc cgtctcagtg gtccaggtgc agctggtgca gagcg                     45

<210> SEQ ID NO 23
<211> LENGTH: 42
<212> TYPE: DNA
<213> ORGANISM: Artificial Sequence
<220> FEATURE:
<223> OTHER INFORMATION: P8

<400> SEQUENCE: 23
ccttggtgct agctgatgag acggtcacgg tggtgccctg gc                        42

<210> SEQ ID NO 24
<211> LENGTH: 21
<212> TYPE: DNA
<213> ORGANISM: Artificial Sequence
<220> FEATURE:
<223> OTHER INFORMATION: VH fragment forward primer

<400> SEQUENCE: 24
tgggctctgc tcctcctgac c                                               21

<210> SEQ ID NO 25
<211> LENGTH: 25
<212> TYPE: DNA
<213> ORGANISM: Artificial Sequence
<220> FEATURE:
<223> OTHER INFORMATION: VH fragment reverse primer

<400> SEQUENCE: 25
agttccacga caccgtcacc ggttc                                           25

<210> SEQ ID NO 26
<211> LENGTH: 24
<212> TYPE: DNA
<213> ORGANISM: Artificial Sequence
<220> FEATURE:
<223> OTHER INFORMATION: LC fragment forward primers

<400> SEQUENCE: 26
ggacctggag gatcctcttc ttgg                                            24

<210> SEQ ID NO 27
<211> LENGTH: 52
<212> TYPE: DNA
<213> ORGANISM: Artificial Sequence
<220> FEATURE:
<223> OTHER INFORMATION: LC fragment reverse primer

<400> SEQUENCE: 27
taaattcctc ggccgtgcag gccttatcaa cactctcccc tgttgaagct ct            52

<210> SEQ ID NO 28
<211> LENGTH: 122
<212> TYPE: PRT
<213> ORGANISM: Artificial Sequence
<220> FEATURE:
<223> OTHER INFORMATION: Antigen-binding peptide VH

<400> SEQUENCE: 28

Gln Met Gln Leu Val Gln Ser Gly Pro Gly Leu Val Lys Pro Ser Gly
1               5                   10                  15
```

```
Thr Leu Ser Leu Thr Cys Ala Val Ser Gly Gly Ser Ile Ser Gly Ser
            20                  25                  30

Asn Trp Trp Ser Trp Val Arg Gln Pro Pro Gly Lys Gly Leu Glu Trp
        35                  40                  45

Ile Gly Glu Ile Phe His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Asn Leu Asn Ser Val Thr Ala Ala Asp Thr Ala Val Tyr Tyr Cys
                85                  90                  95

Ala Lys Asp Arg Gly Gly Tyr Tyr Asp Ser Ser Gly Tyr Ser His Trp
            100                 105                 110

Gly Gln Gly Thr Met Val Thr Val Ser Ser
            115                 120
```

<210> SEQ ID NO 29
<211> LENGTH: 214
<212> TYPE: PRT
<213> ORGANISM: Artificial Sequence
<220> FEATURE:
<223> OTHER INFORMATION: Antigen-binding peptide KLC

<400> SEQUENCE: 29

```
Asp Ile Val Met Thr Gln Ser Pro Ser Ser Val Ser Ala Ser Val Gly
1               5                   10                  15

Gly Arg Val Thr Ile Thr Cys Arg Ala Ser Gln Gly Ile Ser Ser Trp
            20                  25                  30

Leu Ala Trp Tyr Gln Gln Lys Pro Gly Arg Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Ile
                85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210
```

<210> SEQ ID NO 30
<211> LENGTH: 45
<212> TYPE: DNA
<213> ORGANISM: Artificial Sequence
<220> FEATURE:

<223> OTHER INFORMATION: 1st VH forward primer

<400> SEQUENCE: 30
ctcactctgc cgtctcagtg gtcgaggtgc agctggtgga gtctg                           45

<210> SEQ ID NO 31
<211> LENGTH: 45
<212> TYPE: DNA
<213> ORGANISM: Artificial Sequence
<220> FEATURE:
<223> OTHER INFORMATION: 2nd VH forward primer

<400> SEQUENCE: 31
ctcactctgc cgtctcagtg gtccaggtgc agctgcagga gtcgg                           45

<210> SEQ ID NO 32
<211> LENGTH: 45
<212> TYPE: DNA
<213> ORGANISM: Artificial Sequence
<220> FEATURE:
<223> OTHER INFORMATION: 3rd VH forward primer

<400> SEQUENCE: 32
ctcactctgc cgtctcagtg gtccaggtgc agctggtgca gtctg                           45

<210> SEQ ID NO 33
<211> LENGTH: 45
<212> TYPE: DNA
<213> ORGANISM: Artificial Sequence
<220> FEATURE:
<223> OTHER INFORMATION: 4th VH forward primer

<400> SEQUENCE: 33
ctcactctgc cgtctcagtg gtccaggtgc agctggtgga gtctg                           45

<210> SEQ ID NO 34
<211> LENGTH: 46
<212> TYPE: DNA
<213> ORGANISM: Artificial Sequence
<220> FEATURE:
<223> OTHER INFORMATION: 5th VH forward primer

<400> SEQUENCE: 34
ctcactctgc cgtctcagtg gtccaggtca ccttgaagga gtctgg                          46

<210> SEQ ID NO 35
<211> LENGTH: 46
<212> TYPE: DNA
<213> ORGANISM: Artificial Sequence
<220> FEATURE:
<223> OTHER INFORMATION: 6th VH forward primer

<400> SEQUENCE: 35
ctcactctgc cgtctcagtg gtcgaagtgc agctggtgga gtctgg                          46

<210> SEQ ID NO 36
<211> LENGTH: 46
<212> TYPE: DNA
<213> ORGANISM: Artificial Sequence
<220> FEATURE:
<223> OTHER INFORMATION: 7th VH forward primer

<400> SEQUENCE: 36
ctcactctgc cgtctcagtg gtccaggtcc agcttgtgca gtctgg                          46

```
<210> SEQ ID NO 37
<211> LENGTH: 46
<212> TYPE: DNA
<213> ORGANISM: Artificial Sequence
<220> FEATURE:
<223> OTHER INFORMATION: 8th VH forward primer

<400> SEQUENCE: 37
ctcactctgc cgtctcagtg gtccaggttc agctggtgca gtctgg                   46

<210> SEQ ID NO 38
<211> LENGTH: 46
<212> TYPE: DNA
<213> ORGANISM: Artificial Sequence
<220> FEATURE:
<223> OTHER INFORMATION: 9th VH forward primer

<400> SEQUENCE: 38
ctcactctgc cgtctcagtg gtccaggtcc agctggtaca gtctgg                   46

<210> SEQ ID NO 39
<211> LENGTH: 46
<212> TYPE: DNA
<213> ORGANISM: Artificial Sequence
<220> FEATURE:
<223> OTHER INFORMATION: 10th VH forward primer

<400> SEQUENCE: 39
ctcactctgc cgtctcagtg gtccagatgc agctggtgca gtctgg                   46

<210> SEQ ID NO 40
<211> LENGTH: 46
<212> TYPE: DNA
<213> ORGANISM: Artificial Sequence
<220> FEATURE:
<223> OTHER INFORMATION: 11th VH forward primer

<400> SEQUENCE: 40
ctcactctgc cgtctcagtg gtccaaatgc agctggtgca gtctgg                   46

<210> SEQ ID NO 41
<211> LENGTH: 46
<212> TYPE: DNA
<213> ORGANISM: Artificial Sequence
<220> FEATURE:
<223> OTHER INFORMATION: 12th VH forward primer

<400> SEQUENCE: 41
ctcactctgc cgtctcagtg gtcgaggtcc agctggtaca gtctgg                   46

<210> SEQ ID NO 42
<211> LENGTH: 46
<212> TYPE: DNA
<213> ORGANISM: Artificial Sequence
<220> FEATURE:
<223> OTHER INFORMATION: 13th VH forward primer

<400> SEQUENCE: 42
ctcactctgc cgtctcagtg gtccagatca ccttgaagga gtctgg                   46

<210> SEQ ID NO 43
<211> LENGTH: 46
<212> TYPE: DNA
<213> ORGANISM: Artificial Sequence
<220> FEATURE:
<223> OTHER INFORMATION: 14th VH forward primer
```

<400> SEQUENCE: 43
ctcactctgc cgtctcagtg gtcgaggtgc agctgttgga gtctgg                46

<210> SEQ ID NO 44
<211> LENGTH: 45
<212> TYPE: DNA
<213> ORGANISM: Artificial Sequence
<220> FEATURE:
<223> OTHER INFORMATION: 15th VH forward primer

<400> SEQUENCE: 44
ctcactctgc cgtctcagtg gtcgaggtgc agctggtgga gactg                 45

<210> SEQ ID NO 45
<211> LENGTH: 46
<212> TYPE: DNA
<213> ORGANISM: Artificial Sequence
<220> FEATURE:
<223> OTHER INFORMATION: 16th VH forward primer

<400> SEQUENCE: 45
ctcactctgc cgtctcagtg gtcgaggtgc agctggtgga gtccgg                46

<210> SEQ ID NO 46
<211> LENGTH: 46
<212> TYPE: DNA
<213> ORGANISM: Artificial Sequence
<220> FEATURE:
<223> OTHER INFORMATION: 17th VH forward primer

<400> SEQUENCE: 46
ctcactctgc cgtctcagtg gtcgaggtgc agctggtgga gtctcg                46

<210> SEQ ID NO 47
<211> LENGTH: 46
<212> TYPE: DNA
<213> ORGANISM: Artificial Sequence
<220> FEATURE:
<223> OTHER INFORMATION: 18th VH forward primer

<400> SEQUENCE: 47
ctcactctgc cgtctcagtg gtccagctgc agctgcagga gtccgg                46

<210> SEQ ID NO 48
<211> LENGTH: 46
<212> TYPE: DNA
<213> ORGANISM: Artificial Sequence
<220> FEATURE:
<223> OTHER INFORMATION: 19th VH forward primer

<400> SEQUENCE: 48
ctcactctgc cgtctcagtg gtccaggtgc agctacagca gtgggg                46

<210> SEQ ID NO 49
<211> LENGTH: 46
<212> TYPE: DNA
<213> ORGANISM: Artificial Sequence
<220> FEATURE:
<223> OTHER INFORMATION: 20th VH forward primer

<400> SEQUENCE: 49
ctcactctgc cgtctcagtg gtccagctgc agctgcagga gtcggg                46

<210> SEQ ID NO 50
<211> LENGTH: 46

```
<212> TYPE: DNA
<213> ORGANISM: Artificial Sequence
<220> FEATURE:
<223> OTHER INFORMATION: 21st VH forward primer

<400> SEQUENCE: 50
ctcactctgc cgtctcagtg gtcgaggtgc agctggtgca gtctgg                46

<210> SEQ ID NO 51
<211> LENGTH: 46
<212> TYPE: DNA
<213> ORGANISM: Artificial Sequence
<220> FEATURE:
<223> OTHER INFORMATION: 22nd VH forward primer

<400> SEQUENCE: 51
ctcactctgc cgtctcagtg gtcgaagtgc agctggtgca gtctgg                46

<210> SEQ ID NO 52
<211> LENGTH: 46
<212> TYPE: DNA
<213> ORGANISM: Artificial Sequence
<220> FEATURE:
<223> OTHER INFORMATION: 23rd VH forward primer

<400> SEQUENCE: 52
ctcactctgc cgtctcagtg gtccaggtac agctgcagca gtcagg                46

<210> SEQ ID NO 53
<211> LENGTH: 46
<212> TYPE: DNA
<213> ORGANISM: Artificial Sequence
<220> FEATURE:
<223> OTHER INFORMATION: 24th VH forward primer

<400> SEQUENCE: 53
ctcactctgc cgtctcagtg gtccaggtgc agctggtgca atctgg                46

<210> SEQ ID NO 54
<211> LENGTH: 42
<212> TYPE: DNA
<213> ORGANISM: Artificial Sequence
<220> FEATURE:
<223> OTHER INFORMATION: 1st VH Reverse primer

<400> SEQUENCE: 54
cttggtggag gctgatgaga cggtgaccag ggtgccctgg cc                    42

<210> SEQ ID NO 55
<211> LENGTH: 42
<212> TYPE: DNA
<213> ORGANISM: Artificial Sequence
<220> FEATURE:
<223> OTHER INFORMATION: 2nd VH Reverse primer

<400> SEQUENCE: 55
cttggtggag gctgatgaga cggtgaccag ggtgccacgg cc                    42

<210> SEQ ID NO 56
<211> LENGTH: 42
<212> TYPE: DNA
<213> ORGANISM: Artificial Sequence
<220> FEATURE:
<223> OTHER INFORMATION: 3rd VH Reverse primer

<400> SEQUENCE: 56
```

-continued

```
cttggtggag gctgatgaga cggtgaccat tgtcccttgg cc                          42

<210> SEQ ID NO 57
<211> LENGTH: 42
<212> TYPE: DNA
<213> ORGANISM: Artificial Sequence
<220> FEATURE:
<223> OTHER INFORMATION: 4th VH Reverse primer

<400> SEQUENCE: 57
cttggtggag gctgatgaga cggtgaccag ggttccctgg cc                          42

<210> SEQ ID NO 58
<211> LENGTH: 42
<212> TYPE: DNA
<213> ORGANISM: Artificial Sequence
<220> FEATURE:
<223> OTHER INFORMATION: 5th VH Reverse primer

<400> SEQUENCE: 58
cttggtggag gctgatgaga cggtgaccgt ggtcccttgg cc                          42

<210> SEQ ID NO 59
<211> LENGTH: 52
<212> TYPE: DNA
<213> ORGANISM: Artificial Sequence
<220> FEATURE:
<223> OTHER INFORMATION: 1st LC forward primer

<400> SEQUENCE: 59
tggtggcagc ggccacaggg gcccactccg acatccagat gacccagtct cc              52

<210> SEQ ID NO 60
<211> LENGTH: 54
<212> TYPE: DNA
<213> ORGANISM: Artificial Sequence
<220> FEATURE:
<223> OTHER INFORMATION: 2nd LC forward primer

<400> SEQUENCE: 60
tggtggcagc ggccacaggg gcccactccg atattgtgat gacccagact ccac            54

<210> SEQ ID NO 61
<211> LENGTH: 52
<212> TYPE: DNA
<213> ORGANISM: Artificial Sequence
<220> FEATURE:
<223> OTHER INFORMATION: 3rd LC forward primer

<400> SEQUENCE: 61
tggtggcagc ggccacaggg gcccactccg ccatccagtt gacccagtct cc              52

<210> SEQ ID NO 62
<211> LENGTH: 52
<212> TYPE: DNA
<213> ORGANISM: Artificial Sequence
<220> FEATURE:
<223> OTHER INFORMATION: 4th LC forward primer

<400> SEQUENCE: 62
tggtggcagc ggccacaggg gcccactccg ccatccggat gacccagtct cc              52

<210> SEQ ID NO 63
<211> LENGTH: 54
<212> TYPE: DNA
<213> ORGANISM: Artificial Sequence
```

<220> FEATURE:
<223> OTHER INFORMATION: 5th LC forward primer

<400> SEQUENCE: 63
tggtggcagc ggccacaggg gcccactccg atgttgtgat gactcagtct ccac          54

<210> SEQ ID NO 64
<211> LENGTH: 54
<212> TYPE: DNA
<213> ORGANISM: Artificial Sequence
<220> FEATURE:
<223> OTHER INFORMATION: 6th LC forward primer

<400> SEQUENCE: 64
tggtggcagc ggccacaggg gcccactccg atattgtgat gactcagtct ccac          54

<210> SEQ ID NO 65
<211> LENGTH: 54
<212> TYPE: DNA
<213> ORGANISM: Artificial Sequence
<220> FEATURE:
<223> OTHER INFORMATION: 7th LC forward primer

<400> SEQUENCE: 65
tggtggcagc ggccacaggg gcccactccg aaattgtgtt gacgcagtct ccag          54

<210> SEQ ID NO 66
<211> LENGTH: 54
<212> TYPE: DNA
<213> ORGANISM: Artificial Sequence
<220> FEATURE:
<223> OTHER INFORMATION: 8th LC forward primer

<400> SEQUENCE: 66
tggtggcagc ggccacaggg gcccactccg aaatagtgat gacgcagtct ccag          54

<210> SEQ ID NO 67
<211> LENGTH: 54
<212> TYPE: DNA
<213> ORGANISM: Artificial Sequence
<220> FEATURE:
<223> OTHER INFORMATION: 9th LC forward primer

<400> SEQUENCE: 67
tggtggcagc ggccacaggg gcccactccg aaattgtgtt gacacagtct ccag          54

<210> SEQ ID NO 68
<211> LENGTH: 52
<212> TYPE: DNA
<213> ORGANISM: Artificial Sequence
<220> FEATURE:
<223> OTHER INFORMATION: 10th LC forward primer

<400> SEQUENCE: 68
tggtggcagc ggccacaggg gcccactccg aaattgtgct gactcagtct cc            52

<210> SEQ ID NO 69
<211> LENGTH: 52
<212> TYPE: DNA
<213> ORGANISM: Artificial Sequence
<220> FEATURE:
<223> OTHER INFORMATION: 11th LC forward primer

<400> SEQUENCE: 69
tggtggcagc ggccacaggg gcccactcca acatccagat gacccagtct cc            52

```
<210> SEQ ID NO 70
<211> LENGTH: 52
<212> TYPE: DNA
<213> ORGANISM: Artificial Sequence
<220> FEATURE:
<223> OTHER INFORMATION: 12th LC forward primer

<400> SEQUENCE: 70
tggtggcagc ggccacaggg gcccactccg acatccagtt gacccagtct cc          52

<210> SEQ ID NO 71
<211> LENGTH: 52
<212> TYPE: DNA
<213> ORGANISM: Artificial Sequence
<220> FEATURE:
<223> OTHER INFORMATION: 13th LC forward primer

<400> SEQUENCE: 71
tggtggcagc ggccacaggg gcccactccg tcatctggat gacccagtct cc          52

<210> SEQ ID NO 72
<211> LENGTH: 52
<212> TYPE: DNA
<213> ORGANISM: Artificial Sequence
<220> FEATURE:
<223> OTHER INFORMATION: 14th LC forward primer

<400> SEQUENCE: 72
tggtggcagc ggccacaggg gcccactccg ccatccagat gacccagtct cc          52

<210> SEQ ID NO 73
<211> LENGTH: 55
<212> TYPE: DNA
<213> ORGANISM: Artificial Sequence
<220> FEATURE:
<223> OTHER INFORMATION: 15th LC forward primer

<400> SEQUENCE: 73
tggtggcagc ggccacaggg gcccactccg aaattgtaat gacacagtct ccagc       55

<210> SEQ ID NO 74
<211> LENGTH: 52
<212> TYPE: DNA
<213> ORGANISM: Artificial Sequence
<220> FEATURE:
<223> OTHER INFORMATION: 16th LC forward primer

<400> SEQUENCE: 74
tggtggcagc ggccacaggg gcccactccg acatcgtgat gacccagtct cc          52

<210> SEQ ID NO 75
<211> LENGTH: 52
<212> TYPE: DNA
<213> ORGANISM: Artificial Sequence
<220> FEATURE:
<223> OTHER INFORMATION: 17th LC forward primer

<400> SEQUENCE: 75
tggtggcagc ggccacaggg gcccactccg aaacgacact cacgcagtct cc          52

<210> SEQ ID NO 76
<211> LENGTH: 54
<212> TYPE: DNA
<213> ORGANISM: Artificial Sequence
<220> FEATURE:
<223> OTHER INFORMATION: 18th LC forward primer
```

<400> SEQUENCE: 76
tggtggcagc ggccacaggg gcccactccg atgttgtgat gacacagtct ccag          54

<210> SEQ ID NO 77
<211> LENGTH: 52
<212> TYPE: DNA
<213> ORGANISM: Artificial Sequence
<220> FEATURE:
<223> OTHER INFORMATION: LC reverse primer

<400> SEQUENCE: 77
taaattcctc ggccgtgcag gccttatcaa cactctcccc tgttgaagct ct            52

<210> SEQ ID NO 78
<211> LENGTH: 13
<212> TYPE: DNA
<213> ORGANISM: Artificial Sequence
<220> FEATURE:
<223> OTHER INFORMATION: R1 or R8

<400> SEQUENCE: 78
ggcccaggcg gcc                                                        13

<210> SEQ ID NO 79
<211> LENGTH: 13
<212> TYPE: DNA
<213> ORGANISM: Artificial Sequence
<220> FEATURE:
<223> OTHER INFORMATION: R2 or R3

<400> SEQUENCE: 79
ggccacatag gcc                                                        13

<210> SEQ ID NO 80
<211> LENGTH: 13
<212> TYPE: DNA
<213> ORGANISM: Artificial Sequence
<220> FEATURE:
<223> OTHER INFORMATION: R4 or R5

<400> SEQUENCE: 80
ggcccaaccg gcc                                                        13

<210> SEQ ID NO 81
<211> LENGTH: 12
<212> TYPE: DNA
<213> ORGANISM: Artificial Sequence
<220> FEATURE:
<223> OTHER INFORMATION: R6 or R7

<400> SEQUENCE: 81
cgtctcctca gc                                                         12

<210> SEQ ID NO 82
<211> LENGTH: 46
<212> TYPE: DNA
<213> ORGANISM: Artificial Sequence
<220> FEATURE:
<223> OTHER INFORMATION: Forward primer for light chain KLC

<400> SEQUENCE: 82
tcgctaccgt ggcccaggcg gccgacatcc agatgaccca gtctcc                    46

<210> SEQ ID NO 83

-continued

```
<211> LENGTH: 48
<212> TYPE: DNA
<213> ORGANISM: Artificial Sequence
<220> FEATURE:
<223> OTHER INFORMATION: Forward primer for light chain KLC

<400> SEQUENCE: 83
tcgctaccgt ggcccaggcg gccgatattg tgatgaccca gactccac                48

<210> SEQ ID NO 84
<211> LENGTH: 46
<212> TYPE: DNA
<213> ORGANISM: Artificial Sequence
<220> FEATURE:
<223> OTHER INFORMATION: Forward primer for light chain KLC

<400> SEQUENCE: 84
tcgctaccgt ggcccaggcg gccgccatcc agttgaccca gtctcc                  46

<210> SEQ ID NO 85
<211> LENGTH: 46
<212> TYPE: DNA
<213> ORGANISM: Artificial Sequence
<220> FEATURE:
<223> OTHER INFORMATION: Forward primer for light chain KLC

<400> SEQUENCE: 85
tcgctaccgt ggcccaggcg gccgccatcc ggatgaccca gtctcc                  46

<210> SEQ ID NO 86
<211> LENGTH: 48
<212> TYPE: DNA
<213> ORGANISM: Artificial Sequence
<220> FEATURE:
<223> OTHER INFORMATION: Forward primer for light chain KLC

<400> SEQUENCE: 86
tcgctaccgt ggcccaggcg gccgatgttg tgatgactca gtctccac                48

<210> SEQ ID NO 87
<211> LENGTH: 48
<212> TYPE: DNA
<213> ORGANISM: Artificial Sequence
<220> FEATURE:
<223> OTHER INFORMATION: Forward primer for light chain KLC

<400> SEQUENCE: 87
tcgctaccgt ggcccaggcg gccgatattg tgatgactca gtctccac                48

<210> SEQ ID NO 88
<211> LENGTH: 48
<212> TYPE: DNA
<213> ORGANISM: Artificial Sequence
<220> FEATURE:
<223> OTHER INFORMATION: Forward primer for light chain KLC

<400> SEQUENCE: 88
tcgctaccgt ggcccaggcg gccgaaattg tgttgacgca gtctccag                48

<210> SEQ ID NO 89
<211> LENGTH: 48
<212> TYPE: DNA
<213> ORGANISM: Artificial Sequence
<220> FEATURE:
<223> OTHER INFORMATION: Forward primer for light chain KLC

<400> SEQUENCE: 89
```
tcgctaccgt ggcccaggcg gccgaaatag tgatgacgca gtctccag                          48

<210> SEQ ID NO 90
<211> LENGTH: 48
<212> TYPE: DNA
<213> ORGANISM: Artificial Sequence
<220> FEATURE:
<223> OTHER INFORMATION: Forward primer for light chain KLC

<400> SEQUENCE: 90
tcgctaccgt ggcccaggcg gccgaaattg tgttgacaca gtctccag                          48

<210> SEQ ID NO 91
<211> LENGTH: 46
<212> TYPE: DNA
<213> ORGANISM: Artificial Sequence
<220> FEATURE:
<223> OTHER INFORMATION: Forward primer for light chain KLC

<400> SEQUENCE: 91
tcgctaccgt ggcccaggcg gccgaaattg tgctgactca gtctcc                           46

<210> SEQ ID NO 92
<211> LENGTH: 46
<212> TYPE: DNA
<213> ORGANISM: Artificial Sequence
<220> FEATURE:
<223> OTHER INFORMATION: Forward primer for light chain KLC

<400> SEQUENCE: 92
tcgctaccgt ggcccaggcg gccaacatcc agatgaccca gtctcc                           46

<210> SEQ ID NO 93
<211> LENGTH: 46
<212> TYPE: DNA
<213> ORGANISM: Artificial Sequence
<220> FEATURE:
<223> OTHER INFORMATION: Forward primer for light chain KLC

<400> SEQUENCE: 93
tcgctaccgt ggcccaggcg gccgacatcc agttgaccca gtctcc                           46

<210> SEQ ID NO 94
<211> LENGTH: 46
<212> TYPE: DNA
<213> ORGANISM: Artificial Sequence
<220> FEATURE:
<223> OTHER INFORMATION: Forward primer for light chain KLC

<400> SEQUENCE: 94
tcgctaccgt ggcccaggcg gccgtcatct ggatgaccca gtctcc                           46

<210> SEQ ID NO 95
<211> LENGTH: 46
<212> TYPE: DNA
<213> ORGANISM: Artificial Sequence
<220> FEATURE:
<223> OTHER INFORMATION: Forward primer for light chain KLC

<400> SEQUENCE: 95
tcgctaccgt ggcccaggcg gccgccatcc agatgaccca gtctcc                           46

<210> SEQ ID NO 96
<211> LENGTH: 49
<212> TYPE: DNA

-continued

<213> ORGANISM: Artificial Sequence
<220> FEATURE:
<223> OTHER INFORMATION: Forward primer for light chain KLC

<400> SEQUENCE: 96
tcgctaccgt ggcccaggcg gccgaaattg taatgacaca gtctccagc                49

<210> SEQ ID NO 97
<211> LENGTH: 46
<212> TYPE: DNA
<213> ORGANISM: Artificial Sequence
<220> FEATURE:
<223> OTHER INFORMATION: Forward primer for light chain KLC

<400> SEQUENCE: 97
tcgctaccgt ggcccaggcg gccgacatcg tgatgaccca gtctcc                   46

<210> SEQ ID NO 98
<211> LENGTH: 46
<212> TYPE: DNA
<213> ORGANISM: Artificial Sequence
<220> FEATURE:
<223> OTHER INFORMATION: Forward primer for light chain KLC

<400> SEQUENCE: 98
tcgctaccgt ggcccaggcg gccgaaacga cactcacgca gtctcc                   46

<210> SEQ ID NO 99
<211> LENGTH: 48
<212> TYPE: DNA
<213> ORGANISM: Artificial Sequence
<220> FEATURE:
<223> OTHER INFORMATION: Forward primer for light chain KLC

<400> SEQUENCE: 99
tcgctaccgt ggcccaggcg gccgatgttg tgatgacaca gtctccag                 48

<210> SEQ ID NO 100
<211> LENGTH: 51
<212> TYPE: DNA
<213> ORGANISM: Artificial Sequence
<220> FEATURE:
<223> OTHER INFORMATION: Reverse primer for light chain KLC

<400> SEQUENCE: 100
taaattcctc ggcctatgtg gcctattaac actctcccct gttgaagctc t            51

<210> SEQ ID NO 101
<211> LENGTH: 46
<212> TYPE: DNA
<213> ORGANISM: Artificial Sequence
<220> FEATURE:
<223> OTHER INFORMATION: Forward primer for light chain LLC

<400> SEQUENCE: 101
tcgctaccgt ggcccaggcg gcccagtctg tgctgactca gccacc                   46

<210> SEQ ID NO 102
<211> LENGTH: 45
<212> TYPE: DNA
<213> ORGANISM: Artificial Sequence
<220> FEATURE:
<223> OTHER INFORMATION: Forward primer for light chain LLC

<400> SEQUENCE: 102
tcgctaccgt ggcccaggcg gcccagtctg ccctgactca gcctc                    45

-continued

```
<210> SEQ ID NO 103
<211> LENGTH: 45
<212> TYPE: DNA
<213> ORGANISM: Artificial Sequence
<220> FEATURE:
<223> OTHER INFORMATION: Forward primer for light chain LLC

<400> SEQUENCE: 103
tcgctaccgt ggcccaggcg gcccagtctg ccctgactca gcctg                            45

<210> SEQ ID NO 104
<211> LENGTH: 46
<212> TYPE: DNA
<213> ORGANISM: Artificial Sequence
<220> FEATURE:
<223> OTHER INFORMATION: Forward primer for light chain LLC

<400> SEQUENCE: 104
tcgctaccgt ggcccaggcg gcctcctatg agctgacaca gccacc                           46

<210> SEQ ID NO 105
<211> LENGTH: 46
<212> TYPE: DNA
<213> ORGANISM: Artificial Sequence
<220> FEATURE:
<223> OTHER INFORMATION: Forward primer for light chain LLC

<400> SEQUENCE: 105
tcgctaccgt ggcccaggcg gcctcctatg agctgacaca gccatc                           46

<210> SEQ ID NO 106
<211> LENGTH: 46
<212> TYPE: DNA
<213> ORGANISM: Artificial Sequence
<220> FEATURE:
<223> OTHER INFORMATION: Forward primer for light chain LLC

<400> SEQUENCE: 106
tcgctaccgt ggcccaggcg gcctcctatg agctgactca gccacc                           46

<210> SEQ ID NO 107
<211> LENGTH: 47
<212> TYPE: DNA
<213> ORGANISM: Artificial Sequence
<220> FEATURE:
<223> OTHER INFORMATION: Forward primer for light chain LLC

<400> SEQUENCE: 107
tcgctaccgt ggcccaggcg gcctcctatg agctgactca gccactc                          47

<210> SEQ ID NO 108
<211> LENGTH: 46
<212> TYPE: DNA
<213> ORGANISM: Artificial Sequence
<220> FEATURE:
<223> OTHER INFORMATION: Forward primer for light chain LLC

<400> SEQUENCE: 108
tcgctaccgt ggcccaggcg gcccagtctg tgctgacgca gccgcc                           46

<210> SEQ ID NO 109
<211> LENGTH: 45
<212> TYPE: DNA
<213> ORGANISM: Artificial Sequence
<220> FEATURE:
```

<223> OTHER INFORMATION: Forward primer for light chain LLC

<400> SEQUENCE: 109
tcgctaccgt ggcccaggcg gcccagtctg tgttgacgca gccgc                           45

<210> SEQ ID NO 110
<211> LENGTH: 46
<212> TYPE: DNA
<213> ORGANISM: Artificial Sequence
<220> FEATURE:
<223> OTHER INFORMATION: Forward primer for light chain LLC

<400> SEQUENCE: 110
tcgctaccgt ggcccaggcg gcctcttctg agctgactca ggaccc                          46

<210> SEQ ID NO 111
<211> LENGTH: 46
<212> TYPE: DNA
<213> ORGANISM: Artificial Sequence
<220> FEATURE:
<223> OTHER INFORMATION: Forward primer for light chain LLC

<400> SEQUENCE: 111
tcgctaccgt ggcccaggcg gcctcctatg tgctgactca gccacc                          46

<210> SEQ ID NO 112
<211> LENGTH: 46
<212> TYPE: DNA
<213> ORGANISM: Artificial Sequence
<220> FEATURE:
<223> OTHER INFORMATION: Forward primer for light chain LLC

<400> SEQUENCE: 112
tcgctaccgt ggcccaggcg gcctcctatg agctgacaca gctacc                          46

<210> SEQ ID NO 113
<211> LENGTH: 46
<212> TYPE: DNA
<213> ORGANISM: Artificial Sequence
<220> FEATURE:
<223> OTHER INFORMATION: Forward primer for light chain LLC

<400> SEQUENCE: 113
tcgctaccgt ggcccaggcg gcctcctatg agctgatgca gccacc                          46

<210> SEQ ID NO 114
<211> LENGTH: 45
<212> TYPE: DNA
<213> ORGANISM: Artificial Sequence
<220> FEATURE:
<223> OTHER INFORMATION: Forward primer for light chain LLC

<400> SEQUENCE: 114
tcgctaccgt ggcccaggcg gccctgcctg tgctgactca gcccc                           45

<210> SEQ ID NO 115
<211> LENGTH: 47
<212> TYPE: DNA
<213> ORGANISM: Artificial Sequence
<220> FEATURE:
<223> OTHER INFORMATION: Forward primer for light chain LLC

<400> SEQUENCE: 115
tcgctaccgt ggcccaggcg gcccagcctg tgctgactca atcatcc                         47

-continued

```
<210> SEQ ID NO 116
<211> LENGTH: 46
<212> TYPE: DNA
<213> ORGANISM: Artificial Sequence
<220> FEATURE:
<223> OTHER INFORMATION: Forward primer for light chain LLC

<400> SEQUENCE: 116
tcgctaccgt ggcccaggcg gcccagcttg tgctgactca atcgcc                    46

<210> SEQ ID NO 117
<211> LENGTH: 46
<212> TYPE: DNA
<213> ORGANISM: Artificial Sequence
<220> FEATURE:
<223> OTHER INFORMATION: Forward primer for light chain LLC

<400> SEQUENCE: 117
tcgctaccgt ggcccaggcg gcccagcctg tgctgactca gccacc                    46

<210> SEQ ID NO 118
<211> LENGTH: 45
<212> TYPE: DNA
<213> ORGANISM: Artificial Sequence
<220> FEATURE:
<223> OTHER INFORMATION: Forward primer for light chain LLC

<400> SEQUENCE: 118
tcgctaccgt ggcccaggcg gcccaggctg tgctgactca gccgg                     45

<210> SEQ ID NO 119
<211> LENGTH: 46
<212> TYPE: PRT
<213> ORGANISM: Artificial Sequence
<220> FEATURE:
<223> OTHER INFORMATION: Forward primer for light chain LLC

<400> SEQUENCE: 119

Thr Cys Gly Cys Thr Ala Cys Cys Gly Thr Gly Gly Cys Cys Cys Ala
1               5                   10                  15

Gly Gly Cys Gly Gly Cys Cys Cys Ala Gly Cys Cys Thr Gly Thr Gly
            20                  25                  30

Cys Thr Gly Ala Cys Thr Cys Ala Gly Cys Cys Ala Thr Cys
        35                  40                  45

<210> SEQ ID NO 120
<211> LENGTH: 47
<212> TYPE: DNA
<213> ORGANISM: Artificial Sequence
<220> FEATURE:
<223> OTHER INFORMATION: Forward primer for light chain LLC

<400> SEQUENCE: 120
tcgctaccgt ggcccaggcg gccaatttta tgctgactca gccccac                   47

<210> SEQ ID NO 121
<211> LENGTH: 46
<212> TYPE: DNA
<213> ORGANISM: Artificial Sequence
<220> FEATURE:
<223> OTHER INFORMATION: Forward primer for light chain LLC

<400> SEQUENCE: 121
tcgctaccgt ggcccaggcg gcccagactg tggtgactca ggagcc                    46
```

<210> SEQ ID NO 122
<211> LENGTH: 45
<212> TYPE: DNA
<213> ORGANISM: Artificial Sequence
<220> FEATURE:
<223> OTHER INFORMATION: Forward primer for light chain LLC

<400> SEQUENCE: 122
tcgctaccgt ggcccaggcg gcccaggctg tggtgactca ggagc                      45

<210> SEQ ID NO 123
<211> LENGTH: 45
<212> TYPE: DNA
<213> ORGANISM: Artificial Sequence
<220> FEATURE:
<223> OTHER INFORMATION: Forward primer for light chain LLC

<400> SEQUENCE: 123
tcgctaccgt ggcccaggcg gcccagactg tggtgaccca ggagc                      45

<210> SEQ ID NO 124
<211> LENGTH: 45
<212> TYPE: DNA
<213> ORGANISM: Artificial Sequence
<220> FEATURE:
<223> OTHER INFORMATION: Forward primer for light chain LLC

<400> SEQUENCE: 124
tcgctaccgt ggcccaggcg gcccagcctg tgctgactca gccac                      45

<210> SEQ ID NO 125
<211> LENGTH: 45
<212> TYPE: DNA
<213> ORGANISM: Artificial Sequence
<220> FEATURE:
<223> OTHER INFORMATION: Forward primer for light chain LLC

<400> SEQUENCE: 125
tcgctaccgt ggcccaggcg gcccaggcag ggctgactca gccac                      45

<210> SEQ ID NO 126
<211> LENGTH: 51
<212> TYPE: DNA
<213> ORGANISM: Artificial Sequence
<220> FEATURE:
<223> OTHER INFORMATION: Reverse primer for light chain LLC

<400> SEQUENCE: 126
taaattcctc ggcctatgtg gcctattatg aacattctgt aggggccact g              51

<210> SEQ ID NO 127
<211> LENGTH: 51
<212> TYPE: DNA
<213> ORGANISM: Artificial Sequence
<220> FEATURE:
<223> OTHER INFORMATION: Forward primer for VH

<400> SEQUENCE: 127
tattacttgc ggcccaaccg gccatggccg aggtgcagct ggtggagtct g              51

<210> SEQ ID NO 128
<211> LENGTH: 51
<212> TYPE: DNA
<213> ORGANISM: Artificial Sequence
<220> FEATURE:
<223> OTHER INFORMATION: Forward primer for VH -continued

```
<400> SEQUENCE: 128
tattacttgc ggcccaaccg gccatggccc aggtgcagct gcaggagtcg g          51

<210> SEQ ID NO 129
<211> LENGTH: 51
<212> TYPE: DNA
<213> ORGANISM: Artificial Sequence
<220> FEATURE:
<223> OTHER INFORMATION: Forward primer for VH

<400> SEQUENCE: 129
tattacttgc ggcccaaccg gccatggccc aggtgcagct ggtgcagtct g          51

<210> SEQ ID NO 130
<211> LENGTH: 51
<212> TYPE: DNA
<213> ORGANISM: Artificial Sequence
<220> FEATURE:
<223> OTHER INFORMATION: Forward primer for VH

<400> SEQUENCE: 130
tattacttgc ggcccaaccg gccatggccc aggtgcagct ggtggagtct g          51

<210> SEQ ID NO 131
<211> LENGTH: 52
<212> TYPE: DNA
<213> ORGANISM: Artificial Sequence
<220> FEATURE:
<223> OTHER INFORMATION: Forward primer for VH

<400> SEQUENCE: 131
tattacttgc ggcccaaccg gccatggccc aggtcacctt gaaggagtct gg          52

<210> SEQ ID NO 132
<211> LENGTH: 52
<212> TYPE: DNA
<213> ORGANISM: Artificial Sequence
<220> FEATURE:
<223> OTHER INFORMATION: Forward primer for VH

<400> SEQUENCE: 132
tattacttgc ggcccaaccg gccatggccg aagtgcagct ggtggagtct gg          52

<210> SEQ ID NO 133
<211> LENGTH: 52
<212> TYPE: DNA
<213> ORGANISM: Artificial Sequence
<220> FEATURE:
<223> OTHER INFORMATION: Forward primer for VH

<400> SEQUENCE: 133
tattacttgc ggcccaaccg gccatggccc aggtccagct tgtgcagtct gg          52

<210> SEQ ID NO 134
<211> LENGTH: 52
<212> TYPE: DNA
<213> ORGANISM: Artificial Sequence
<220> FEATURE:
<223> OTHER INFORMATION: Forward primer for VH

<400> SEQUENCE: 134
tattacttgc ggcccaaccg gccatggccc aggttcagct ggtgcagtct gg          52

<210> SEQ ID NO 135
<211> LENGTH: 52
```

<212> TYPE: DNA
<213> ORGANISM: Artificial Sequence
<220> FEATURE:
<223> OTHER INFORMATION: Forward primer for VH

<400> SEQUENCE: 135
tattacttgc ggcccaaccg gccatggccc aggtccagct ggtacagtct gg          52

<210> SEQ ID NO 136
<211> LENGTH: 52
<212> TYPE: DNA
<213> ORGANISM: Artificial Sequence
<220> FEATURE:
<223> OTHER INFORMATION: Forward primer for VH

<400> SEQUENCE: 136
tattacttgc ggcccaaccg gccatggccc agatgcagct ggtgcagtct gg          52

<210> SEQ ID NO 137
<211> LENGTH: 52
<212> TYPE: DNA
<213> ORGANISM: Artificial Sequence
<220> FEATURE:
<223> OTHER INFORMATION: Forward primer for VH

<400> SEQUENCE: 137
tattacttgc ggcccaaccg gccatggccc aaatgcagct ggtgcagtct gg          52

<210> SEQ ID NO 138
<211> LENGTH: 52
<212> TYPE: DNA
<213> ORGANISM: Artificial Sequence
<220> FEATURE:
<223> OTHER INFORMATION: Forward primer for VH

<400> SEQUENCE: 138
tattacttgc ggcccaaccg gccatggccg aggtccagct ggtacagtct gg          52

<210> SEQ ID NO 139
<211> LENGTH: 52
<212> TYPE: DNA
<213> ORGANISM: Artificial Sequence
<220> FEATURE:
<223> OTHER INFORMATION: Forward primer for VH

<400> SEQUENCE: 139
tattacttgc ggcccaaccg gccatggccc agatcacctt gaaggagtct gg          52

<210> SEQ ID NO 140
<211> LENGTH: 52
<212> TYPE: DNA
<213> ORGANISM: Artificial Sequence
<220> FEATURE:
<223> OTHER INFORMATION: Forward primer for VH

<400> SEQUENCE: 140
tattacttgc ggcccaaccg gccatggccg aggtgcagct gttggagtct gg          52

<210> SEQ ID NO 141
<211> LENGTH: 51
<212> TYPE: DNA
<213> ORGANISM: Artificial Sequence
<220> FEATURE:
<223> OTHER INFORMATION: Forward primer for VH

<400> SEQUENCE: 141

```
tattacttgc ggcccaaccg gccatggccg aggtgcagct ggtggagact g                      51
```

```
<210> SEQ ID NO 142
<211> LENGTH: 52
<212> TYPE: DNA
<213> ORGANISM: Artificial Sequence
<220> FEATURE:
<223> OTHER INFORMATION: Forward primer for VH

<400> SEQUENCE: 142
tattacttgc ggcccaaccg gccatggccg aggtgcagct ggtggagtcc gg                     52

<210> SEQ ID NO 143
<211> LENGTH: 52
<212> TYPE: DNA
<213> ORGANISM: Artificial Sequence
<220> FEATURE:
<223> OTHER INFORMATION: Forward primer for VH

<400> SEQUENCE: 143
tattacttgc ggcccaaccg gccatggccg aggtgcagct ggtggagtct cg                     52

<210> SEQ ID NO 144
<211> LENGTH: 52
<212> TYPE: DNA
<213> ORGANISM: Artificial Sequence
<220> FEATURE:
<223> OTHER INFORMATION: Forward primer for VH

<400> SEQUENCE: 144
tattacttgc ggcccaaccg gccatggccc agctgcagct gcaggagtcc gg                     52

<210> SEQ ID NO 145
<211> LENGTH: 52
<212> TYPE: DNA
<213> ORGANISM: Artificial Sequence
<220> FEATURE:
<223> OTHER INFORMATION: Forward primer for VH

<400> SEQUENCE: 145
tattacttgc ggcccaaccg gccatggccc aggtgcagct acagcagtgg gg                     52

<210> SEQ ID NO 146
<211> LENGTH: 52
<212> TYPE: DNA
<213> ORGANISM: Artificial Sequence
<220> FEATURE:
<223> OTHER INFORMATION: Forward primer for VH

<400> SEQUENCE: 146
tattacttgc ggcccaaccg gccatggccc agctgcagct gcaggagtcg gg                     52

<210> SEQ ID NO 147
<211> LENGTH: 52
<212> TYPE: DNA
<213> ORGANISM: Artificial Sequence
<220> FEATURE:
<223> OTHER INFORMATION: Forward primer for VH

<400> SEQUENCE: 147
tattacttgc ggcccaaccg gccatggccg aggtgcagct ggtgcagtct gg                     52

<210> SEQ ID NO 148
<211> LENGTH: 52
<212> TYPE: DNA
<213> ORGANISM: Artificial Sequence
```

-continued

<220> FEATURE:
<223> OTHER INFORMATION: Forward primer for VH

<400> SEQUENCE: 148
tattacttgc ggcccaaccg gccatggccg aagtgcagct ggtgcagtct gg          52

<210> SEQ ID NO 149
<211> LENGTH: 52
<212> TYPE: DNA
<213> ORGANISM: Artificial Sequence
<220> FEATURE:
<223> OTHER INFORMATION: Forward primer for VH

<400> SEQUENCE: 149
tattacttgc ggcccaaccg gccatggccc aggtacagct gcagcagtca gg          52

<210> SEQ ID NO 150
<211> LENGTH: 52
<212> TYPE: DNA
<213> ORGANISM: Artificial Sequence
<220> FEATURE:
<223> OTHER INFORMATION: Forward primer for VH

<400> SEQUENCE: 150
tattacttgc ggcccaaccg gccatggccc aggtgcagct ggtgcaatct gg          52

<210> SEQ ID NO 151
<211> LENGTH: 42
<212> TYPE: DNA
<213> ORGANISM: Artificial Sequence
<220> FEATURE:
<223> OTHER INFORMATION: Reverse primer for VH

<400> SEQUENCE: 151
cttggtggag gctgaggaga cggtgaccag ggtgccctgg cc          42

<210> SEQ ID NO 152
<211> LENGTH: 42
<212> TYPE: DNA
<213> ORGANISM: Artificial Sequence
<220> FEATURE:
<223> OTHER INFORMATION: Reverse primer for VH

<400> SEQUENCE: 152
cttggtggag gctgaggaga cggtgaccag ggtgccacgg cc          42

<210> SEQ ID NO 153
<211> LENGTH: 42
<212> TYPE: DNA
<213> ORGANISM: Artificial Sequence
<220> FEATURE:
<223> OTHER INFORMATION: Reverse primer for VH

<400> SEQUENCE: 153
cttggtggag gctgaggaga cggtgaccat tgtcccttgg cc          42

<210> SEQ ID NO 154
<211> LENGTH: 42
<212> TYPE: DNA
<213> ORGANISM: Artificial Sequence
<220> FEATURE:
<223> OTHER INFORMATION: Reverse primer for VH

<400> SEQUENCE: 154
cttggtggag gctgaggaga cggtgaccag ggttccctgg cc          42

<210> SEQ ID NO 155
<211> LENGTH: 42
<212> TYPE: DNA
<213> ORGANISM: Artificial Sequence
<220> FEATURE:
<223> OTHER INFORMATION: Reverse primer for VH

<400> SEQUENCE: 155
cttggtggag gctgaggaga cggtgaccgt ggtcccttgg cc                               42

<210> SEQ ID NO 156
<211> LENGTH: 22
<212> TYPE: DNA
<213> ORGANISM: Artificial Sequence
<220> FEATURE:
<223> OTHER INFORMATION: Forward primer for linker

<400> SEQUENCE: 156
acagcttgtc tgtaagcgga tg                                                     22

<210> SEQ ID NO 157
<211> LENGTH: 22
<212> TYPE: DNA
<213> ORGANISM: Artificial Sequence
<220> FEATURE:
<223> OTHER INFORMATION: Reverse primer for linker

<400> SEQUENCE: 157
tgtggataac cgtattaccg cc                                                     22

<210> SEQ ID NO 158
<211> LENGTH: 59
<212> TYPE: DNA
<213> ORGANISM: Artificial Sequence
<220> FEATURE:
<223> OTHER INFORMATION: Forward primer for R1-1kb-R2

<400> SEQUENCE: 158
ttagcgaatt ccagacatct aatggcccag gcggcctcag ctagcaccaa gggcccatc           59

<210> SEQ ID NO 159
<211> LENGTH: 59
<212> TYPE: DNA
<213> ORGANISM: Artificial Sequence
<220> FEATURE:
<223> OTHER INFORMATION: Reverse primer for R1-1kb-R2

<400> SEQUENCE: 159
cgggtgatca ccagtcttct attggcctat gtggccttat catttacccg gagacaggg           59

<210> SEQ ID NO 160
<211> LENGTH: 55
<212> TYPE: DNA
<213> ORGANISM: Artificial Sequence
<220> FEATURE:
<223> OTHER INFORMATION: Forward primer for R3-linker-R4

<400> SEQUENCE: 160
taggccacat aggccgagga atttaaaatg aaatacctat tgcctacggc agccg              55

<210> SEQ ID NO 161
<211> LENGTH: 54
<212> TYPE: DNA
<213> ORGANISM: Artificial Sequence
<220> FEATURE:
<223> OTHER INFORMATION: Reverse primer for R3-linker-R4

-continued

```
<400> SEQUENCE: 161
atggccggtt gggccgcaag taataacaat ccagcggctg ccgtaggcaa tagg        54

<210> SEQ ID NO 162
<211> LENGTH: 59
<212> TYPE: DNA
<213> ORGANISM: Artificial Sequence
<220> FEATURE:
<223> OTHER INFORMATION: Forward primer for R5-1kb-R6

<400> SEQUENCE: 162
ttagcgaatt ccagacatct aatggcccaa ccggcctcag ctagcaccaa gggcccatc        59

<210> SEQ ID NO 163
<211> LENGTH: 51
<212> TYPE: DNA
<213> ORGANISM: Artificial Sequence
<220> FEATURE:
<223> OTHER INFORMATION: Reverse primer for R5-1kb-R6

<400> SEQUENCE: 163
tgatcaccag tcttctattg gctgaggaga cgttatcatt tacccggaga c        51

<210> SEQ ID NO 164
<211> LENGTH: 987
<212> TYPE: DNA
<213> ORGANISM: Homo sapiens

<400> SEQUENCE: 164
tcagctagca ccaagggccc atcggtcttc cccctggcgc cctgctccag gagcacctcc        60
gagagcacag cggccctggg ctgcctggtc aaggactact cccccgaacc ggtgacggtg       120
tcgtggaact caggcgctct gaccagcggc gtgcacacct cccagctgt cctacagtcc        180 tcaggactct actccctcag cagcgtggtg accgtgccct ccagcaactt cggcacccag       240
acctacacct gcaacgtaga tcacaagccc agcaacacca aggtggacaa gacagttgag       300
cgcaaatgtt gtgtcgagtg cccaccgtgc ccagcaccac ctgtggcagg accgtcagtc       360
ttcctcttcc ccccaaaacc caaggacacc ctcatgatct cccggacccc tgaggtcacg       420
tgcgtggtgg tggacgtgag ccacgaagac cccgaggtcc agttcaactg gtacgtggac       480
ggcgtggagg tgcataatgc caagacaaag ccacgggagg agcagttcaa cagcacgttc       540
cgtgtggtca gcgtcctcac cgttgtgcac caggactggc tgaacggcaa ggagtacaag       600
tgcaaggtct ccaacaaagg cctcccagcc cccatcgaga aaaccatctc caaaaccaaa       660
gggcagcccc gagaaccaca ggtgtacacc ctgcccccat cccgggagga tgaccaag        720 aaccaggtca gcctgacctg cctggtcaaa ggcttctacc ccagcgacat cgccgtggag       780
tgggagagca atgggcagcc ggagaacaac tacaagacca cacctccat gctggactcc        840 gacggctcct tcttcctcta cagcaagctc accgtggaca gagcaggtg gcagcagggg        900 aacgtcttct catgctccgt gatgcatgag gctctgcaca accactacac gcagaagagc       960
ctctccctgt ctccgggtaa atgataa                                           987

<210> SEQ ID NO 165
<211> LENGTH: 1013
<212> TYPE: DNA
<213> ORGANISM: Artificial Sequence
<220> FEATURE:
<223> OTHER INFORMATION: R1-1kb-R2
```

<400> SEQUENCE: 165
ggcccaggcg gcctcagcta gcaccaaggg cccatcggtc ttccccctgg cgccctgctc      60
caggagcacc tccgagagca cagcggccct gggctgcctg gtcaaggact acttccccga     120
accggtgacg gtgtcgtgga actcaggcgc tctgaccagc ggcgtgcaca ccttcccagc     180
tgtcctacag tcctcaggac tctactccct cagcagcgtg gtgaccgtgc cctccagcaa     240
cttcggcacc cagacctaca cctgcaacgt agatcacaag cccagcaaca ccaaggtgga     300
caagacagtt gagcgcaaat gttgtgtcga gtgcccaccg tgcccagcac cacctgtggc     360
aggaccgtca gtcttcctct tccccccaaa acccaaggac accctcatga tctcccggac     420
ccctgaggtc acgtgcgtgg tggtggacgt gagccacgaa gaccccgagg tccagttcaa     480
ctggtacgtg gacggcgtgg aggtgcataa tgccaagaca aagccacggg aggagcagtt     540
caacagcacg ttccgtgtgg tcagcgtcct caccgttgtg caccaggact ggctgaacgg     600
caaggagtac aagtgcaagg tctccaacaa aggcctccca gcccccatcg agaaaaccat     660
ctccaaaacc aaagggcagc cccgagaacc acaggtgtac accctgcccc catcccggga     720
ggagatgacc aagaaccagg tcagcctgac ctgcctggtc aaaggcttct accccagcga     780
catcgccgtg gagtgggaga gcaatgggca gccggagaac aactacaaga ccacacctcc     840
catgctggac tccgacggct ccttcttcct ctacagcaag ctcaccgtgg acaagagcag     900
gtggcagcag gggaacgtct tctcatgctc cgtgatgcat gaggctctgc acaaccacta     960
cacgcagaag agcctctccc tgtctccggg taaatgataa ggccacatag gcc          1013

<210> SEQ ID NO 166
<211> LENGTH: 72
<212> TYPE: DNA
<213> ORGANISM: Artificial Sequence
<220> FEATURE:
<223> OTHER INFORMATION: 72bp-long linker

<400> SEQUENCE: 166
aggccgagga atttaaaatg aaatacctat tgcctacggc agccgctgga ttgttattac      60
ttgcggccca ac                                                         72

<210> SEQ ID NO 167
<211> LENGTH: 85
<212> TYPE: DNA
<213> ORGANISM: Artificial Sequence
<220> FEATURE:
<223> OTHER INFORMATION: R3-linker(72bp)-R4

<400> SEQUENCE: 167
ggccacatag gccgaggaat ttaaaatgaa atacctattg cctacggcag ccgctggatt      60
gttattactt gcggcccaac cggcc                                           85

<210> SEQ ID NO 168
<211> LENGTH: 1012
<212> TYPE: DNA
<213> ORGANISM: Artificial Sequence
<220> FEATURE:
<223> OTHER INFORMATION: R5-1kb-R6

<400> SEQUENCE: 168
ggcccaaccg gcctcagcta gcaccaaggg cccatcggtc ttccccctgg cgccctgctc      60
caggagcacc tccgagagca cagcggccct gggctgcctg gtcaaggact acttccccga     120
accggtgacg gtgtcgtgga actcaggcgc tctgaccagc ggcgtgcaca ccttcccagc     180

-continued

```
tgtcctacag tcctcaggac tctactccct cagcagcgtg gtgaccgtgc cctccagcaa        240
cttcggcacc cagacctaca cctgcaacgt agatcacaag cccagcaaca ccaaggtgga        300
caagacagtt gagcgcaaat gttgtgtcga gtgcccaccg tgcccagcac cacctgtggc        360
aggaccgtca gtcttcctct tccccccaaa acccaaggac accctcatga tctcccggac        420
ccctgaggtc acgtgcgtgg tggtggacgt gagccacgaa gaccccgagg tccagttcaa        480
ctggtacgtg gacggcgtgg aggtgcataa tgccaagaca aagccacggg aggagcagtt        540
caacagcacg ttccgtgtgg tcagcgtcct caccgttgtg caccaggact ggctgaacgg        600
caaggagtac aagtgcaagg tctccaacaa aggcctccca gcccccatcg agaaaaccat        660
ctccaaaacc aaagggcagc cccgagaacc acaggtgtac accctgcccc catcccggga        720
ggagatgacc aagaaccagg tcagcctgac ctgcctggtc aaaggcttct accccagcga        780
catcgccgtg gagtgggaga gcaatgggca gccggagaac aactacaaga ccacacctcc        840
catgctggac tccgacggct ccttcttcct ctacagcaag ctcaccgtgg acaagagcag        900
gtggcagcag gggaacgtct tctcatgctc cgtgatgcat gaggctctgc acaaccacta        960
cacgcagaag agcctctccc tgtctccggg taaatgataa cgtctcctca gc              1012
```

```
<210> SEQ ID NO 169
<211> LENGTH: 61
<212> TYPE: DNA
<213> ORGANISM: Artificial Sequence
<220> FEATURE:
<223> OTHER INFORMATION: Forward primer for mutation of pUC19 vector

<400> SEQUENCE: 169
atgacggtgt aacctctga cacatgcagc tcccggagaa ggtcacagct tgtctgtaag         60
c                                                                          61
```

```
<210> SEQ ID NO 170
<211> LENGTH: 57
<212> TYPE: DNA
<213> ORGANISM: Artificial Sequence
<220> FEATURE:
<223> OTHER INFORMATION: Reverse primer for mutation of pUC19 vector

<400> SEQUENCE: 170
gtcagaggtt aacaccgtca tcaccgaaac gcgcgacacg aaagggcctc gtgatac          57
```

```
<210> SEQ ID NO 171
<211> LENGTH: 90
<212> TYPE: DNA
<213> ORGANISM: Artificial Sequence
<220> FEATURE:
<223> OTHER INFORMATION: 90bp long linker

<400> SEQUENCE: 171
aggccttcta gataattaat taggaggaat ttaaaatgaa atacctattg cctacggcag         60
ccgctggatt gttattactt gcggcccaac                                          90
```

```
<210> SEQ ID NO 172
<211> LENGTH: 103
<212> TYPE: DNA
<213> ORGANISM: Artificial Sequence
<220> FEATURE:
<223> OTHER INFORMATION: R3-linker(90bp)-R4

<400> SEQUENCE: 172
```

-continued

```
ggccacatag gccttctaga taattaatta ggaggaattt aaaatgaaat acctattgcc        60
tacggcagcc gctggattgt tattacttgc ggcccaaccg gcc                        103

<210> SEQ ID NO 173
<211> LENGTH: 44
<212> TYPE: DNA
<213> ORGANISM: Artificial Sequence
<220> FEATURE:
<223> OTHER INFORMATION: Forward primer for 90bp linker

<400> SEQUENCE: 173
agtgttaata ggccacatag gccttctaga taattaatta ggag                        44

<210> SEQ ID NO 174
<211> LENGTH: 42
<212> TYPE: DNA
<213> ORGANISM: Artificial Sequence
<220> FEATURE:
<223> OTHER INFORMATION: Forward primer for 90bp linker

<400> SEQUENCE: 174
ccttctagat aattaattag gaggaattta aaatgaaata cc                          42

<210> SEQ ID NO 175
<211> LENGTH: 29
<212> TYPE: DNA
<213> ORGANISM: Artificial Sequence
<220> FEATURE:
<223> OTHER INFORMATION: Reverse primer for 90bp linker

<400> SEQUENCE: 175
acctcggcca tggccggttg ggccgcaag                                         29
```

CONSTRUCTION METHOD AND APPLICATION OF ANTIGEN-SPECIFIC BINDING POLYPEPTIDE GENE DISPLAY VECTOR

CROSS REFERENCE TO RELATED APPLICATIONS

This application is a National Stage Application and claims priority under 35 U.S.C. § 371 to Patent Cooperation Treaty application PCT/CN2021/083246, filed Mar. 26, 2021, which claims the benefit of Chinese Patent Application No. 202010231148.1, filed Mar. 27, 2020. Priority is claimed to these applications and the disclosure of these prior applications is considered part of the disclosure of this application and to the extent allowed the entire contents of the aforementioned applications are incorporated herein.

SEQUENCE LISTING

This application incorporates by reference in its entirety the Sequence Listing entitled "2022-09-26_262790-516285_ST25", is 55,116 bytes in size and was created on Sep. 26, 2022, and filed electronically herewith.

FIELD OF THE INVENTION

The present application relates to the field of biomedicine, and specifically to a method for constructing an antigen-specific binding polypeptide gene display vector which can be used for screening antigen-specific binding polypeptides.

BACKGROUND OF THE INVENTION

Currently, there are two main categories of antibody discovery methods commonly used in the prior art: hybridoma technology and antibody display technology. The hybridoma technology further includes two types of murine hybridoma and transgenic mouse hybridoma. There are mainly three types of antibody display technology: phage display, yeast display and mammalian cell display, respectively. Each antibody discovery technology has very clear advantages, but also very significant disadvantages and limitations. For example, the lack of quality control in the process of constructing an antibody drug seed bank results in poor quality, small library capacity, low diversity, low effective clone proportion of the antibody library, thus making it difficult to screen high-quality lead antibodies; alternatively, the antibody library screening technology has no quantitative screening, and the screening throughput is small, the screening effect is poor and the screening is time-consuming.

Therefore, an innovative antibody discovery technology is needed to improve the quality, quantity and diversity of lead antibody molecules for screening innovative antibody drugs, speed up the development of antibody drugs and improve the success rate of development.

SUMMARY OF THE INVENTION

The present application provides a method for constructing an antigen-specific binding polypeptide gene display vector. The antigen-specific binding polypeptide gene display vector is composed of four fragments, in which the 5' and 3'-ends of the four fragments are provided with sticky ends of specific sequences by constructing component libraries and display vectors so that they are directionally cyclized to form the antigen-specific binding polypeptide gene display vector. The method for constructing an antigen-specific binding polypeptide gene display vector of the present application and the method for screening an antigen-specific binding polypeptide by using the antigen-specific binding polypeptide gene display vector of the present application possess at least one of the following properties: 1) special recognition sites for restriction endonuclease can be used in constructing the antigen-specific binding polypeptide gene display vector of the present application, which not only ensures directional ligation, but also prevents wrong ligation, and the number of molecules of each component fragment can be controlled to 1:1 during the ligation, thus improving the efficiency of ligation and transformation; meanwhile, strategies of constructing a VH component library and a LC component library are employed to improve the efficiency of ligation and transformation of each fragment; 2) the combinatorial PCR strategy used in conventional antibody library construction methods in the art is not employed, effectively reducing the probability of introducing mutations caused by PCR; 3) it is easier to perform quality control, and it can meet the needs of industrial mass production; 4) the display vector can be directly screened by biological activity analysis experiments after being introduced into a cell, effectively shortening the time from constructing an antigen-specific binding polypeptide gene display vector to screening an antigen-specific polypeptide of a unique sequence. For example, the time from constructing a display vector to screening a positive clone of a unique sequence can be at least about 1 week (at least about 10 days, at least about 2 weeks, at least about 3 weeks, at least about 4 weeks, at least about 5 weeks, at least about 6 weeks, at least about 7 weeks, at least about 8 weeks); 5) the diversity of clones in the display vector bacterial library is large and the screening efficiency is high. In some cases, in the library comprising antigen-specific binding polypeptide gene display vectors, the proportion of effective clones can be up to more than about 50% (e.g., more than about 55%, more than about 60%, more than about 65%, more than about 70%, more than about 75%, more than about 80%, more than about 85%, more than about 90%, more than about 95% or higher), so that the transformation efficiency is high, and the success rate of library construction is high.

In one aspect, the present application provides a method for constructing an antigen-specific binding polypeptide gene display vector. The method includes: a) providing a first display vector polynucleotide comprising B2-display VH-B3 in the direction from 5' to 3'; b) providing a second display vector polynucleotide comprising S5-display LC-S6 in the direction from 5' to 3'; c) providing a third display vector polynucleotide comprising B3-display vector fragment I-S5 in the direction from 5' to 3'; d) providing a fourth display vector polynucleotide comprising S6-display vector fragment II-B2 in the direction from 5' to 3'; e) specifically cleaving the first display vector polynucleotide, the second display vector polynucleotide, the third display vector polynucleotide and the fourth display vector polynucleotide with a restriction endonuclease to obtain a cleaved first display vector polynucleotide, a cleaved second display vector polynucleotide, a cleaved third display vector polynucleotide and a cleaved fourth display vector polynucleotide; wherein the restriction endonuclease specifically recognizes B2, B3, S5 and S6, respectively; f) mixing the cleaved first display vector polynucleotide, the cleaved second display vector polynucleotide, the cleaved third display vector polynucleotide and the cleaved fourth display vector polynucleotide so that they can be ligated directionally and cyclized to form the antigen-specific binding polypeptide gene display vector; wherein, the display VH encodes the heavy chain variable region of an antigen-specific binding polypeptide, the display LC encodes the light chain of an antigen-specific binding polypeptide; wherein the B2, B3, S5 and S6 are each independently recognition sites for the restriction endonuclease.

In some embodiments, the end produced from the specific cleavage of B2 by the restriction endonuclease that specifically recognizes it does not recognize or link to each other with the end produced from the specific cleavage of any one of the B3, S5 and S6 by the corresponding restriction endonuclease.

In some embodiments, the end produced from the specific cleavage of B3 by the restriction endonuclease that specifically recognizes it does not recognize or link to each other with the end produced from the specific cleavage of any one of the B2, S5 and S6 by the corresponding restriction endonuclease.

In some embodiments, the end produced from the specific cleavage of S5 by the restriction endonuclease that specifically recognizes it does not recognize or link to each other with the end produced from the specific cleavage of any one of the B2, B3 and S6 by the corresponding restriction endonuclease.

In some embodiments, the end produced from the specific cleavage of S6 by the restriction endonuclease that specifically recognizes it does not recognize or link to each other with the end produced from the specific cleavage of any one of the B2, B3 and S5 by the corresponding restriction endonuclease.

In some embodiments, the restriction endonuclease is selected from SfiI, Esp3I and BsmBI.

In some embodiments, the B2 and B3 can be specifically recognized and cleaved by an enzyme selected from the group consisting of: BsmBI and Esp3I.

In some embodiments, the S5 and S6 can be specifically recognized and cleaved by Sfi1.

In some embodiments, the B2 includes a nucleic acid sequence as set forth in SEQ ID NO: 8.

In some embodiments, the B3 includes a nucleic acid sequence as set forth in SEQ ID NO: 9.

In some embodiments, the S5 includes a nucleic acid sequence as set forth in SEQ ID NO: 10.

In some embodiments, the S6 includes a nucleic acid sequence as set forth in SEQ ID NO: 11.

In some embodiments, the method further includes introducing the first display vector polynucleotide into a first display bacterium to obtain a display VH component bacterial library.

In some embodiments, the method includes inserting the first display vector polynucleotide into a display component vector to form a display VH storage ligation product, and introducing the display VH storage ligation product into the first display bacterium to obtain the display VH component bacterial library.

In some embodiments, the method further includes introducing the second display vector polynucleotide into a second display bacterium to obtain a display LC component bacterial library.

In some embodiments, the method includes inserting the second display vector polynucleotide into a display component vector to form a display LC storage ligation product, and introducing the display LC storage ligation product into the second display bacterium to obtain the display LC component bacterial library.

In some embodiments, the method further includes introducing the third display vector polynucleotide into a third display bacterium to obtain a display vector component I bacterial library.

In some embodiments, the method includes inserting the third display vector polynucleotide into a display component vector to form a display vector fragment I storage ligation product, and introducing the storage ligation product into the third display bacterium to obtain the display vector component I bacterial library.

In some embodiments, the method further includes introducing the fourth display vector polynucleotide into a fourth display bacterium to obtain a display vector component II bacterial library.

In some embodiments, the method includes inserting the fourth display vector polynucleotide into a display component vector to form a display vector fragment II storage ligation product, and introducing the storage ligation product into the fourth display bacterium to obtain the display vector component II bacterial library.

In some embodiments, the display vector component vector is derived from a pUC vector.

In some embodiments, the pUC vector is a pUC19 vector or derived from a pUC19 vector.

In some embodiments, the method further includes acquiring a display VH component plasmid containing the first display vector polynucleotide from the display VH component bacterial library, and acquiring the cleaved first display vector polynucleotide from the display VH component plasmid.

In some embodiments, the method includes digesting the display VH component plasmid with a restriction endonuclease that specifically recognizes the B2 and B3, thus obtaining the cleaved first display vector polynucleotide.

In some embodiments, the method further includes acquiring a display LC component plasmid containing the second display vector polynucleotide from the display LC component bacterial library; and acquiring the cleaved second display vector polynucleotide from the display LC component plasmid.

In some embodiments, the method includes digesting the display LC component plasmid with a restriction endonuclease that specifically recognizes the S5 and S6, thus obtaining the cleaved second display vector polynucleotide.

In some embodiments, the method further includes acquiring a display fragment component plasmid I containing the third display vector polynucleotide from an expression vector component I bacterial library; and acquiring the cleaved third display vector polynucleotide from the display fragment component plasmid I.

In some embodiments, the method includes digesting the display fragment component plasmid I with a restriction endonuclease that specifically recognizes the B3 and S5, thus obtaining the cleaved third display vector polynucleotide.

In some embodiments, the method further includes acquiring a display fragment component plasmid II containing the fourth display vector polynucleotide from an expression vector component II bacterial library, and acquiring the cleaved fourth display vector polynucleotide from the display fragment component plasmid II.

In some embodiments, the method includes digesting the display fragment component plasmid II with a restriction endonuclease that specifically recognizes the S6 and B2, thus obtaining the cleaved fourth display vector polynucleotide.

In some embodiments, the method includes:

a) providing a fifth polynucleotide comprising B-antigen-specific VH-B in the direction from 5' to 3';

b) providing a VH component vector, the VH component vector includes a sixth polynucleotide comprising B3-VH component vector ligation fragment-B2 in the direction from 5' to 3';

c) cleaving the fifth polynucleotide and the VH component vector with the restriction endonuclease to obtain a cleaved fifth polynucleotide and a released sixth polynucleotide;

d) mixing the cleaved fifth polynucleotide and the released sixth polynucleotide so that they can be ligated directionally and cyclized to form an antigen-specific VH component library;

wherein the B is a recognition site for the restriction endonuclease that can specifically recognize B2 and/or B3, and the antigen-specific VH encodes the heavy chain variable region of the antigen-specific binding polypeptide.

In some embodiments, the method includes:

a) providing a seventh polynucleotide comprising S-antigen-specific LC-S in the direction from 5' to 3';

b) providing an LC component vector, the LC component vector includes an eighth polynucleotide comprising S6-LC component vector ligation fragment-S5 in the direction from 5' to 3';

c) cleaving the seventh polynucleotide and the LC component vector with the restriction endonuclease to obtain a cleaved seventh polynucleotide and a released eighth polynucleotide;

d) mixing the cleaved seventh polynucleotide and the released eighth polynucleotide so that they can be ligated directionally and cyclized to form an antigen-specific LC component library, wherein the S is a recognition site for the restriction endonuclease that can specifically recognize S5 and/or S5, and the antigen-specific LC encodes the light chain of the antigen-specific binding polypeptide.

In some embodiments, the method includes:

a) providing a ninth polynucleotide comprising B2-VH component vector tool fragment-B3 in the direction from 5' to 3';

b) inserting the ninth polynucleotide into an expression component vector to obtain the VH component vector.

In some embodiments, the method includes:

a) providing a tenth polynucleotide comprising S5-LC component vector tool fragment-S6 in the direction from 5' to 3';

b) inserting the tenth polynucleotide into the expression component vector to obtain the LC component vector.

In some embodiments, the expression component vector is derived from a pMD vector.

In some embodiments, the pMD vector is a pMD19 vector or derived from a pMD19 vector.

In some embodiments, the method includes the steps of:

a) introducing the VH component vector into a ninth bacterium to obtain a VH component vector storage bacterial library;

b) acquiring a VH component vector storage plasmid from the VH component vector storage bacterial library;

c) acquiring the released sixth polynucleotide from the VH component vector storage plasmid.

In some embodiments, the method includes digesting the VH component vector storage plasmid with the restriction endonuclease that specifically recognizes the B2 and B3, thus obtaining the released sixth polynucleotide.

In some embodiments, the method includes the steps of:

a) introducing the LC component vector into a tenth bacterium to obtain an LC component vector storage bacterial library;

b) acquiring an LC component vector storage plasmid from the LC component vector storage bacterial library;

c) acquiring the released eighth polynucleotide from the LC component vector storage plasmid.

In some embodiments, the method includes digesting the LC component vector storage plasmid with the restriction endonuclease that specifically recognizes the S5 and S6, thus obtaining the released eighth polynucleotide.

In some embodiments, the method includes:

a) providing the antigen-specific VH component library, the antigen-specific VH component library includes a first polynucleotide comprising B2-antigen-specific VH-B3 in the direction from 5' to 3';

b) providing the antigen-specific LC component library, the antigen-specific LC component library includes a second polynucleotide comprising S5-antigen-specific LC-S6 in the direction from 5' to 3';

c) providing the display vector, the display vector includes a third polynucleotide comprising B3-display vector fragment I-S5 in the direction from 5' to 3' and a fourth polynucleotide comprising S6-display vector fragment II-B2 in the direction from 5' to 3';

d) specifically cleaving the antigen-specific VH component library, the antigen-specific LC component library and the display vector with a restriction endonuclease to obtain a released first polynucleotide, a released second polynucleotide, a released third polynucleotide and a released fourth polynucleotide; wherein the restriction endonuclease specifically recognizes B2, B3, S5 and S6, respectively;

e) mixing the released first polynucleotide, the released second polynucleotide, the released third polynucleotide and the released fourth polynucleotide so that they can be ligated directionally and cyclized to form an antigen-specific binding polypeptide gene display vector;

wherein, the antigen-specific LC encodes the light chain of the antigen-specific binding polypeptide, and the antigen-specific VH encodes the heavy chain variable region of the antigen-specific binding polypeptide;

wherein the B2, B3, S5 and S6 are each independently recognition sites for the restriction endonuclease.

In some embodiments, the method includes digesting the antigen-specific VH component library with a restriction endonuclease that specifically recognizes B2 and B3, thus obtaining the released first polynucleotide.

In some embodiments, the method includes digesting the antigen-specific LC component library with a restriction endonuclease that specifically recognizes S5 and S6, thus obtaining the released second polynucleotide.

In some embodiments, the method includes digesting the display vector with a restriction endonuclease that specifically recognizes B3 and a restriction endonuclease that specifically recognizes S5, thus obtaining the released third polynucleotide.

In some embodiments, the method includes digesting the display vector with a restriction endonuclease that specifically recognizes S6 and a restriction endonuclease that specifically recognizes B2, thus obtaining the released fourth polynucleotide.

In some embodiments, the fifth polynucleotide, a seventh polynucleotide, the ninth polynucleotide, the tenth polynucleotide, the first display vector polynucleotide, the second display vector polynucleotide, the third display vector polynucleotide and/or the fourth display vector polynucleotide are obtained from sample materials.

In some embodiments, the sample materials include antibodies targeting specific antigens or antigen-binding fragments thereof and/or IgG.

In some embodiments, the antibodies or antigen-binding fragments thereof target ROR1, PD-1 and/or PD-L1.

In some embodiments, the IgG is human IgG.

In some embodiments, the human IgG is human IgG1 or human IgG2.

In some embodiments, the directional ligation involves using a ligase.

In some embodiments, the ligase includes T4 DNA ligase.

In some embodiments, the method includes introducing the antigen-specific binding polypeptide gene display vector into a cell, and acquiring an antigen-specific binding polypeptide from the cell.

In some embodiments, the method includes:

a) introducing the antigen-specific binding polypeptide gene display vector into a first bacterium to obtain an antigen-specific binding polypeptide gene display bacterial library;

b) acquiring an antigen-specific binding polypeptide display gene library from the antigen-specific binding polypeptide gene display bacterial library;

c) acquiring an antigen-specific binding polypeptide expression vector DNA from the antigen-specific binding polypeptide display gene library;

d) introducing the antigen-specific binding polypeptide expression vector DNA into a cell;

e) acquiring the antigen-specific binding polypeptide from the cell.

In some embodiments, the method includes cryopreserving the antigen-specific binding polypeptide gene display bacterial library, the VH component vector storage bacterial library, the LC component vector storage bacterial library, the display VH component bacterial library, the display LC component bacterial library, the display vector component I bacterial library and the display vector component II bacterial library.

In some embodiments, the VH component vector storage bacterial library includes at least 10 different clones.

In some embodiments, the LC component vector storage bacterial library includes at least 10 different clones.

In some embodiments, the display VH component bacterial library includes at least 10 different clones.

In some embodiments, the display LC component bacterial library includes at least 10 different clones.

In some embodiments, the display vector component I bacterial library includes at least 10 identical clones.

In some embodiments, the display vector component II bacterial library includes at least 10 identical clones.

In some embodiments, the proportion of effective clones in the antigen-specific binding polypeptide gene display bacterial library is at least about 10%.

In some embodiments, the cell is a mammalian cell.

In another aspect, the present application provides a method for screening an antigen-specific binding polypeptide or fragments thereof, which includes using the antigen-specific binding polypeptide gene display vector.

In another aspect, the present application provides an antigen-specific binding polypeptide gene display vector produced by the method.

In another aspect, the present application provides an antigen-specific binding polypeptide gene display bacterial library produced by the method.

Other aspects and advantages of the present application can be readily perceived by those skilled in the art from the following detailed description. In the following detailed description, only exemplary embodiments of the present application are shown and described. As will be recognized by those skilled in the art, the content of the present application enables those skilled in the art to make changes to the disclosed specific embodiments without departing from the spirit and scope of the invention involved in the present application. Correspondingly, the drawings and description in the specification of the present application are merely exemplary, rather than restrictive.

BRIEF DESCRIPTION OF THE DRAWINGS

The specific features of the invention involved in the present application are as shown in the appended claims. The characteristics and advantages of the invention involved in the present application can be better understood by referring to the exemplary embodiments described in detail below and the accompanying drawings. A brief description of the drawings is as below:

DETAILED DESCRIPTION OF THE EMBODIMENTS

Figure 1:
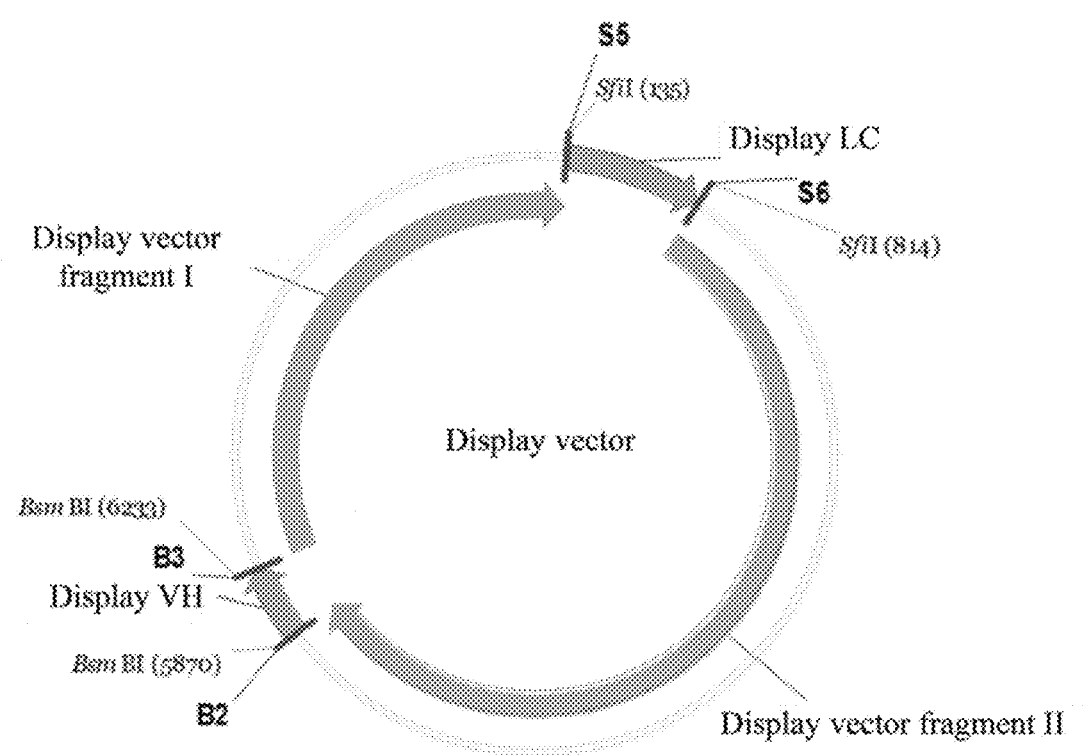
FIG. 1 shows the structure of the display vector of the present application.

The implementation of the present application will be illustrated below by specific examples, and other advantages and effects of the present application will be easily known by those familiar with the art from the contents disclosed in the specification.

Definition of Terms

In the present application, the term "antigen-binding polypeptide" generally refers to a polypeptide molecule capable of specifically recognizing and/or neutralizing specific antigens. This term can include an antibody or an antigen-binding moiety thereof, or an antigen-binding region and/or an antibody variable region of an intact antibody. A basic 4-chain antibody unit is a heterotetrameric glycoprotein composed of two identical light chains and two identical heavy chains. In the case of IgG, each L chain is linked to the H chain through a covalent disulfide bond, while two H chains are linked to each other through one or more disulfide bonds whose number depends on the isotype of the H chain. Each H and L chain also has regularly spaced intra-chain disulfide bonds. Each H chain has a variable domain (VH) at the N-terminus, which is followed by three (for each of a and y chains) or four (for and F isotypes) constant domains (CHs). The antigen-binding polypeptide can be obtained by chemical methods and/or genetic engineering methods. For example, the antibodies can be digested by using protease, including pepsin and papain, to produce the antigen-binding fragments. In the present application, the antibody fragments may be Fab.

In the present application, the term "Fab" generally refers to two identical antigen-binding fragments produced by digesting an antibody with an intact structure (e.g., with the Fc and hinge regions removed) by papain. Fab can be composed of an intact light chain, a heavy chain variable region (VH) and the first constant domain of a heavy chain (CH1). Each Fab can have a single antigen-binding site.

In the present application, the term "the first polynucleotide" generally refers to a polynucleotide comprising an antigen-specific VH, which may have recognition sites for endonucleases (e.g., restriction endonucleases) at the 5'-end and/or 3'-end. For example, the first polynucleotide can include B2-antigen-specific VH-B3 in the direction from 5' to 3', wherein the B2, B3 may be recognition sites for the restriction endonuclease. For example, after being digested with an endonuclease that recognizes an endonuclease recognition site in the first polynucleotide (e.g., a restriction endonuclease that recognizes B2 and B3, such as BsmBI), the released first polynucleotide may comprise the antigen-specific VH, and the two ends of the antigen-specific VH may also have sticky ends of the specific sequence after cleavage.

In the present application, the term "the second polynucleotide" generally refers to polynucleotide comprising an antigen-specific LC, which may have recognition sites for endonucleases (e.g., restriction endonucleases) at the 5'-end and/or 3'-end. For example, the second polynucleotide can include S5-antigen-specific LC-S6 in the direction from 5' to 3', wherein the S5, S6 may be recognition sites for the restriction endonuclease. For example, after being digested with an endonuclease that recognizes an endonuclease recognition site in the first polynucleotide (e.g., a restriction endonuclease that recognizes S5 and S6, such as SfiI), the released second polynucleotide can include the antigen-specific LC, which can also have sticky ends of the specific sequence after cleavage at its two ends.

In the present application, the term "antigen-specific VH" generally refers to a nucleotide encoding the heavy chain variable region of an antibody capable of specifically binding to an antigen, and the term "antigen-specific LC" generally refers to a nucleotide encoding the light chain of an antibody capable of specifically binding to an antigen. The sequences of the antigen-specific VH and the antigen-specific LC can be obtained by any methods known in the art, including, but not limited to, phage display technology, yeast surface display technology, ribosome display technology, mRNA display technology and/or hybridoma technology. For example, they can be obtained through the phage library display method.

In the present application, the term "the third polynucleotide" generally refers to a polynucleotide comprising the display vector fragment I, which can have recognition sites for an endonuclease (e.g., a restriction endonuclease) at the 5'-end and/or 3'-end. For example, the third polynucleotide can include B3-display vector fragment I-S5 in the direction from 5' to 3', wherein the B3, S5 may be recognition sites for the restriction endonuclease. The third polynucleotide may be included in a display vector. After being digested with an endonuclease that recognizes the endonuclease recognition sites in the third polynucleotide (e.g., a restriction endonuclease that recognizes B3 and S5, such as SfiI, BsmBI and/or Esp3I), the third polynucleotide can be released. The released third polynucleotide can include the display vector fragment I, which can also have sticky ends of the specific sequence after cleavage at its two ends.

In the present application, the term "the released third polynucleotide" generally refers to the fragment of the third polynucleotide released after being treated with the display vector. In the present application, the treatment may be digestion with the restriction endonuclease. For example, suitable restriction endonucleases (e.g., SfiI, BsmBI and/or Esp3I) can be selected for the recognition sites for the restriction endonuclease on the display vector such that the released third polynucleotide can be released from the display vector and isolated.

In the present application, the term "the fourth polynucleotide" generally refers to a polynucleotide comprising the display vector fragment II, which can have recognition sites for an endonuclease (e.g., a restriction endonuclease) at the 5'-end and/or 3'-end. For example, the fourth polynucleotide can include S6-display vector fragment II-B2 in the direction from 5' to 3', wherein the S6, B2 may be recognition sites for the restriction endonuclease. The fourth polynucleotide may be included in a display vector. After being digested with an endonuclease that recognizes the endonuclease recognition sites in the fourth polynucleotide (e.g., a restriction endonuclease that recognizes S6 and B2, such as SfiI, BsmBI and/or Esp3I), the fourth polynucleotide can be released. The released fourth polynucleotide can include the display vector fragment II, which can also have sticky ends of the specific sequence after cleavage at its two ends.

In the present application, the term "the released fourth polynucleotide" generally refers to the fragment of the fourth polynucleotide released after being treated with the display vector. In the present application, the treatment may be digestion with the restriction endonuclease. For example, suitable restriction endonucleases (e.g., SfiI, BsmBI and/or Esp3I) can be selected for the recognition sites for the restriction endonuclease on the display vector such that the released fourth polynucleotide can be released from the display vector and isolated.

In the present application, the term "the fifth polynucleotide" generally refers to a polynucleotide comprising the antigen-specific VH, which can have recognition sites for an endonuclease (e.g., a restriction endonuclease) at the 5'-end and/or 3'-end. For example, the fifth polynucleotide can include B-the antigen-specific VH-B in the direction from 5' to 3', wherein the B may be a recognition site for the restriction endonuclease, and the restriction endonuclease may be a restriction endonuclease capable of recognizing B2 and/or B3. After being digested with an endonuclease that recognizes the endonuclease recognition sites in the fifth polynucleotide (e.g., a restriction endonuclease that recognizes B, such as BsmBI and/or Esp3I), the cleaved fifth polynucleotide can include the antigen-specific VH.

In the present application, the term "the seventh polynucleotide" generally refers to a polynucleotide comprising the antigen-specific LC, which can have recognition sites for an endonuclease (e.g., a restriction endonuclease) at the 5'-end and/or 3'-end. For example, the seventh polynucleotide can include S-the antigen-specific LC-S in the direction from 5' to 3', wherein the S may be a recognition site for the restriction endonuclease, and the restriction endonuclease may be a restriction endonuclease capable of recognizing S5 and/or S6. After being digested with an endonuclease that recognizes the endonuclease recognition sites in the seventh polynucleotide (e.g., a restriction endonuclease that recognizes S, such as SfiI), the cleaved seventh polynucleotide can include the antigen-specific LC.

In the present application, the term "VH component vector" generally refers to a cyclic polynucleotide comprising the sixth polynucleotide and/or a VH component vector tool fragment.

In the present application, the term "LC component vector" generally refers to a cyclic polynucleotide comprising the eighth polynucleotide and/or an LC component vector tool fragment.

In the present application, the term "display vector" generally refers to a cyclic polynucleotide comprising a display vector fragment I and a display vector fragment II, which may further include a display VH and a display LC. After being treated, the display vector can release a first display vector polynucleotide, a second display vector polynucleotide, a third display vector polynucleotide and/or a fourth display vector polynucleotide.

In the present application, the term "the first display vector polynucleotide" generally refers to a polynucleotide comprising a display VH, which can have recognition sites for an endonuclease (e.g., a restriction endonuclease) at the 5'-end and/or 3'-end. For example, the first display vector polynucleotide can include B2-display VH-B3 in the direction from 5' to 3', wherein the B2, B3 may be recognition sites for the restriction endonuclease. For example, after being digested with an endonuclease that recognizes the endonuclease recognition sites in the first display vector polynucleotide (e.g., a restriction endonuclease that recognizes B2 and B3, such as BsmBI), the cleaved first display vector polynucleotide can include the display VH, which can also have sticky ends of the specific sequence after cleavage at its two ends.

In the present application, the term "the second display vector polynucleotide" generally refers to a polynucleotide comprising a display LC, which can have recognition sites for an endonuclease (e.g., a restriction endonuclease) at the 5'-end and/or 3'-end. For example, the second display vector polynucleotide can include S5-display LC-S6 in the direction from 5' to 3', wherein the S5, S6 may be recognition sites for the restriction endonuclease. For example, after being digested with an endonuclease that recognizes the endonuclease recognition sites in the second display vector polynucleotide (e.g., a restriction endonuclease that recognizes S5 and S6, such as SfiI), the cleaved second display vector polynucleotide can include the display LC, which can also have sticky ends of the specific sequence after cleavage at its two ends.

In the present application, the term "display VH" generally refers to a nucleotide encoding the heavy chain variable region of an antigen-binding polypeptide, and the term "display LC" generally refers to a nucleotide encoding the light chain of an antigen-binding polypeptide. The "display VH" and "antigen-specific VH" in the present application may be nucleotides encoding heavy chain variable regions derived from binding polypeptides directed against the same antigen, and may also be nucleotides encoding heavy chain variable regions derived from binding polypeptides directed against different antigens. The "display LC" and "antigen-specific LC" in the present application may be nucleotides encoding light chains derived from binding polypeptides directed against the same antigen, and may also be nucleotides encoding light chains derived from binding polypeptides directed against different antigens.

In the present application, the term "display vector fragments" generally refers to fragments obtained by cleavage of the display vector using restriction endonucleases (e.g., BsmBI and/or SfiI), such as the display vector fragment I and the display vector fragment II. The 5'-end and 3'-end of the display vector fragments can include recognition sites for restriction endonucleases.

In the present application, the term "the third display vector polynucleotide" generally refers to a polynucleotide comprising the display vector fragment I, which can have recognition sites for an endonuclease (e.g., a restriction endonuclease) at the 5'-end and/or 3'-end. For example, the third display vector polynucleotide can include B3-display vector fragment I-S5 in the direction from 5' to 3', wherein the B3, S5 may be recognition sites for the restriction endonuclease. For example, after being digested with an endonuclease that recognizes the endonuclease recognition sites in the third display vector polynucleotide (e.g., a restriction endonuclease that recognizes S5, such as SfiI, or a restriction endonuclease that recognizes B3, such as BsmBI and/or Esp3I), the cleaved third display vector polynucleotide can include the display vector fragment I, which can also have sticky ends of the specific sequence after cleavage at its two ends.

In the present application, the term "the fourth display vector polynucleotide" generally refers to a polynucleotide comprising the display vector fragment II, which can have recognition sites for an endonuclease (e.g., a restriction endonuclease) at the 5'-end and/or 3'-end. For example, the fourth display vector polynucleotide can include S6-display vector fragment II-B2 in the direction from 5' to 3', wherein the S6, B2 may be recognition sites for the restriction endonuclease. For example, after being digested with an endonuclease that recognizes the endonuclease recognition sites in the fourth display vector polynucleotide (e.g., a restriction endonuclease that recognizes S6, such as SfiI, or a restriction endonuclease that recognizes B2, such as BsmBI and/or Esp3I), the cleaved fourth display vector polynucleotide can include the display vector fragment II, which can also have sticky ends of the specific sequence after cleavage at its two ends.

In the present application, the term "VH component vector" generally refers to a cyclic polynucleotide formed by inserting the ninth polynucleotide into an expression component vector.

In the present application, the term "LC component vector" generally refers to a cyclic polynucleotide formed by inserting the tenth polynucleotide into an expression component vector.

In the present application, the term "expression component vector" generally refers to a vector into which polynucleotides (e.g., the ninth polynucleotide and/or the tenth polynucleotide) can be inserted. The expression component vector may be derived from a pMD vector. For example, the expression component vector may be a pMD19 vector or derived from a pMD19 vector.

In the present application, the term "the ninth polynucleotide" generally refers to a polynucleotide comprising the VH component vector tool fragment, which can have recognition sites for an endonuclease (e.g., a restriction endonuclease) at the 5'-end and/or 3'-end. For example, the ninth polynucleotide can include B2-VH component vector tool fragment-B3 in the direction from 5' to 3', wherein the B2, B3 may be recognition sites for the restriction endonuclease.

In the present application, the term "the tenth polynucleotide" generally refers to a polynucleotide comprising the LC component vector tool fragment, which can have recognition sites for an endonuclease (e.g., a restriction endonuclease) at the 5'-end and/or 3'-end. For example, the tenth polynucleotide can include S5-LC component vector tool fragment-S6 in the direction from 5' to 3', wherein the S5, S6 may be recognition sites for the restriction endonuclease.

In the present application, the term "component vector tool fragment" generally refers to any polynucleotide that may have recognition sites for an endonuclease (e.g., a restriction endonuclease) at the 5'-end and/or 3'-end, but no recognition sites for an endonuclease (e.g., a restriction endonuclease) within it. The length of the component vector tool fragment is usually different from those of the antigen-specific VH and the antigen-specific LC. In some cases, the length of the component vector tool fragment may be about 1 kb. In some cases, the component vector tool fragment may be derived from Fc region of IgG. For example, the component vector tool fragment may be derived from a Fc region selected from a group consisting of human IgG1 and human IgG2. For example, the recognition sites for the endonuclease (e.g., a restriction endonuclease) may be B2 and B3. For another example, the recognition sites for the endonuclease (e.g., a restriction endonuclease) may be S5 and S6.

In the present application, the term "component vector" generally refers to a cyclic polynucleotide formed by inserting the ninth polynucleotide and/or the tenth polynucleotide into an expression component vector.

In the present application, the term "the ninth bacterium" generally refers to a bacterium for introducing or comprising the ninth nucleotide. The ninth bacterium can include the VH component vector. In the present application, the ninth bacterium can express, replicate and/or store (e.g., cryopreserve) the ninth nucleotide and/or the VH component vector. In the present application, a VH component vector storage plasmid comprising the VH component vector can be obtained from the ninth bacterium.

In the present application, the term "the tenth bacterium" generally refers to a bacterium for introducing or comprising the tenth nucleotide. The tenth bacterium can include the LC component vector. In the present application, the tenth bacterium can express, replicate and/or store (e.g., cryopreserve) the tenth nucleotide and/or the LC component vector. In the present application, an LC component vector storage plasmid comprising the LC component vector can be obtained from the tenth bacterium.

In the present application, the term "the sixth polynucleotide" generally refers to a polynucleotide comprising the VH component vector ligation fragment, which can have recognition sites for an endonuclease (e.g., a restriction endonuclease) at the 5'-end and/or 3'-end. For example, the sixth polynucleotide can include B3-VH component vector ligation fragment-B2 in the direction from 5' to 3', wherein the B3, B2 may be recognition sites for the restriction endonuclease. The sixth polynucleotide can be included in the VH component vector. After being digested with an endonuclease that recognizes the endonuclease recognition sites in the sixth polynucleotide (e.g., a restriction endonuclease that recognizes B3 and B2, such as BsmBI and/or Esp3I), the sixth polynucleotide can be released. The released sixth polynucleotide can include the antigen-specific VH, which can also have sticky ends of the specific sequence after cleavage at its two ends.

In the present application, the term "the released sixth polynucleotide" generally refers to a fragment of the sixth polynucleotide released after being treated with the VH component vector. In the present application, the treatment may be digestion with the restriction endonuclease. For example, suitable restriction endonucleases (e.g., BsmBI and/or Esp3I) can be selected for the recognition sites for the restriction endonuclease on the VH component vector such that the released sixth polynucleotide can be released from the VH component vector and isolated.

In the present application, the term "the eighth polynucleotide" generally refers to a polynucleotide comprising the LC component vector ligation fragment, which can have recognition sites for an endonuclease (e.g., a restriction endonuclease) at the 5'-end and/or 3'-end. For example, the eighth polynucleotide can include S6-LC component vector ligation fragment-S5 in the direction from 5' to 3', wherein the S6, S5 may be recognition sites for the restriction endonuclease. The eighth polynucleotide can be included the LC component vector. After being digested with an endonuclease that recognizes the endonuclease recognition sites in the eighth polynucleotide (e.g., a restriction endonuclease that recognizes S6 and S5, such as SfiI), the eighth polynucleotide can be released. The released eighth polynucleotide can include the antigen-specific LC, which can also have sticky ends of the specific sequence after cleavage at its two ends.

In the present application, the term "the released eighth polynucleotide" generally refers to a fragment of the eighth polynucleotide released after being treated with the LC component vector. In the present application, the treatment may be digestion with the restriction endonuclease. For example, suitable restriction endonucleases (e.g., SfiI) can be selected for the recognition sites for the restriction endonuclease on the LC component vector such that the released eighth polynucleotide can be released from the LC component vector and isolated.

In the present application, the term "restriction endonuclease" generally refers to an enzyme the cleaves double-stranded DNA. The restriction endonuclease can produce sticky ends with protruding single-stranded DNA that can bind to DNA ligase. In the present application, the restriction endonuclease can have the effects of recognition and restriction cleavage. For example, the cleavage site for the restriction endonuclease is at a certain distance from its recognition site. For example, the restriction endonuclease may be selected from SfiI, BsmBI and Esp3I.

In the present application, the term "the first bacterium" generally refers to a bacterium for introducing or comprising the antigen-specific binding polypeptide gene display vector. The first bacterium can include the antigen-specific VH, the antigen-specific LC, the display vector fragment I and the display vector fragment II. In the present application, the first bacterium can express, replicate and/or store (e.g., cryopreserve) the antigen-specific VH, the antigen-specific LC, the display vector fragment I and the display vector fragment II, or the antigen-specific binding polypeptide expression vector DNA.

In the present application, the term "antigen-specific binding polypeptide gene display bacterial library" generally refers to a bacterial library obtained by introducing the antigen-specific binding polypeptide gene display vector into the first bacterium. In the present application, the antigen-specific binding polypeptide gene display bacterial library may be a bacterial library comprising a nucleic acid sequence encoding the light chain of the antigen-specific binding polypeptide or the heavy chain variable region of the antigen-specific polypeptide. In the present application, the antigen-specific binding polypeptide gene display bacterial library can include about $10^5$ to about $10^9$ (for example, it can include about $10^5$ to about $10^8$, about $10^5$ to about $10^7$, about $10^6$ to about $10^7$) of nucleic acid sequences encoding the antigen-specific binding polypeptide. In the present application, the antigen-specific binding polypeptide gene display bacterial library can include about $10^7$ to about $10^{12}$ (for example, it can include about $10^7$ to about $10^{11}$, about $10^7$ to about $10^{10}$, about $10^7$ to about $10^9$, about $10^7$ to about $10^8$) of the first bacteria.

In the present application, the term "the first display bacterium" generally refers to a bacterium for introducing or comprising the first display vector polynucleotide. The first bacterium can include the display VH. In the present application, the first display bacterium can express, replicate and/or store (e.g., cryopreserve) the display VH, and/or the first display vector polynucleotide.

In the present application, the term "the display VH component bacterial library" generally refers to a bacterial library obtained by introducing the first display vector polynucleotide into the first display bacterium. In the present application, the display VH component bacterial library may be a bacterial library comprising a nucleic acid sequence encoding the heavy chain variable region of the antigen-specific polypeptide. In the present application, the display VH component bacterial library can include about $10^5$ to about $10^9$ (for example, it can include about $10^5$ to about $10^8$, about $10^5$ to about $10^7$, about $10^6$ to about $10^7$) of nucleic acid sequences encoding the display VH. In the present application, the display VH component bacterial library can include about $10^7$ to about $10^{12}$ (for example, it can include about $10^7$ to about $10^{11}$, about $10^7$ to about $10^{10}$, about $10^7$ to about $10^9$, about $10^7$ to about $10^8$) of the first display bacteria.

In the present application, the term "the second display bacterium" generally refers to a bacterium for introducing or comprising the second display vector polynucleotide. The second bacterium can include the display LC. In the present application, the second display bacterium can express, replicate and/or store (e.g., cryopreserve) the display LC, and/or the second display vector polynucleotide.

In the present application, the term "the display LC component bacterial library" generally refers to a bacterial library obtained by introducing the second display vector polynucleotide into the second display bacterium. In the present application, the display LC component bacterial library may be a bacterial library comprising a nucleic acid sequence encoding the light chain of the antigen-specific polypeptide. In the present application, the display LC component bacterial library can include about $10^5$ to about $10^9$ (for example, it can include about $10^5$ to about $10^8$, about $10^5$ to about $10^7$, about $10^6$ to about $10^7$) of nucleic acid sequences encoding the display LC. In the present application, the display LC component bacterial library can include about $10^7$ to about $10^{12}$ (for example, it can include about $10^7$ to about $10^{11}$, about $10^7$ to about $10^{10}$, about $10^7$ to about $10^9$, about $10^7$ to about $10^8$) of the second display bacteria.

In the present application, the term "the third display bacterium" generally refers to a bacterium for introducing or comprising the third display vector polynucleotide. The third bacterium can include the display vector fragment I. In the present application, the third display bacterium can express, replicate and/or store (e.g., cryopreserve) the display vector fragment I, and/or the third display vector polynucleotide.

In the present application, the term "the display vector component I bacterial library" generally refers to a bacterial library obtained by introducing the third display vector polynucleotide into the third display bacterium. In the present application, the display vector component I bacterial library may be a bacterial library comprising a nucleic acid sequence encoding the display vector component I. In the present application, the display vector component I bacterial library can include about $10^5$ to about $10^9$ (for example, it can include about $10^5$ to about $10^8$, about $10^5$ to about $10^7$, about $10^6$ to about $10^7$) of nucleic acid sequences encoding the display LC. In the present application, the display vector component I bacterial library can include about $10^7$ to about $10^{12}$ (for example, it can include about $10^7$ to about $10^{11}$, about $10^7$ to about $10^{10}$, about $10^7$ to about $10^9$, about $10^7$ to about $10^8$) of the third display bacteria.

In the present application, the term "the fourth display bacterium" generally refers to a bacterium for introducing or comprising the fourth display vector polynucleotide. The fourth bacterium can include the display vector fragment II. In the present application, the fourth display bacterium can express, replicate and/or store (e.g., cryopreserve) the display vector fragment II, and/or the fourth display vector polynucleotide.

In the present application, the term "the display vector component II bacterial library" generally refers to a bacterial library obtained by introducing the fourth display vector polynucleotide into the fourth display bacterium. In the present application, the display vector component II bacterial library may be a bacterial library comprising a nucleic acid sequence encoding the display vector component II. In the present application, the display vector component II bacterial library can include about $10^5$ to about $10^9$ (for example, it can include about $10^5$ to about $10^8$, about $10^5$ to about $10^7$, about $10^6$ to about $10^7$) of nucleic acid sequences encoding the display LC. In the present application, the display vector component II bacterial library can include about $10^7$ to about $10^{12}$ (for example, it can include about $10^7$ to about $10^{11}$, about $10^7$ to about $10^{10}$, about $10^7$ to about $10^9$, about $10^7$ to about $10^8$) of the fourth display bacteria.

In the present application, the term "introduction" generally refers to a process of transferring or introducing an exogenous polynucleotide into a cell. The cell may be a host cell. The introduced cell includes the primary cells of the subject and their progeny. The cell may be a prokaryotic cell, for example, it may be a bacterial cell.

In the present application, the term "ligation" generally refers to ligating two or more polynucleotide molecules together. For example, the ligation can be achieved by ligase (e.g., DNA ligase). For example, the 3'-end of one polynucleotide is ligated to the 5'-end of another polynucleotide to form an intact polynucleotide molecule.

In the present application, the term "clones" generally refers to the number of colonies. For example, the clones may be the number of colonies in the bacterial library (e.g., the light chain component bacterial library, the heavy chain component bacterial library, the display bacterial library and/or the phage library). In some cases, the clones may be the number of different colonies in the bacterial library. In some cases, the clones may be the number of progeny populations produced by a single clone.

In the present application, the terms "polynucleotide", "nucleotide", "nucleotide sequence", "nucleic acid" and "oligonucleotide" can be used interchangeably, and generally refer to a polymeric form of nucleotides of any length, such as deoxyribonucleotide or ribonucleotide, or analogues thereof, including, for example, 200, 300, 500, 1000, 2000, 3000, 5000, 7000, 10,000, 100,000, etc. The polynucleotide may contain phosphodiester bonds.

In the present application, the term "and/or" should be understood to mean either or both of the alternatives.

In the present application, the term "comprise" generally refers to the inclusion of explicitly specified features, but not excluding other elements.

In the present application, the term "about" generally refers to varying within a range of 0.5%-10% above or below the specified value, for example, varying within a range of 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, or 10% above or below the specified value.

DETAILED DESCRIPTION

In one aspect, the present application provides a method for constructing an antigen-specific binding polypeptide gene display vector.

The antigen-specific binding polypeptide gene display vector of the present application can be composed of four fragments linked by directional cyclization, which can respectively include an antigen-specific VH, an antigen-specific LC, a display vector fragment I and a display vector fragment II.

Component Vector

The method of the present application can include constructing a component vector, which can include providing polynucleotides, e.g., the ninth polynucleotide and the tenth polynucleotide. The ninth polynucleotide can include B2-VH component vector tool fragment-B3 in the direction from 5' to 3', and the tenth polynucleotide includes S5-LC component vector tool fragment-S6 in the direction from 5' to 3'. The vector tool fragment can be derived from the Fc fragment of IgG. For example, the Fc fragment of human IgG1. For another example, the Fc fragment of human IgG2. In some cases, the ninth nucleotide can be obtained by amplification using DDB214 and DDB215 as primers and the Fc fragment of human IgG1 as a template, wherein the DDB214 can include an amino acid sequence as set forth in SEQ ID NO: 1, and the DDB215 can include an amino acid sequence as set forth in SEQ ID NO: 2. In some cases, the tenth nucleotide can be obtained by amplification using DDB216 and DDB217 as primers and the Fc fragment of human IgG1 as a template, wherein the DDB216 can include an amino acid sequence as set forth in SEQ ID NO: 3, and the DDB217 can include an amino acid sequence as set forth in SEQ ID NO: 4. The ninth nucleotide can include the recognition sites B2 and B3 of the restriction endonuclease at its two ends, and the tenth nucleotide can include recognition sites S5 and S6 of the restriction endonuclease at its two ends.

The method can include inserting the polynucleotides (e.g., the ninth polynucleotide and the tenth polynucleotide)

into an expression component vector to obtain a component vector (e.g., the VH component vector and the LC component vector).

The expression component vector can be derived from any vector, for example, any vector that can be amplified and/or easily preserved. In some cases, the vector used as the expression component vector may have properties such as high copy number, small molecular weight, etc. In some cases, the expression component vector may be derived from a pMD vector. For example, the expression component vector may be a pMD19 vector or derived from a pMD19 vector.

In the present application, for the purpose of constructing the expression component vector, the pMD vector or the vector derived from pMD can be engineered/modified. For example, one or more recognition sites for an endonuclease in the vector can be removed through site-directed mutagenesis (for example, removing one or more recognition sites for BsmBI and/or SfiI therein). In some cases, one or more recognition sites for an endonuclease can also be added in the vector through site-directed mutagenesis (for example, adding one or more recognition sites for BsmBI and/or SfiI at selected locations).

For example, by means of site-directed mutagenesis, one or more recognition sites for BsmBI originally contained in the vector can be removed, and one or more additional recognition sites for BsmBI can be then added at another location in the vector, so as to obtain a modified vector (e.g., a modified pMD vector).

In the present application, the expression component vector (e.g., the expression component vector of the VH component vector) can include a recognition site for BsmBI. In some cases, the expression component vector can include two recognition sites for BsmBI.

For another example, by means of site-directed mutagenesis, one or more recognition sites for SfiI originally contained in the vector can be removed, and one or more additional recognition sites for SfiI can be then added at another location in the vector, so as to obtain a modified vector (e.g., a modified pMD vector).

In the present application, the expression component vector (e.g., the expression component vector of the LC component vector) can include a recognition site for SfiI. In some cases, the expression component vector can include two recognition sites for SfiI.

In some cases, the method may further include inserting the polynucleotides (e.g., the ninth polynucleotide and the tenth polynucleotide) into an expression component vector to obtain a component vector storage plasmid (e.g., a VH component vector storage plasmid and a LC component vector storage plasmid), and then introducing the component vector storage plasmid into bacteria (e.g., the ninth bacterium and the tenth bacterium) to obtain a component vector storage bacterial library (e.g., a VH component vector storage bacterial library and a LC component vector storage bacterial library).

Figure 3:
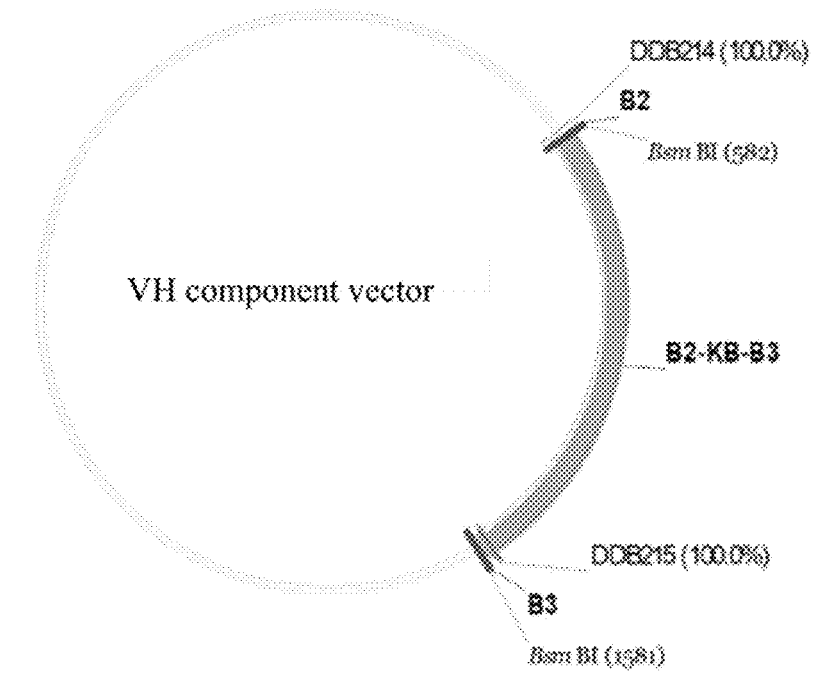
FIG. 3 shows the structure of the VH component vector of the present application.

For example, the VH component vector of the present application is shown in FIG. 3, which can be obtained through ligation by inserting the ninth polynucleotide into an expression component vector. The VH component vector includes a sixth polynucleotide which can include B3-VH component vector ligation fragment-B2 in the direction from 5' to 3', wherein B2 and B3 can be specifically recognized and cleaved by BsmBI and/or Esp3I, respectively. For example, the B2 can include a nucleic acid sequence as set forth in SEQ ID NO: 8, and the B3 can include a nucleic acid sequence as set forth in SEQ ID NO: 9.

After being treated (e.g., digestion), the VH component vector can produce a released sixth polynucleotide which can have sticky ends of the specific sequence produced after cleavage at its 5' and 3'-ends.

Figure 4:
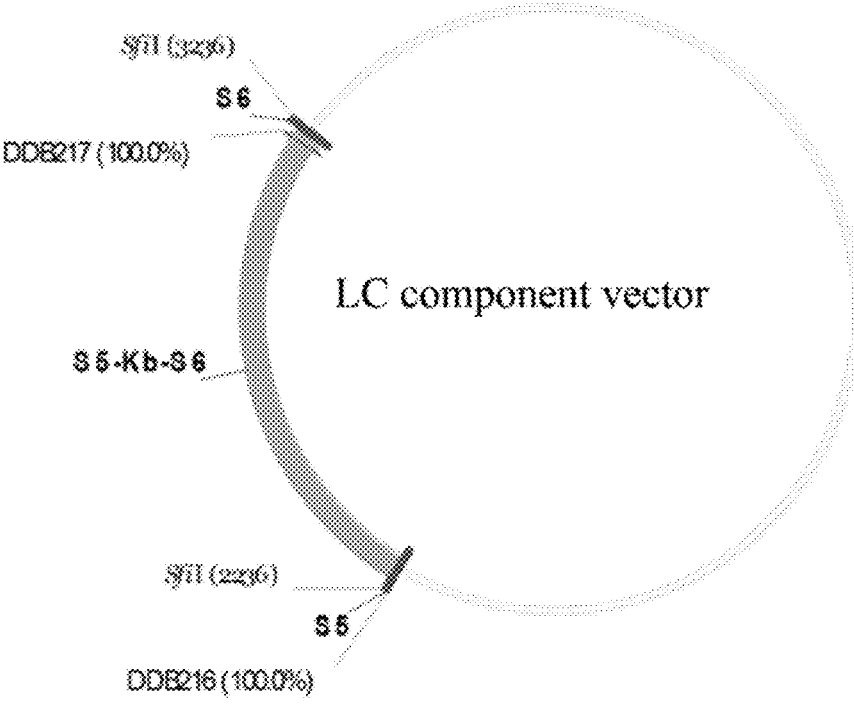
FIG. 4 shows the structure of the LC component vector of the present application.

For example, the LC component vector of the present application is shown in FIG. 4, which can be obtained through ligation by inserting the tenth polynucleotide into an expression component vector. The LC component vector includes an eighth polynucleotide which can include S6-LC component vector ligation fragment-S5 in the direction from 5' to 3', wherein S6 and S5 can be specifically recognized and cleaved by SfiI respectively. For example, the S6 can include a nucleic acid sequence as set forth in SEQ ID NO: 11, and the S5 can include a nucleic acid sequence as set forth in SEQ ID NO: 10.

After being treated (e.g., digestion), the LC component vector can produce a released eighth polynucleotide which can have sticky ends of the specific sequence produced after cleavage at its 5' and 3'-ends.

Antigen-Specific VH and Antigen-Specific LC

The method of the present application includes providing a fifth polynucleotide comprising B-antigen-specific VH-B in the direction from 5' to 3', wherein the B is a recognition site for the restriction endonuclease that can specifically recognize B2 and/or B3. For example, the antigen-specific VH can be amplified using the antigen-specific VH fragment as a template such that the 5' and 3' ends of the antigen-specific VH are attached to the recognition sites for the restriction endonuclease (e.g., BsmBI and/or Esp3I).

The method of the present application includes providing a seventh polynucleotide comprising S-antigen-specific LC-S in the direction from 5' to 3', wherein the S is a recognition site for the restriction endonuclease that can specifically recognize S5 and/or S6. For example, the antigen-specific LC can be amplified using the antigen-specific LC fragment as a template such that the 5' and 3' ends of the antigen-specific LC are attached to the recognition sites for restriction endonuclease (e.g., SfiI).

In some cases, the antigen-specific VH fragment and the antigen-specific LC fragment can be obtained by methods in the prior art. For example, they can be obtained from animals immunized with antigens, and can also be obtained from antibody libraries, including a combinatorial antibody library, a phage display library, a yeast surface display library, a ribosome display library, an mRNA display library.

Component Library

The method of the present application can include cleaving the fifth polynucleotide and the VH component vector with the restriction endonuclease to obtain the cleaved fifth polynucleotide and the released sixth polynucleotide, and then mixing the cleaved fifth polynucleotide and the released sixth polynucleotide so that they can be ligated directionally and cyclized to form an antigen-specific VH component library.

The antigen-specific VH component library can include the antigen-specific VH. After cleaving the antigen-specific VH component library with a restriction endonuclease (e.g., the restriction endonuclease that recognizes B2 and B3), the released antigen-specific VH can be obtained, of which the 5' and 3' ends can have sticky ends of a specific sequence.

The method of the present application can include cleaving the seventh polynucleotide and the LC component vector with the restriction endonuclease to obtain a cleaved seventh polynucleotide and a released eighth polynucleotide, and then mixing the cleaved seventh polynucleotide and the released eighth polynucleotide so that they can be ligated directionally and cyclized to form an antigen-specific LC component library.

The antigen-specific LC component library can include the antigen-specific LC. After cleaving the antigen-specific LC component library with a restriction endonuclease (e.g., the restriction endonuclease that recognizes S5 and S6), the released antigen-specific LC can be obtained, of which the 5' and 3' ends can have sticky ends of a specific sequence.

Display Vector

The method of the present application can also include constructing a display vector which can be composed of four display vector polynucleotides (e.g., the first display vector polynucleotide, the second display vector polynucleotide, the third display vector polynucleotide and the fourth display vector polynucleotide).

The display vector polynucleotides of the present application (the first display vector polynucleotide, the second display vector polynucleotide, the third display vector polynucleotide and the fourth display vector polynucleotide) can include antigen-binding polypeptides or fragments thereof, such as the display LC and/or the display VH. In the present application, the display LC can encode the light chain of the antigen-binding polypeptide, the display VH can encode heavy chain variable region of the antigen-binding polypeptide, and the light chain can bind to the heavy chain variable region to form a Fab that recognizes a target. In some cases, the target may be an antigen. For example, the target is PD-1.

The display vector polynucleotides of the present application (e.g., the first display vector polynucleotide, the second display vector polynucleotide, the third display vector polynucleotide and the fourth display vector polynucleotide) can include display vector fragments, such as the display vector fragment I and the display vector fragment II. The desired length or type of the display vector fragment I and the display vector fragment II can be selected respectively according to the length or nature of the antigen-binding polypeptide or fragments thereof to be expressed, and the length or nature of the restriction sites.

In some cases, the display vector fragment I and the display vector fragment II may be derived from any one vector fragment capable of expressing the target gene. For example, the expression vector fragment I and the expression vector fragment II may be derived from the fragments of the display vector pDGB4 (with regard to pDGB4, see Ivan Zhou, et al., "Four-way ligation for construction of a mammalian cell-based full-length antibody display library", Acta Biochim Biophys Sin 2011, 43: 232-238).

The display vector fragments of the present application (e.g., the display vector fragment I and the display vector fragment II) can include nucleotide sequences with specific functions, including, but not limited to, promoters, enhancers, signal peptides, screening markers (for example, they may include enzyme recognition sites, resistance genes, reporter genes, and screening genes), which can be adjusted in the display vector fragments by those skilled in the art according to the desired function (inserting/substituting and/or deleting the above nucleotide sequences with specific functions). In some cases, the display vector fragments can be adjusted in different cases to get different nucleotide sequences.

In the present application, the first display vector polynucleotide can include B2-display VH-B3 in the direction from 5' to 3', wherein, B2 and B3 can be each independently recognition sites for the restriction endonuclease, and the display VH can encode the heavy chain variable region of the antigen-binding polypeptide. In some cases, the B2 and B3 can be specifically recognized and cleaved by BsmBI, respectively. For example, the B2 can include a nucleic acid sequence as set forth in SEQ ID NO: 8, and the B3 can include a nucleic acid sequence as set forth in SEQ ID NO: 9.

The second display vector polynucleotide can include S5-display LC-S6 in the direction from 5' to 3', wherein, S5 and S6 can be each independently recognition sites for the restriction endonuclease, and the display LC can encode the light chain of the antigen-binding polypeptide. In some cases, the S5 and S6 can be specifically recognized and cleaved by SfiI, respectively. For example, the S5 can include a nucleic acid sequence as set forth in SEQ ID NO: 10, and the S6 can include a nucleic acid sequence as set forth in SEQ ID NO: 11.

The third display vector polynucleotide can include B3-display vector fragment I-S5 in the direction from 5' to 3', wherein, B3 and S5 can be each independently recognition sites for the restriction endonuclease. In some cases, the S5 can be specifically recognized and cleaved by Sfi1, and the B3 can be specifically recognized and cleaved by BsmBI and/or Esp3I. For example, the B3 can include a nucleic acid sequence as set forth in SEQ ID NO: 9, and the S5 can include a nucleic acid sequence as set forth in SEQ ID NO: 10.

The fourth display vector polynucleotide can include S6-display vector fragment II-B2 in the direction from 5' to 3', wherein, S6 and B2 can be each independently recognition sites for the restriction endonuclease. In some cases, the S6 can be specifically recognized and cleaved by Sfi1, and the B2 can be specifically recognized and cleaved by BsmBI and/or Esp3I. For example, the B2 can include a nucleic acid sequence as set forth in SEQ ID NO: 8, and the S6 can include a nucleic acid sequence as set forth in SEQ ID NO: 11.

The first display vector polynucleotide, the second display vector polynucleotide, the third display vector polynucleotide and/or the fourth display vector polynucleotide of the present application can be obtained from sample materials. In some cases, the sample materials can include antigen-targeting antibodies or antigen-binding fragments thereof. The antigens may be any immunogenic fragments or determinants, including, but not limited to, PD-1, PD-L1, LAG-3, CD47, CD3. For example, the antibodies or antigen-binding fragments thereof target PD-1.

In order to screen positive bacteria into which the display vector polynucleotides have been introduced, the display vector polynucleotides (e.g., the first display vector polynucleotide, the second display vector polynucleotide, the third display vector polynucleotide and the fourth display vector polynucleotide) can also include nucleic acid sequences encoding signal peptides, for example, signal peptides expressing natural resistance genes. In one example, the 3'-end of the nucleic acid sequence encoding a signal peptide can bind to the restriction site at the 5'-end of the polynucleotide. In some cases, in order to introduce a suitable restriction site to the 3'-end part of the nucleic acid sequence encoding a signal peptide, its base sequence can be changed by unintentional mutation, but the amino acid sequence of the signal peptide remains unchanged. For example, the nucleic acid sequence encoding the signal peptide can include a nucleic acid sequence as set forth in any one selected from SEQ ID NO: 12 and SEQ ID NO: 14; alternatively, the signal peptide can include an amino acid sequence as set forth in any one selected from SEQ ID NO: 13 and SEQ ID NO: 15.

The polynucleotides can be obtained by conventional methods in the art, which can include, but not limited to: standard PCR, long PCR, hot start PCR, qPCR, RT-PCR and isothermal amplification. In some cases, primers can be designed according to the sequences of the target fragments (e.g., the display LC, the display VH, the display vector fragment I and the display vector fragment II), respectively, which were then used as templates for amplification to obtain the polynucleotides. For example, the primers for amplifying the display LC can include nucleotide sequences as set forth in SEQ ID NO: 20 and SEQ ID NO: 21. For example, the primers for amplifying the display VH can include nucleotide sequences as set forth in SEQ ID NO: 22 and SEQ ID NO: 23. For example, the primers for amplifying the display vector fragment I can include nucleotide sequences as set forth in SEQ ID NO: 18 and SEQ ID NO: 19. For example, the primers for amplifying the display vector fragment II can include nucleotide sequences as set forth in SEQ ID NO: 16 and SEQ ID NO: 17.

After the display vector polynucleotides were obtained, they can be separately introduced into a bacterium to obtain a bacterial library. Therefore, the method of the present application may further include the following steps: introducing the first display vector polynucleotide into a first display bacterium to obtain a display VH component bacterial library; introducing the second display vector polynucleotide into a second display bacterium to obtain a display LC component bacterial library; introducing the third display vector polynucleotide into a third display bacterium to obtain a display vector component I bacterial library; and introducing the fourth display vector polynucleotide into a fourth display bacterium to obtain a display vector component II bacterial library.

In the present application, the first display vector polynucleotide, the second display vector polynucleotide, the third display vector polynucleotide and the fourth display vector polynucleotide can all be linear nucleic acid molecules.

In some cases, the display vector polynucleotides can be inserted into the display component vector to form storage ligation products. In some cases, the polynucleotides can be inserted into the component vectors by using PCR cloning. The component vectors can include plasmid vectors (e.g., pBR322, pUC vectors), phage vectors (e.g., M13 vector, λ vector), phage-derived plasmids (e.g., phagemid, cosmid), and bacterial artificial chromosome (BAC). In some embodiments, the component vector may be derived from a pUC vector. For example, the component vector may be a pUC19 vector or derived from a pUC19 vector.

Then, the storage ligation products can be introduced into the bacterium to obtain the display bacterial library.

In the present application, the display bacterial library (e.g., a display VH component bacterial library and a display LC component bacterial library) can include about at least 10 (e.g., about at least 100, at least 200, at least 300, at least 400, at least 500, at least 600, at least 800, about at least 1000, about at least 10000 or more) different clones.

In the present application, the display bacterial library (e.g., the display vector component I bacterial library and the display vector component II bacterial library) can include about at least 10 (e.g., about at least 100, at least 200, at least 300, at least 400, at least 500, at least 600, at least 800, about at least 1000, about at least 10000 or more) identical clones.

In the present application, the proportion of effective clones in the display bacterial library (e.g., the display VH component bacterial library, the display LC component bacterial library, the display vector component I bacterial library and the display vector component II bacterial library) can be at least about 50% (e.g., at least about 55%, at least about 60%, at least about 65%, at least about 70%, at least about 75%, at least about 80%, at least about 85%, at least about 90%, at least about 95%, at least about 99%).

In the present application, the bacteria in the display bacterial library (e.g., the display VH component bacterial library, the display LC component bacterial library, the display vector component I bacterial library and the display vector component II bacterial library) can be cultured in liquid. The time for liquid culture may be no more than about 8 hours, for example, it may be no more than about 4 hours, no more than about 5 hours, no more than about 6 hours or no more than about 7 hours. In the present application, the operations of liquid culture are simple. In some cases, the bacteria in the display bacterial library can be cultured in a small amount of bacterial broth with spreading on a dish, and then the colonies are sorted. The time for plate culture may be about 12-18 hours, for example, it may be about 12 hours, 13 hours, 14 hours, 15 hours, 16 hours, 17 hours or 18 hours. In the present application, the plate culture allows the selection of colonies (e.g., selection of mono-clones) before sequencing analysis.

Antigen-Specific Binding Polypeptide Gene Display Vector

The method of the present application may further include specifically cleaving the VH component library, the LC component library and the display vector with restriction endonucleases (e.g., restriction endonucleases that specifically recognize the S5, S6, B2 and B3) to obtain the released first polynucleotide, the released second polynucleotide, the released third polynucleotide and the released fourth polynucleotide.

The 5'-end of the released first polynucleotide can have sticky ends after cleavage by a restriction endonuclease (e.g., the restriction endonuclease that specifically recognizes B2, e.g., BsmBI and/or Esp3I), and the 3'-end can have sticky ends after cleavage by a restriction endonuclease (e.g., the restriction endonuclease that specifically recognizes B3, e.g., BsmBI and/or Esp3I).

The 5'-end of the released second polynucleotide has sticky ends after cleavage by a restriction endonuclease (e.g., the restriction endonuclease that specifically recognizes S5, e.g., SfiI), and the 3'-end has sticky ends after cleavage by a restriction endonuclease (e.g., the restriction endonuclease that specifically recognizes S6, e.g., SfiI).

The 5'-end of the released third polynucleotide has sticky ends after cleavage by a restriction endonuclease (e.g., the restriction endonuclease that specifically recognizes B3, e.g., BsmBI and/or Esp3I), and the 3'-end has sticky ends after cleavage by a restriction endonuclease (e.g., the restriction endonuclease that specifically recognizes S5, e.g., SfiI).

The 5'-end of the released fourth polynucleotide has sticky ends after cleavage by a restriction endonuclease (e.g., the restriction endonuclease that specifically recognizes S6, e.g., SfiI), and the 3'-end has sticky ends after cleavage by a restriction endonuclease (e.g., the restriction endonuclease that specifically recognizes B2, e.g., BsmBI and/or Esp3I).

In the present application, the first polynucleotide, the second polynucleotide, the third polynucleotide and the fourth polynucleotide can all be linear nucleic acid molecules.

The method of the present application may further include mixing the released first polynucleotide, the released second polynucleotide, the released third polynucleotide and the released fourth polynucleotide so that they can be ligated directionally and cyclized to form the antigen-specific binding polypeptide gene display vector. In some cases, the directional ligation can involve using a ligase, e.g., T4 DNA ligase.

In some cases, the antigen-specific binding polypeptide gene display vector can be introduced into a bacterium to obtain an antigen-specific binding polypeptide gene display bacterial library.

In the present application, the antigen-specific binding polypeptide gene display bacterial library can include about at least 10 (e.g., about at least 100, about at least 200, about at least 300, about at least 400, about at least 500, about at least 1000, about at least 10000 or more) clones.

In the present application, the proportion of effective clones in the antigen-specific binding polypeptide gene display bacterial library can be at least about 50% (e.g., at least about 50%, at least about 55%, at least about 60%, at least about 65%, at least about 70%, at least about 75%, at least about 80%, at least about 85%, at least about 90%, at least about 95%, at least about 99%).

The time required from constructing a display vector to screening out an antigen-specific binding polypeptide of a unique sequence by using the method of the present application can be at least about 1 week (e.g., at least about 10 days, at least about 2 weeks, at least about 3 weeks, at least about 4 weeks).

In the present application, the bacteria in the antigen-specific binding polypeptide gene display bacterial library can be cultured in liquid. The time for liquid culture may be no more than about 24 hours, for example, it may be no more than about 5 hours, may be no more than about 10 hours, may be no more than about 15 hours, no more than about 20 hours, no more than about 22 hours or no more than about 22 hours. In the present application, the operations of liquid culture are simple. In some cases, the bacteria in the bacterial library can be cultured in a small amount of bacterial broth with spreading on a dish, and then the colonies are selected. The time for plate culture may be about 12-18 hours, for example, it may be about 12 hours, 13 hours, 14 hours, 15 hours, 16 hours, 17 hours or 18 hours. In the present application, the plate culture allows the selection of colonies (e.g., selection of mono-clones) before sequencing analysis.

The method may further include introducing the antigen-specific binding polypeptide gene display vector into a cell, and acquiring the antigen-specific binding polypeptide from the cell. For example, the cell may be a mammalian cell. The antigen-specific binding polypeptide can then be obtained from the cell.

Restriction Site

In the present application, the recognition site sequence of the restriction endonuclease is designed as not being included in the polynucleotide encoding the antigen-binding polypeptide or fragments thereof. The restriction endonucleases of the present application can specifically recognize B2, B3, S5 and S6, respectively. Wherein, the B2, B3, S5 and S6 can be each independently recognition sites for the restriction endonuclease.

The recognition sites for the restriction endonucleases in the present application can be specifically recognized by 1, 2, 3, 4 or more restriction endonucleases, respectively. In some cases, the restriction endonucleases may be selected from SfiI, BsmBI, and/or Esp3I. In other cases, other feasible restriction endonucleases can also be selected.

In the present application, the restriction endonuclease may be selected from SfiI, BsmBI, and Esp3I. In the present application, the BsmBI and Esp3I may be isozymes, that can recognize the same recognition sites for the restriction endonuclease.

In the present application, for example, the S5 and S6 can be recognized and cleaved by SfiI. In the present application, for example, the B2 and B3 can be recognized and cleaved by BsmBI and/or Esp3I.

For example, SfiI can recognize a sequence composed of 13 bases (5' to 3') GGCCNNNN/NGGCC, which can form an overhang sequence (e.g., a single-stranded sequence containing 3 bases) at the 3'-end after enzymatic cleavage, wherein N may represent any one of the four bases GATC. Therefore, there are 4^5 different sequences that can be recognized by SfiI.

For example, BsmBI and Esp3I can recognize a sequence composed of 12 bases (5' to 3') CGTCTCN/NNNNN, which can form an overhang sequence (e.g., a single-stranded sequence containing 4 bases) at the 5'-end after enzymatic cleavage, wherein N may represent any one of the four bases GATC. Therefore, there are 4^6 different sequences that can be recognized by BsmBI and Esp3I.

In some cases, the recognition sites for the restriction endonucleases may be the sites that are specifically recognized and cleaved by SfiI. For example, they can be referred to as S5 and S6, respectively. For example, the S5 can include a nucleic acid sequence as set forth in SEQ ID NO: 10. For another example, the S6 can include a nucleic acid sequence as set forth in SEQ ID NO: 11.

The recognition sites for the restriction endonucleases may be the sites that are specifically recognized and cleaved by BsmBI and/or Esp3I. For example, they can be referred to as B2 and B3, respectively. For example, the B2 can include a nucleic acid sequence as set forth in SEQ ID NO: 8. Further for example, the B3 can include a nucleic acid sequence as set forth in SEQ ID NO: 9.

It should be noted that, the recognition sites for the restriction endonucleases in the present application include, but are not limited to, the recognition sites listed herein, and may also include the recognition sites for other restriction endonucleases not listed, as well as other recognition sites for the restriction endonucleases, provided that they do not cause undesired recognition or cleavage of the target sequence (e.g., a polynucleotide encoding the antigen-binding polypeptide or fragments thereof).

In another aspect, the present application further provides the antigen-specific binding polypeptide gene display bacterial library.

In another aspect, the present application further provides the display vector produced by the method.

Without intending to be limited by any theory, the following examples are only to illustrate the fusion protein, its preparation method and use of the present application, and are not used to limit the inventive scope of the present application.

EXAMPLES

Example 1 Construction of Phage Surface Antibody (Fab) Display Library of Human PBMC 1.1 Acquisition of Total RNA/mRNA of Immunization Materials Total RNA was extracted from human peripheral blood lymphocytes, and mRNA was further isolated from the total RNA (Takara Cat #Z652N/636592, for specific test steps, see the product instruction).

1.2 Design and Synthesis of Primers

Referring to Phage Display (A Laboratory Manual, ISBN 0-87969-546-3), primers were designed for human heavy chain variable region VH, light chain KLC (full-length Kappa light chain), and light chain LLC (full-length Lamda light chain). Wherein, the 5'-end of the light chain forward primer contains the nucleotide sequence GGCCCAGGCGGCC (SEQ ID NO: 78) of R1, and the 5'-end of the reverse primer contains the nucleotide sequences GGCCACATAGGCC (SEQ ID NO: 79) of R2; 5'-end of the heavy chain variable region forward primer contains the nucleotide sequence GGCCCAACCGGCC (SEQ ID NO: 80) of R5, and the 5'-end of the reverse primer contains the nucleotide sequence GGCCCTCAGCGGCC (SEQ ID NO: 81) of R6. The primers were synthesized by GENEWIZ.

Forward and reverse primers for amplifying linkers were designed with the pComb3x vector as the template. Wherein, the 5'-end of the forward primer contains the nucleotide sequence GGCCACATAGGCC (SEQ ID NO: 79) of R3, and the 5'-end of the reverse primer contains the nucleotide sequence GGCCCAACCGGCC (SEQ ID NO: 80) of R4.

Specific primer sequences can refer to Table 1-1 below:

TABLE 1-1

| Primerssequence-1 | |
| --- | --- |
| Primer Name | SEQ ID NO: |
| Forward primer of light chain KLC | 82-99 |
| Reverse primer of light chain KLC | 100 |
| Forward primer of light chain LLC | 101-125 |
| Reverse primer of light chain LLC | 126 |
| Forward primer of VH | 127-150 |
| Reverse primer of VH | 151-155 |
| Forward primer of linker | 156 |
| Reverse primer of linker | 157 |

1.3 Acquisition of the First Polynucleotide and the Third Polynucleotide

A component antibody gene library was amplified by a two-step approach.

Step 1. Using the mRNA obtained in Example 1.1 as a template, cDNA was synthesized by reverse transcription with MMLV from Promega (according to the product instruction of Promega Co., where the primer was Thermo Cat #N8080127, and the reverse transcriptase was Promega Cat #M1701).

Step 2. Using the cDNA obtained in step 1 as a template, and using the primers obtained in Example 1.2, the KLC, LLC and VH gene libraries of the component antibody were amplified by PCR (Takara Cat #RR900A, according to the product instruction of the company). After purification and recovery by gel electrophoresis (using Axygen Gel Extraction Kit, and operated according to the instruction in "Molecular Cloning: A Laboratory Manual"), PCR products, that are KLC fragments, LLC fragments, and VH fragments, were obtained respectively.

1.4 Construction of Storage Vectors 1.4.1 Design of Primers

Primers were designed with reference to the content in Example 1.2.

Primers for obtaining storage vectors were designed and synthesized. Specific primer sequences can refer to Table 1-2 below:

TABLE 1-2

| Primer sequence-2 | |
| --- | --- |
| Primer Name | SEQ ID NO: |
| Forward primer of R1-1kb-R2 | 158 |
| Reverse primer of R1-1kb-R2 | 159 |
| Forward primer of R5-1kb-R6 | 162 |
| Reverse primer of R5-1kb-R6 | 163 |

1.4.2 PCR Amplification

Using human IgG1 Fc (SEQ ID NO: 164) with a length of 1 kb as a template, PCR was performed using the primers prepared in Example 1.4.1, that are the forward primer of R1-1 kb-R2 and the reverse primer of R1-1 kb-R2. After purification and recovery by gel electrophoresis (using Axygen Gel Extraction Kit), the PCR product, R1-1 kb-R2 (SEQ ID NO: 165), was obtained.

Using the pComb3x vector as a template, PCR was performed using the forward primer of R3-linker-R4 (SEQ ID NO: 160) and the reverse primer of R3-linker-R4 (SEQ ID NO: 161). After purification and recovery by gel electrophoresis (using Axygen Gel Extraction Kit), the PCR product R3-linker-R4 (SEQ ID NO: 167) was obtained. Wherein, the linker may have a length of 72 bp, and its nucleotide sequence is as set forth in SEQ ID NO:166.

Using human IgG1 Fc (SEQ ID NO: 164) with a length of 1 kb as a template, PCR was performed using the primers prepared in Example 1.4.1, that are the forward primer of R5-1 kb-R6 and the reverse primer of R5-1 kb-R6. After purification and recovery by gel electrophoresis, the PCR product R5-1 kb-R6 (SEQ ID NO: 168) was obtained.

Figures 9, 10:
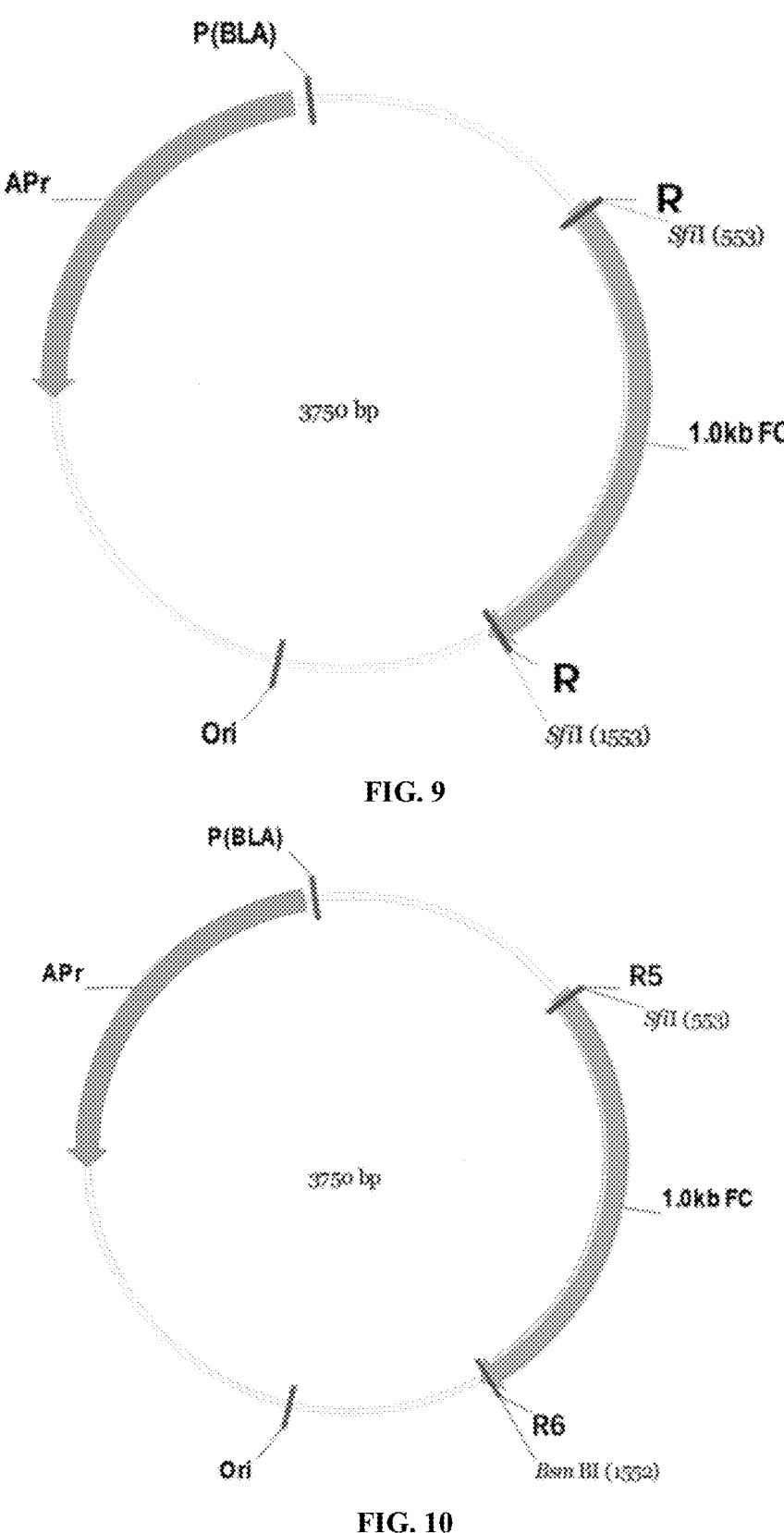
FIG. 9 shows a schematic diagram of the light chain storage vector in the process of constructing the phage library.
FIG. 10 shows a schematic diagram of the heavy chain storage vector in the process of constructing the phage library.

1.4.3 Construction of Light Chain Storage Vectors and Heavy Chain Storage Vectors By means of the method of TA cloning (TA cloning kit, purchased from Takara Co.), the R1-1 kb-R2 fragment prepared in 1.4.2 was inserted into a pMD19-T vector to obtain a light chain storage vector DDB-R1-1 kb-R2 for inserting into the full-length light chain gene library, and its vector map was shown in FIG. 9.

By means of the method of TA cloning (TA cloning kit, purchased from Takara Co.), the R5-1 kb-R6 fragment prepared in 1.4.2 was inserted into a pMD19-T vector to obtain a vector containing the R5-1 kb-R6 fragment, which was then used as the template to remove the original BsmBI restriction site in this vector by primer mutation, so as to obtain a heavy chain storage vector DDB-R5-1 kb-R6 for inserting into the VH gene library, and its vector map was shown in FIG. 10.

Specific primer sequences can refer to Table 1-3 below:

TABLE 1-3

| Primer sequence-3 | |
| --- | --- |
| Primer Name | SEQ ID NO: |
| Vector-mutated forward primer | 169 |
| Vector-mutated reverse primer | 170 |

Figure 11:
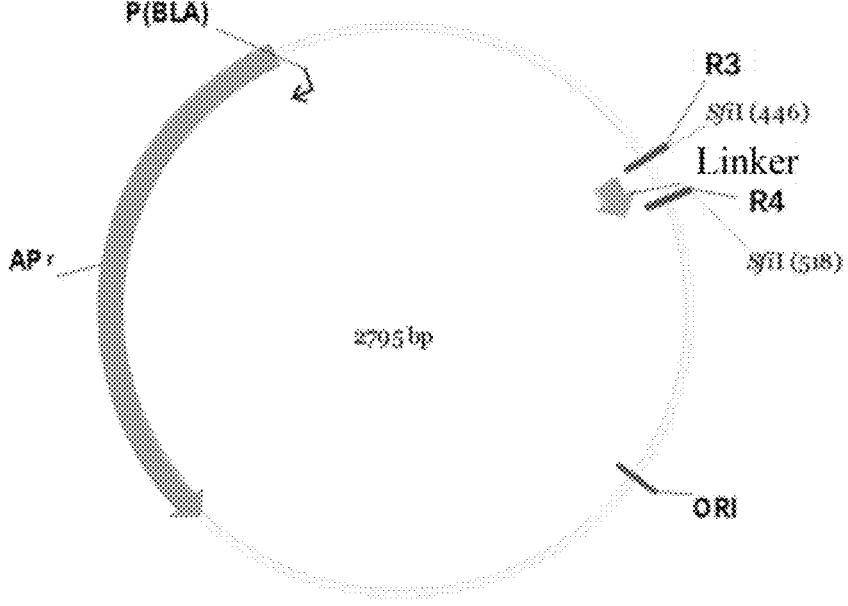
FIG. 11 shows a schematic diagram of the linker storage vector in the process of constructing the phage library.

1.4.4 Construction of Linker Storage Vectors and Acquisition of Linker Component Bacteria By means of the method of TA cloning (TA cloning kit, purchased from Takara Co.), the R3-linker-R4 prepared in Example 1.4.2 was inserted into a pMD19-T vector to obtain a linker storage vector DDB-R3-linker-R4, and its vector map was shown in FIG. 11. The TG1 competent bacteria (Lucigen Co.) were transformed with the linker storage vector, and cultured overnight at 37° C. on a plate. The colonies were sent for sequencing, and then the colonies were collected to obtain linker component bacteria, which can be cryopreserved for later use.

1.5 Acquisition of Component Bacterial Library 1.5.1 Acquisition of Light Chain Component Bacterial Library The polynucleotides including KLC and LLC prepared in Example 1.3 were digested with the restriction endonucleases R1 and R2 to obtain the target light chain fragments (about 0.65 kb).

The light chain storage vector DDB-R1-1 kb-R2 prepared in Example 1.4 was digested with the restriction endonucleases R1 and R2 to obtain the light chain storage vector fragments (about 2.7 kb).

The resulting target light chain fragments were mixed with the light chain storage vector fragments, then ligated using the T4 DNA ligase (purchased from NEB, Thermo) to obtain a light chain storage ligation product. The TG1 competent bacteria (Lucigen, Cat #60502-2, operated according to the instruction of the manufacturer) were transformed with the light chain storage ligation product, spread on ampicillin-resistant plates (Thermo, Cat #240845) and cultured overnight at 37° C. The colonies were sent for sequencing, and then all of the colonies were collected to obtain a light chain component bacterial library, of which the quality can be detected and/or which can be cryopreserved for later use.

1.5.2 Acquisition of Heavy Chain Component Bacterial Library

The polynucleotides prepared in Example 1.3 were digested with the restriction endonucleases R5 and R6 to obtain the target heavy chain variable region fragments (about 0.35 kb).

The heavy chain storage vector DDB-R5-1 kb-R6 prepared in Example 1.4 was digested with the restriction endonucleases R5 and R6 to obtain the heavy chain storage vector fragments (about 2.7 kb).

The resulting target heavy chain variable region fragments were mixed with the heavy chain storage vector fragments, then ligated using the T4 DNA ligase (purchased from NEB, Thermo) to obtain a heavy chain storage ligation product. The TG1 competent bacteria (Lucigen, Cat #60502-2, operated according to the instruction of the manufacturer) were transformed with the heavy chain storage ligation product, spread on ampicillin-resistant plates (Thermo, Cat #240845) and cultured overnight at 37° C. The colonies were sent for sequencing, and then all the colonies were collected to obtain a heavy chain component bacterial library, of which the quality can be detected and/or which can be cryopreserved for later use.

1.6 Acquisition of Light Chain Component Plasmid, Heavy Chain Component Plasmid and Linker Fragments Using a plasmid extraction kit (purchased from Axygen), the plasmids in the light chain component bacterial library prepared in Example 1.5.1 and in the heavy chain component bacterial library prepared in Example 1.5.2 were separately extracted to obtain a light chain component plasmid and a heavy chain component plasmid, respectively.

The light chain component plasmid prepared in Example 1.5.1 was digested with the restriction endonucleases R1 and R2, then purified and recovered by gel electrophoresis to obtain light chain inserting fragments LC.

The heavy chain component plasmid prepared in Example 1.5.2 was digested with the restriction endonucleases R5 and R6, then purified and recovered by gel electrophoresis to obtain heavy chain inserting fragments HC.

Using a plasmid extraction kit (purchased from Axygen), the plasmid in the linker component bacteria prepared in Example 1.4.4 was extracted to obtain a linker component plasmid. Using the linker component plasmid or the linker storage vector in Example 1.4.4 as a template, the 0.8 kb of fragment containing the linker was amplified with the linker forward primer (SEQ ID NO: 156) and the linker reverse primer (SEQ ID NO: 157), and the 0.8 kb PCR product was then digested with restriction endonucleases R3 and R4, then purified and recovered by gel electrophoresis (using a small fragment gel extraction kit, purchased from Lifefeng Biotech, Cat #DK402) to obtain 72 pb of linker fragments.

1.7 Acquisition of Display Vectors

Figure 12:
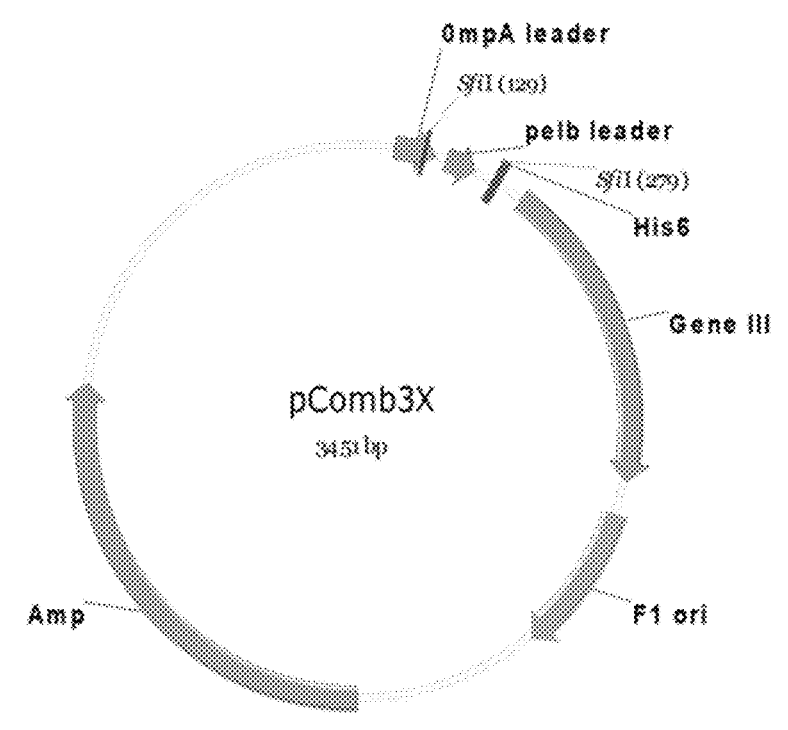
FIG. 12 shows a schematic diagram of the pCom3x vector in the process of constructing the phage library.
Figure 13:
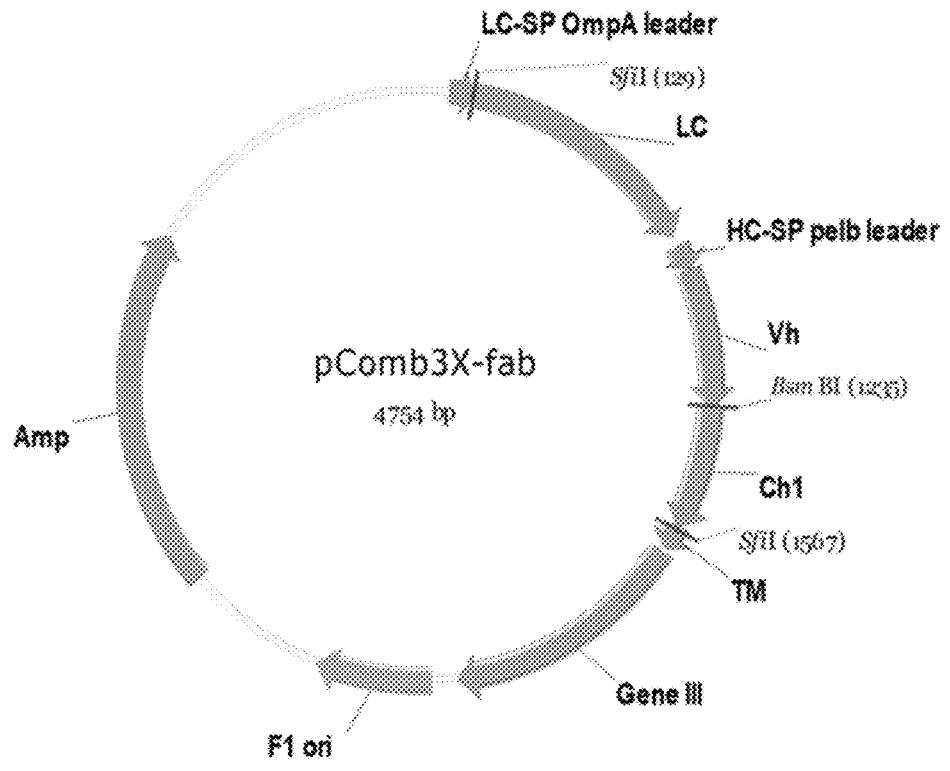
FIG. 13 shows a schematic diagram of the phage display vector in the process of constructing the phage library.

The pComb3x vector was purchased, and its vector map was shown in FIG. 12, and the map of the modified pComb3x-fab vector used for antibody Fab display was shown in FIG. 13.

The SfiI restriction site at the 3'-end of the Fab gene in the pComb3x-fab vector was removed by nonsense mutation.

Figure 14:
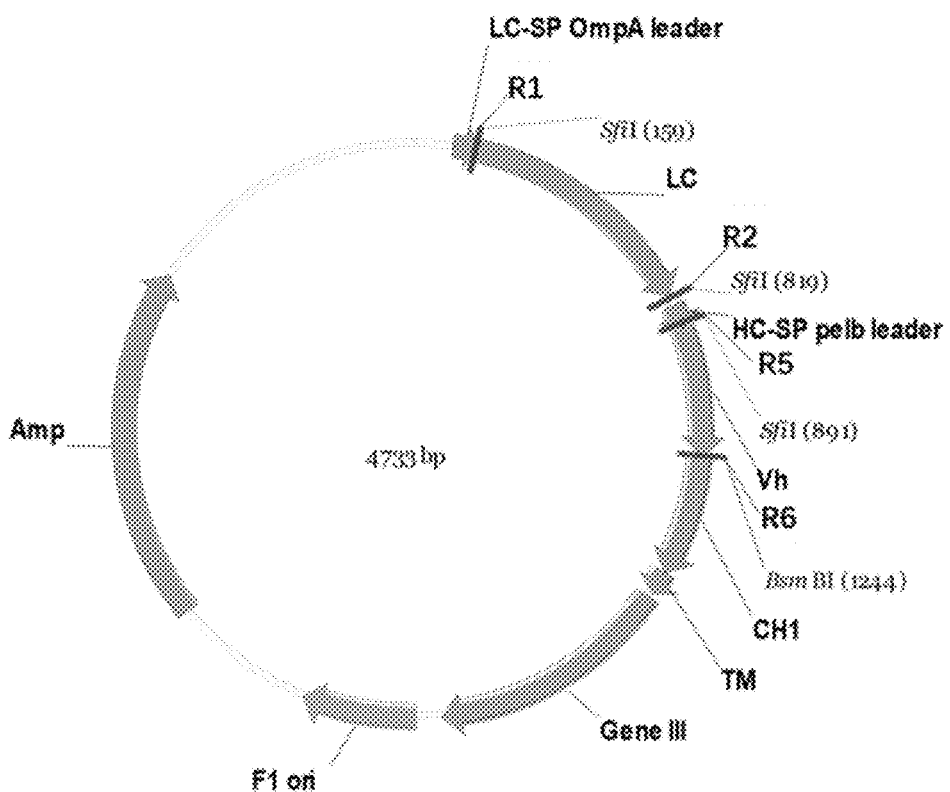
FIG. 14 shows a schematic diagram of the plasmid for the ligation product for display in the process of constructing the phage library.

After then, a restriction endonuclease R2 restriction site was added downstream of the light chain stop codon in the vector after the nonsense mutation, and a restriction endonuclease R5 restriction site was introduced at the end of the signal peptide of the heavy chain variable region through nonsense mutation, to obtain a modified phage display vector DDB-R1R2R5R6, of which the map was shown in FIG. 14.

1.8 Preparation of Display Bacterial Library

The display vector DDB-R1R2R5R6 prepared in Example 1.7 was digested with the restriction endonuclease R7 and the restriction endonuclease R8 to obtain 3.6 kb of display vector fragments.

The light chain inserting fragment LC (0.65 kb), the heavy chain inserting fragment HC (0.35 kb), the linker fragment (72 bp) and the phage display vector fragment (3.6 kb) obtained in Example 1.6 were mixed at a molecular ratio of 1:1:1:1, and ligated with T4 DNA ligase at 20° C. for more than 20 hours to obtain a ligation product for display.

The ligation product was purified by PCR-Clean-up, transferred into TG1 competent bacteria (Lucigen, Cat #60502-2, operated according to the instruction of the manufacturer), and cultured in 2YT medium without antibiotics at 37° C. while shaking at 250 rpm for 60 minutes, then spread on ampicillin-resistant plates (Thermo, Cat #240845) and grown overnight at 37° C. The colonies were sorted for sequencing, and all the colonies grown on the plates were collected, that is, the phage display bacterial library, which can be preserved for later use.

1.9 Preparation of Display Antibody Phage Library

An appropriate amount of bacterial liquid was taken from the display bacterial library prepared in Example 1.8, and cultured in 2YT medium (containing 100 µg/ml of ampicillin and 2% glucose) at 37° C. until OD600 reached 0.5. Then, M13KO7 helper phage (purchased from NEB, Cat #N0315S, MOI of about 10-20) was added to the bacterial solution and mixed uniformly. After mixing, it was allowed to stand at 37° C. for 30 minutes, and shaken at 37° C. and 250 rpm for 30 minutes. Upon centrifugation, the supernatant portion of the culture medium containing the M13KO7 helper phage was discarded. The bacteria were resuspended in the culture medium (containing ampicillin and kanamycin) 4 times the original volume of the bacterial solution, and shaken overnight at 30° C. and 250 rpm. The next day, the phages were collected by PEG precipitation. The concentration of the phages was titrated, and the phages were stored in aliquots to obtain a display antibody phage library.

Example 2 Construction of Display Vectors 2.1 Acquisition of Sample Materials

In order to construct the display vectors as shown in FIG. 1, the PD-1-targeting antibody Pembrolizumab as well as the pDGB4 vector were chosen as examples. The nucleotide sequence of the light chain of Pembrolizumab was: SEQ ID NO: 5, the nucleotide sequence of the heavy chain variable region of Pembrolizumab was: SEQ ID NO: 6, and the nucleotide sequence of the pDGB4 vector was: SEQ ID NO: 7.

2.2 Design of Restriction Site

Restriction endonucleases BsmBI and SfiI were chosen to design the sequences of 2 BsmBI recognition sites (B2 and B3) and the sequences of 2 SfiI recognition sites (S5 and S6), wherein, the nucleotide sequence of B2 was as set forth in SEQ ID NO: 8, the nucleotide sequence of B3 was as set forth in SEQ ID NO: 9, the nucleotide sequence of S5 was as set forth in SEQ ID NO: 10, and the nucleotide sequence of S6 was as set forth in SEQ ID NO: 11.

2.3 Selection of Signal Peptides

Two signal peptides expressing native antibody genes were selected: SP1 and SP2. In order to introduce suitable restriction sites at the 3'-end portion of the signal peptide, the base sequences of the two signal peptides had been changed by unintentional mutation, but the amino acid sequences of the signal peptides remained unchanged. SP1 expressed the display VH, whose nucleotide sequence was as set forth in SEQ ID NO: 12, and whose amino acid sequence was as set forth in SEQ ID NO: 13; SP2 expressed the display LC, whose nucleotide sequence was as set forth in SEQ ID NO: 14, and whose amino acid sequence was as set forth in SEQ ID NO: 15.

2.4 Acquisition of Display Vector Polynucleotides

Primers for the display VH, the display LC as well as the display vector fragment I and the display vector fragment II were designed respectively, and the expression of them were all driven by a CMV promoter. The synthetic primers were amplified by PCR with the sequences in 2.1 as the template. The sequences were listed in Table 2.

TABLE 2

| Sequences of fragments | | | |
|---|---|---|---|
| Display vector polynucleotide | Template | Forward primer | Reverse primer |
| Display LC | Light chain of Pembrolizumab (SEQ ID NO: 5) | P5 (SEQ ID NO: 20) | P6 (SEQ ID NO: 21) |
| Display VH | Heavy chain variable region of Pembrolizumab (SEQ ID NO: 6) | P7 (SEQ ID NO: 22) | P8 (SEQ ID NO: 23) |
| Expression vector fragment I | pDGB4 (SEQ ID NO: 7) | P3 (SEQ ID NO: 18) | P4 (SEQ ID NO: 19) |
| Expression vector fragment II | pDGB4 (SEQ ID NO: 7) | P1 (SEQ ID NO: 16) | P2 (SEQ ID NO: 17) |

Four display vector polynucleotides were amplified by PCR (LA Taq, Takara Co., performed according to the product instruction of the company), and the template and primer sequences used were shown in Table 2. PCR products were obtained respectively after purification and recovery by gel electrophoresis (operated according to the instruction in "Molecular Cloning: A Laboratory Manual"). By means of the method of TA cloning (TA cloning kit, purchased from Takara Co.), the PCR products were inserted into a pUC19 plasmid vector to obtain the storage ligation product. The DH5a competent bacteria (Takara Co.) were transformed with the storage vector product, and cultured overnight at 37° C. on a plate. The colonies were sent for sequencing, and then bacteria were obtained which are display vector poly-nucleotides containing the desired sequences, that are the first display vector polynucleotide containing the display VH, the second display vector polynucleotide containing the display LC, the third display vector polynucleotide contain-ing the display vector fragment I, and the fourth display vector polynucleotide containing the expression vector frag-ment II. The bacteria can be cryopreserved as the bacterial library for later use.

2.5 Digestion

The plasmids of bacteria in the bacterial library of Example 2.4 were respectively extracted by using a plasmid extraction kit (purchased from Axygen). Then the plasmid vectors were digested with restriction endonucleases BsmBI and SfiI, isolated and purified by electrophoresis to obtain the four cleaved display vector polynucleotides.

2.6 Acquisition of Display Vectors by Ligation

Figure 2:
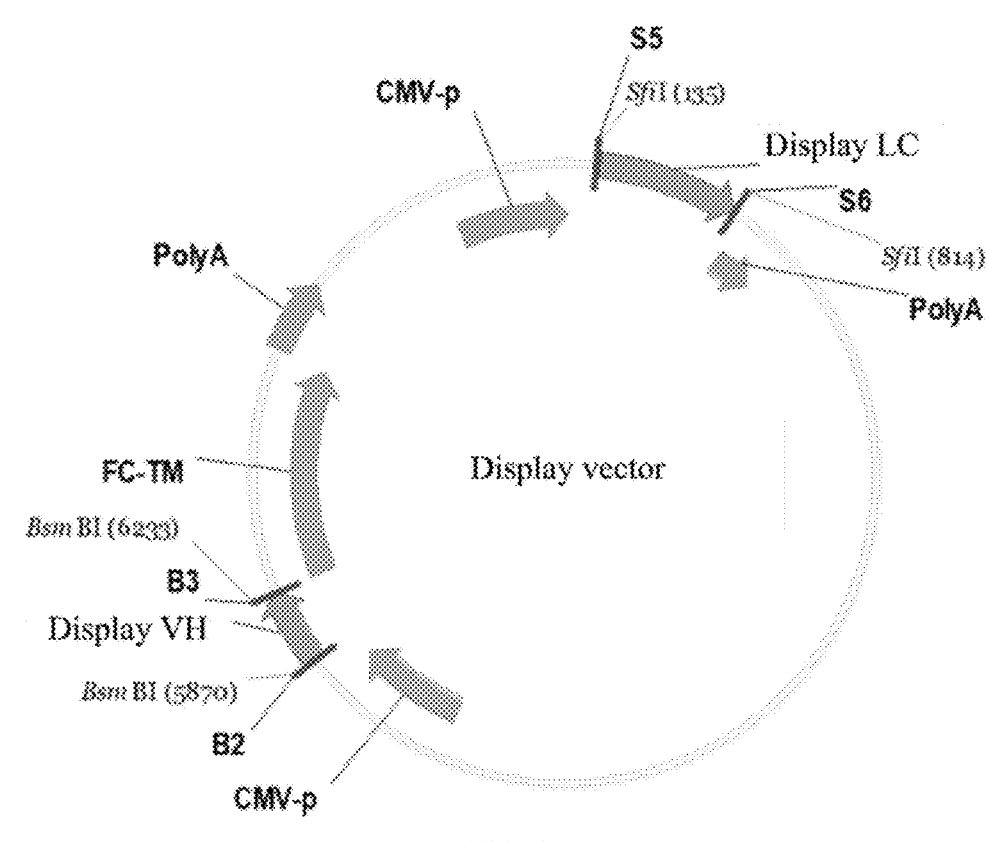
FIG. 2 shows an example of the display vector of the present application.

The four cleaved display vector polynucleotides obtained in Example 2.5 were mixed in equal molecular proportions, into which was added a ligase so that they were ligated directionally and cyclized to form an expression vector. The expression vector was transferred into DH5a competent bacteria (Takara, operated according to the instruction of the manufacturer), and cultured in 2YT medium without anti-biotics at 37° C. while shaking at 250 rpm for 60 minutes, then spread on ampicillin-resistant plates (Thermo, Cat #240845) and grown overnight at 37° C. The colonies were sorted for sequencing, and display vectors containing correct sequences were obtained. The specific structures of the display vectors were shown in FIG. 2.

Example 3 Construction of VH Component Vector and LC Component Vector 3.1 VH Component Vector Using human IgG1 Fc with a length of 1 kb as a template, PCR was performed using the primers DDB214 and DDB215. After purification and recovery by gel electropho-resis, the PCR product B2-KB-B3 was obtained, wherein, the nucleotide sequence of DDB214 was as set forth in SEQ ID NO: 1, and the nucleotide sequence of DDB215 was as set forth in SEQ ID NO: 2. B2-KB-B3 was inserted into an expression component vector, the pMD19 vector, to obtain a VH component vector storage plasmid. The TG1 compe-tent bacteria (Lucigen Co.) were transformed with the VH component vector storage plasmid, and cultured overnight at 37° C. on a plate. The colonies were sorted for sequencing to determine the VH component vector containing a correct sequence. The structure of the VH component vector was shown in FIG. 3.

3.2 LC Component Vector

Using human IgG1 Fc with a length of 1 kb as a template, PCR was performed using the primers DDB216 and DDB217. After purification and recovery by gel electropho-resis, the PCR product S5-KB-S6 was obtained, wherein, the nucleotide sequence of DDB216 was as set forth in SEQ ID NO: 3, and the nucleotide sequence of DDB217 was as set forth in SEQ ID NO: 4. S5-KB-S6 was inserted into an expression component vector, the pMD19 vector, to obtain an LC component vector storage plasmid. The TG1 com-petent bacteria (Lucigen Co.) were transformed with the LC component vector storage plasmid, and cultured overnight at 37° C. on a plate. The colonies were sorted for sequencing to determine the LC component vector containing a correct sequence. The structure of the LC component vector was shown in FIG. 4.

Example 4 Acquisition of Antigen-Specific VH and Antigen-Specific LC 4.1 First Round of Screening 500 µl of the phage library constructed in Example 1 (Fab library, the original library capacity was $4 \times 10^{10}$, the effec-tive clones were more than 80%, and the prepared phage library was $2 \times 10^{13}$/ml) was taken. Biotin-labeled ROR1 antigen (Acro Biosystems, Cat #RO1-H82E6) was mixed with the phage library (with an antigen concentration of 10 µg/ml), and shaken at room temperature for 2 hours to allow the phage displaying the antigen-specific Fab to bind to the biotin-labeled antigen. Next, 80 µl of magnetic beads (pur-chased from Invitrogen) were mixed with the phage library-antigen, shaken at room temperature for 20 minutes, and the antigen-specific phage was captured by the binding of avidin and biotin on the surface of the magnetic beads to form a magnetic bead-avidin-biotin-antigen-Fab antibody fragment cross-linker. Then, the formed cross-linker carrying the ROR1 antigen-specific Fab was collected by a magnetic stand, and the phage displaying the ROR1 antigen-specific Fab was eluted with pH 2.2 glycine solution, and neutralized with pH 8.0 Tris buffer to pH 7.0, finally obtaining 550 µl of phage solution.

4.2 Second Round of Screening

250 µl of the phage solution obtained from the first round of screening was mixed with an equal amount of 4% Milk-PBS to a final volume of 0.5 ml. Next, 4 µg of biotin-labeled antigen was mixed with the phage solution to a final antigen concentration of 8 µg/ml, and shaken at room temperature for 3 hours to allow the phage displaying the antigen-specific Fab to bind to the biotin-labeled antigen. Next, 40 µl of magnetic beads were mixed with the phage solution-antigen, shaken at room temperature for 20 min-utes, and the antigen-specific phage was captured by the binding of avidin and biotin on the surface of the magnetic beads to form a magnetic bead-avidin-biotin-antigen-Fab antibody fragment cross-linker. The formed cross-linker carrying the ROR1 antigen-specific Fab was collected by a magnetic stand. Then, the magnetic beads were washed with 1×PBST for 4 times, and then washed with 1×PBS for 4 times. Finally, the phage displaying the ROR1 antigen-specific Fab was eluted with 50 µl of pH 2.2 glycine solution, and neutralized with 20 µl of pH 8.0 Tris buffer to pH 7.0, finally obtaining 75 µl of phage solution.

4.3 Infection of TG1 Bacteria

75 µl of the phage solution obtained from the second round of screening in Example 4.2 was mixed with 500 µl of the TG1 bacteria in the logarithmic growth phase, with standing at 37° C. for 30 minutes. Then, the infected TG1 bacterial solution was spread on Amp-resistant plates and cultured overnight at 37° C.

4.4 Screening of Positive Clones by ELISA

The colonies growing on the plate were counted, inocu-lated on two pieces of 96-well deep-well plates with each well containing 400 µl of culture medium (2YT+Amp+0.2% glucose), and cultured at 37° C. while shaking for 6 hours. Each well was added with 400 µl of culture medium con-taining IPTG (2YT+Amp+2 mM IPTG) with the final con-centration of IPTG at 1 mM, and cultured overnight at 30° C. while shaking at 250 rpm. The two pieces of 96-well ELISA plates were coated with ROR1 antigen without biotin labeling at 100 ng/100 µl/well, at 4° C. overnight.

After washing and blocking the 96-well ELISA plates that had been coated with antigen overnight, 100 µl of overnight-cultured bacterial solution was added into each well, incubated at 37° C. for 1 hour, and washed again; and secondary antibodies (HRP-labeled anti-human IgG-Fab antibodies) were then added and incubated at 37° C. for 40 minutes. After washing, a developing solution was added and stored in dark for 30 minutes. The OD600 values were read by a microplate reader, with the results shown in Tables 3-1 and 3-2 below.

TABLE 3-1

| | Preliminary screening results of positive clones-1 | | | | | | | | | | | |
| #1 | 1 | 2 | 3 | 4 | 5 | 6 | 7 | 8 | 9 | 10 | 11 | 12 |
| --- | --- | --- | --- | --- | --- | --- | --- | --- | --- | --- | --- | --- |
| A | 0.365 | 0.143 | 1.138 | 0.080 | 0.333 | 0.235 | 0.714 | 0.819 | 0.073 | 0.101 | 0.074 | 0.079 |
| B | 0.118 | 0.673 | 0.089 | 0.101 | 0.076 | 1.049 | 0.065 | 0.402 | 0.408 | 0.263 | 0.065 | 0.073 |
| C | 1.827 | 0.106 | 0.102 | 0.096 | 0.070 | 0.070 | 0.074 | 0.066 | 0.168 | 0.067 | 0.185 | 1.480 |
| D | 0.119 | 0.118 | 0.078 | 0.185 | 0.080 | 0.127 | 0.072 | 0.068 | 0.067 | 0.079 | 0.110 | 0.091 |
| E | 0.151 | 1.598 | 0.163 | 1.526 | 0.102 | 0.090 | 0.079 | 0.065 | 0.058 | 0.281 | 0.083 | 0.085 |
| F | 0.104 | 0.102 | 0.107 | 0.116 | 0.114 | 0.093 | 0.115 | 2.056 | 0.063 | 0.07 | 0.066 | 0.196 |
| G | 0.095 | 0.103 | 0.091 | 0.161 | 0.199 | 0.106 | 1.637 | 0.075 | 0.559 | 0.069 | 0.284 | 0.130 |
| H | 0.137 | 0.131 | 0.227 | 0.150 | 0.516 | 0.241 | 0.096 | 0.090 | 0.302 | 0.094 | 0.103 | 0.290 |

TABLE 3-2

| | Preliminary screening results of positive clones-2 | | | | | | | | | | | |
| #2 | 1 | 2 | 3 | 4 | 5 | 6 | 7 | 8 | 9 | 10 | 11 | 12 |
| --- | --- | --- | --- | --- | --- | --- | --- | --- | --- | --- | --- | --- |
| A | 0.075 | 0.085 | 0.076 | 0.194 | 0.084 | 0.080 | 0.077 | 0.066 | 0.080 | 0.072 | 0.206 | 0.079 |
| B | 0.068 | 0.161 | 0.068 | 0.945 | 0.075 | 0.072 | 0.074 | 0.077 | 0.949 | 0.070 | 0.097 | 0.083 |
| C | 0.065 | 0.062 | 1.787 | 0.068 | 0.068 | 0.313 | 0.071 | 0.087 | 0.535 | 0.082 | 0.080 | 0.097 |
| D | 0.071 | 0.072 | 0.068 | 1.787 | 0.338 | 0.070 | 0.069 | 0.093 | 0.110 | 0.076 | 0.108 | 0.126 |
| E | 0.372 | 0.088 | 0.076 | 0.068 | 0.071 | 0.175 | 0.275 | 0.083 | 0.106 | 0.156 | 0.076 | 0.083 |
| F | 0.085 | 1.414 | 0.068 | 0.076 | 0.080 | 0.087 | 0.2228 | 0.067 | 0.094 | 0.093 | 0.137 | 0.129 |
| G | 0.127 | 0.076 | 0.189 | 0.068 | 0.065 | 0.149 | 1.020 | 0.070 | 0.107 | 0.088 | 0.083 | 0.124 |
| H | 0.078 | 1.649 | 0.517 | 0.517 | 0.071 | 0.067 | 0.067 | 0.107 | 0.267 | 0.189 | 0.090 | 0.132 |

Figure 5A:
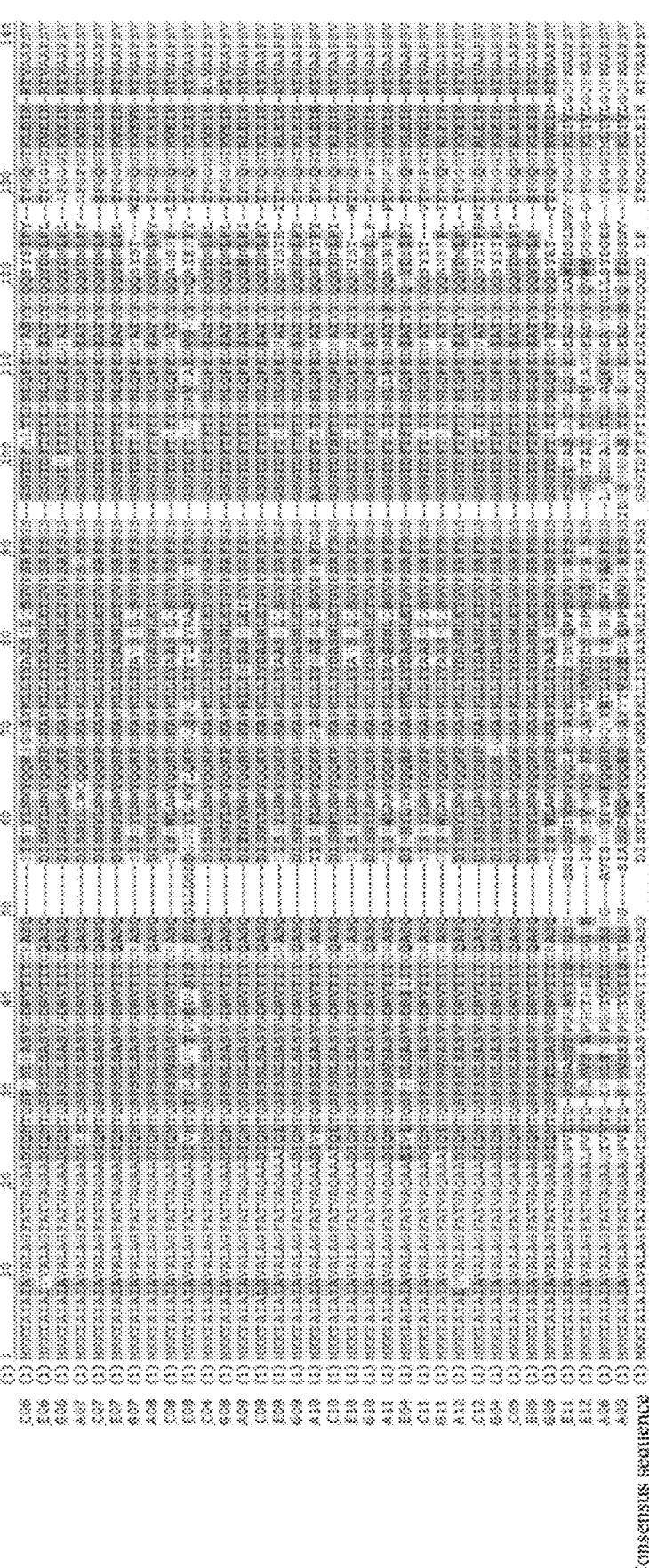
FIG. 5A shows the amino acid sequence of the antigen-specific LC of the present application.
Figure 5B:
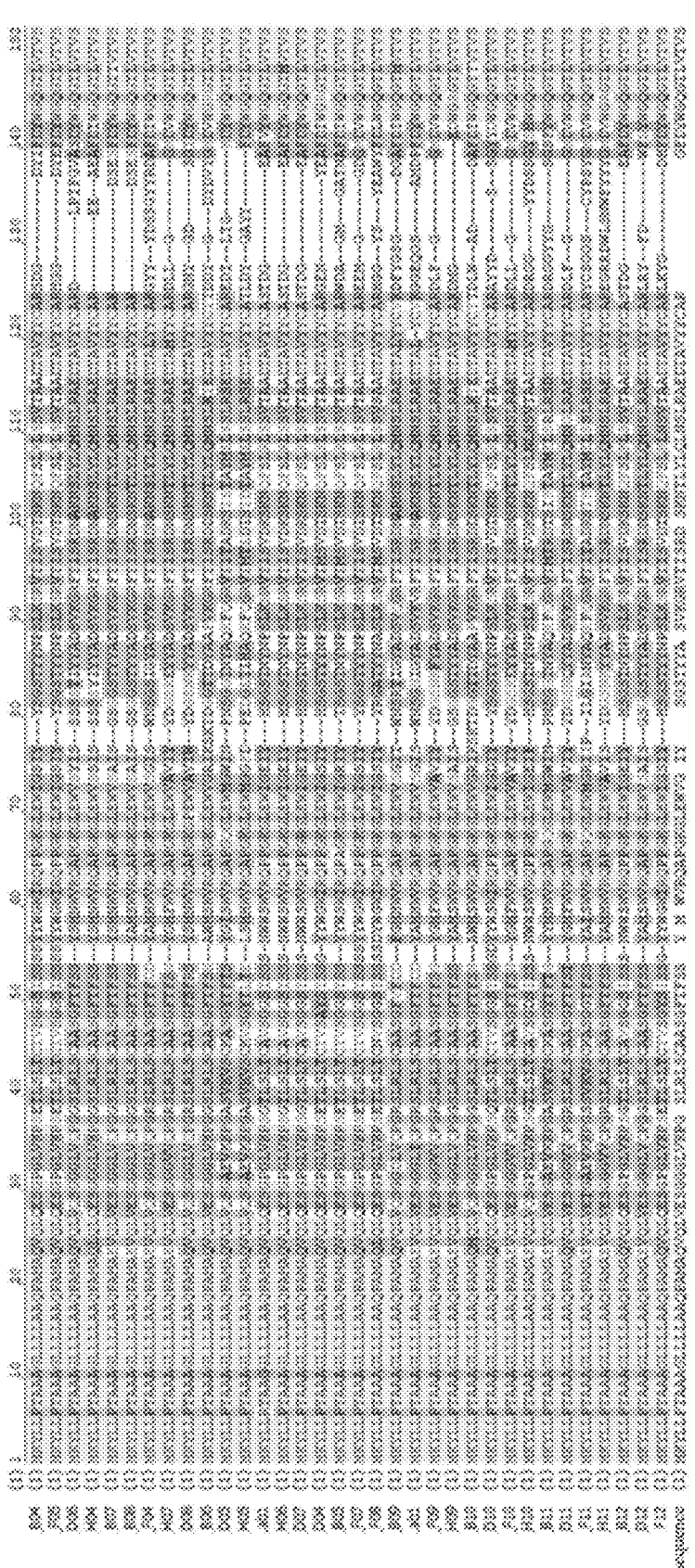
FIG. 5B shows the amino acid sequence of the antigen-specific VH of the present application.

A total of 35 clones with reads greater than 0.25 were sent for sequencing. The sequence analysis showed that there were 34 unique VHs and 28 unique LCs. The comparison results of light chain amino acid sequences were shown in FIG. 5A, and the comparison results of heavy chain variable region amino acid sequences were shown in FIG. 5B.

Example 5 Construction of VH Component Library and LC Component Library 5.1 Amplification of Antigen-Specific VH and Antigen-Specific LC Primers containing the recognition sites for the restriction endonucleases (Esp3I and SfiI) were designed. There were 29 primers for amplifying antigen-specific VH, including 24 forward primers and 5 reverse primers; 19 primers for amplifying antigen-specific KLC (kappa light chain), including 18 forward primers and 1 reverse primer; 26 primers for amplifying antigen-specific LLC (lambda light chain), including 25 forward primers and 1 reverse primer. Each primer in each set of forward primers was mixed in equal proportions, the reverse primers of VH were also mixed in equal proportions, and then the forward and reverse primers were mixed in equal proportions to form three sets of primers, which were used to amplify VH, KLC and LLC respectively. As an exemplary illustration, KLC was taken as an example in this embodiment, wherein, the forward primers of VH were as set forth in SEQ ID NO: 30-53, the reverse primers of VH were as set forth in SEQ ID NO: 54-58, the forward primers of KLC were as set forth in SEQ ID NO: 59-76, and the reverse primer of KLC was as set forth in SEQ ID NO 77.

The mini DNA of 35 positive clones obtained by screening in Example 4 was mixed in equal amounts, and amplified using the three sets of primers described above, respectively. The purified antigen-specific VH and antigen-specific LC (with KLC as an example) with a recognition site obtained by PCR were analyzed by electrophoresis.

5.2 Digestion and Ligation

The antigen-specific VH obtained in Example 5.1 was digested with Esp3I, and the purified antigen-specific VH after digestion was analyzed by electrophoresis. The VH component vector obtained in Example 3.1 was digested with Esp3I, and the purified 2.8 kb of component vector fragment after digestion was analyzed by electrophoresis. The purified antigen-specific VH and 2.8 kb of component vector fragment were ligated to obtain an ROR1-specific VH component library.

The antigen-specific LC obtained in Example 5.1 was digested with SfiI, and the purified antigen-specific LC after digestion was analyzed by electrophoresis. The LC component vector obtained in Example 3.2 was digested with SfiI, and the purified 2.8 kb of component vector fragment after digestion was analyzed by electrophoresis. The purified antigen-specific LC and 2.8 kb of component vector fragment were ligated to obtain an ROR1-specific LC component library.

Example 6 Construction of Antigen-Specific Binding Polypeptide Display Library The VH component library was digested with Esp3I, and the purified 0.35 kb of antigen-specific VH (i.e., the released first polynucleotide) with sticky ends after digestion was analyzed by electrophoresis. The KLC component library was digested with SfiI, and the purified 0.65 kb of antigen-specific LC (i.e., the released second polynucleotide) with sticky ends after digestion was analyzed by electrophoresis. The display vector obtained in Example 1 was double-digested with Esp3I and SfiI, and purified to obtain 3 kb of display vector fragment I (i.e., the released third polynucleotide) with sticky ends and 5 kb of display vector fragment II (i.e., the released fourth polynucleotide) with sticky ends. The above four digested fragments were mixed in equal molecular proportions, and ligated at 20° C. for 4 hours in a ligation system of 10 μl containing a total amount of 25 ng fragments to obtain an antigen-specific binding polypeptide gene display vector.

The ligation product was purified by a PCR Cleanup kit, and collected by eluting with 10 μl ddH$_2$O·4 μl of the purified ligation product was taken for electroporation (Takara DH5a, electroporated competent bacteria), spread on a plate and cultured overnight at 37° C. The colonies were counted, and when the library capacity reached 2.3×10$^5$, an antigen-specific binding polypeptide gene display bacterial library was obtained. All the colonies were collected, from which the vector DNA was extracted to obtain an antigen-specific binding polypeptide display library.

Example 7 Screening of Monoclonal Antibody

Figure 6:
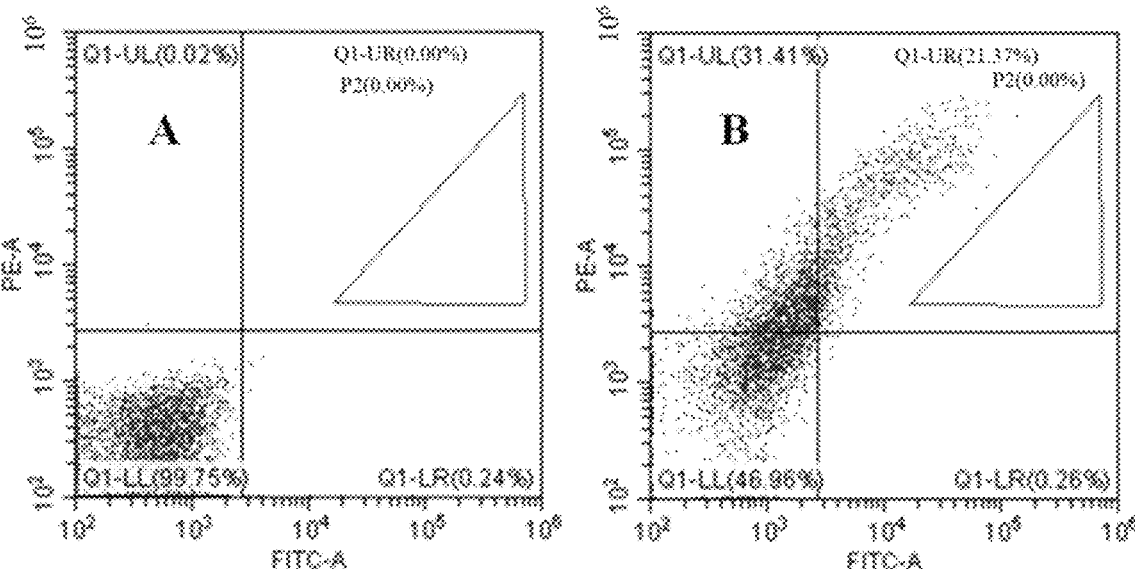
FIG. 6 shows the expression of the ROR1 antigen-specific binding polypeptide on the surface of CHO cells as analyzed by FACS.

ROR1 specific binding polypeptide expression vector DNA was obtained from the antigen-specific binding polypeptide display library obtained in Example 6, and 40 μg of DNA was transformed into FCHO cells. 60 hours after the transformation, the expression of full-length antibodies on the cell surface and the ROR1 antigen-specificity of the antibodies were analyzed by FACS. The results of FIG. 6 showed that there were ROR1 full-length antibodies expressed on the cell surface, and the expressed antibodies could specifically bind to FITC-labeled ROR1 (obtained by labeling with FITC labeling kit). ROR1 antigens without biotin label were from Acro Biosystems (Cat #RO1-H5250-1 mg). FIG. 6 shows the cells double-stained with a PE-labeled mouse anti-human Kappa light chain antibody and an FITC-labeled ROR1 antigen, as well as the fluorescence signals on the cell surface as analyzed by FACS, where A indicates the negative control; B indicates the cell library expressing the ROR1 specific antibody.

A stably transformed FCHO cell library was screened with hygromycin (hygromycin concentration at 500 μg/ml) under pressure. 10 days after culturing with hygromycin under pressure, a stably transformed cell library was obtained. The cell library was double-stained with a PE-labeled mouse anti-human kappa light chain antibody (BD) and an FITC-labeled ROR1 antigen, and PE and FITC double-positive cells were sorted by FACS. Single-cell clones were added to 96-well plates, with one cell per well, and cultured with hygromycin under pressure.

14 days after culturing with hygromycin under pressure, 92 stably transformed single-cell clones were obtained. The cells were digested with 0.5 mM of EDTA-PBS buffer. The 92 single-cell clones were double-stained with a PE-labeled mouse anti-human kappa light chain antibody and an FITC-labeled ROR1 antigen (the antigen concentration was 0.15 ng/50 μl).

By FACS analysis, 71 PE-and-FITC fluorescence double-positive cell clones were obtained, and the positive rate was 77% (71/92=77%).

Example 8 Acquisition of Positive Clone Sequences

According to the location of the positive cell population in the FACS analysis chart, a total of 30 cell clones located in different positions (representing different affinities) were selected for PCR amplification of antibody genes. The cells of positive clones were respectively collected by centrifugation, the supernatant was discarded, and 20 μl of cellular genome extraction solution (Quick Extraction Buffer, Lucigen) was used to extract the cellular genomic DNA according to the reagent instruction. 2 μl of cell genomic DNA extract was taken from each clone, and the VH and LC of each clone were amplified by PCR. The forward primer for amplifying VH fragments was TGGGCTCTGCTCCTCCTGACC (SEQ ID NO: 24), the reverse primer for amplifying VH fragments was AGTTC-CACGACACCGTCACCGGTTC (SEQ ID NO: 25), the forward primer for amplifying LC fragments was GGACCTGGAGGATCCTCTTCTTGG (SEQ ID NO: 26), and the reverse primer for amplifying LC fragments was TAAATTCCTCGGCCGTGCAGGCCTTAT-CAACACTCTCCCCTGTTGAAGCTCT (SEQ ID NO: 27).

The VH and LC fragments amplified by PCR were isolated and purified by electrophoresis. The purified VH and LC fragments were analyzed by sequencing, determining 14 unique VHs and 13 unique LCs, which can be combined to get 17 positive clones with unique sequences (the 6 CDRs of the light and heavy chains differed by at least one amino acid). As an example, the unique sequences of one pair of VH and LC were listed here, where the VH amino acid sequence of the unique sequence was as set forth in SEQ ID NO: 28, and the kappa LC amino acid sequence of the unique sequence was as set forth in SEQ ID NO: 29.

Example 9 Analysis of Antibody Affinity

The positive VH fragments with unique sequences obtained in Example 8 were digested with Esp3I, and the positive LC fragments with unique sequences obtained in Example 8 were digested with SfiI. The digested VH and LC fragments were purified by PCR cleanup. The VH fragments and LC fragments were separately inserted into soluble heavy chain expression vectors, and the colonies were determined by sequencing. The DNA of the VH and LC expression vectors determined by sequencing was extracted.

Figure 7:
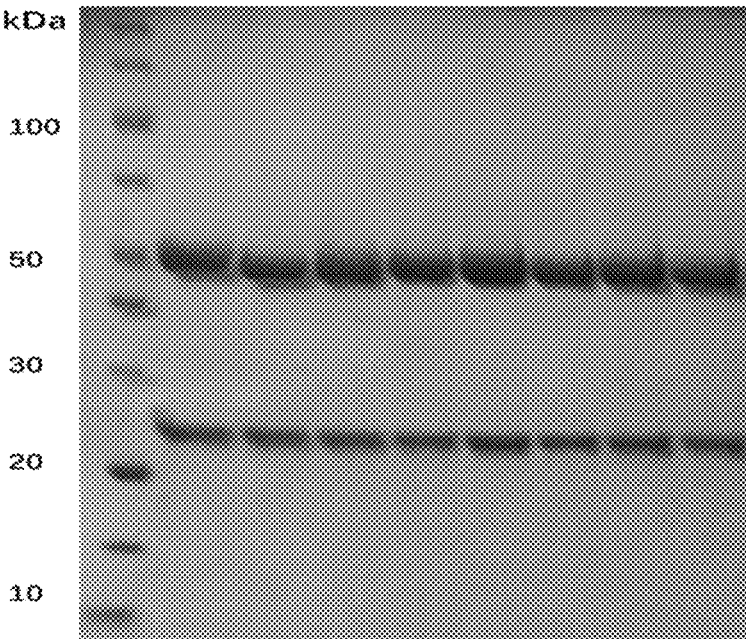
FIG. 7 shows the SDS-PAGE denaturing reduction gel electrophoresis analysis of 8 exemplary antibodies.

293 EXP cells were amplified by suspension culture, and a total of 17 antibody light and heavy chain expression vector pairs were formed according to the light and heavy chain pairing as determined in Example 8. Each pair was mixed at a ratio of 18 μg of the light chain expression vector and 12 μg of the heavy chain expression vector, and used to transform 30 ml of suspended 293EXP cells (1.2×10$^6$/ml). On day 6 of the transformation, the culture supernatant was collected, and the antibody was purified with GenScript's magnetic beads (Cat #L00695) according to the product instructions, equilibrated by dialysis to PBS-antibody solution, and stored at −80° C. Analysis was performed using SDS-PAGE denaturing gel electrophoresis (FIG. 7), with the results showing that the antibody purity reached over 90%. The binding affinity of the purified antibodies to antigens was analyzed by ELISA, and the EC50s of 8 exemplary antibodies were listed here for illustration, with the results shown in Table 4 below.

TABLE 4

Analysis results of the affinity of 8 exemplary antibodies (EC50)

| Antibody No. | EC50 (μg/ml) |
|---|---|
| 1 | 0.531 |
| 11 | 0.161 |
| 32 | 0.207 |
| 101 | 0.102 |
| 103 | 0.177 |
| 115 | 0.225 |
| 140 | 0.159 |
| 162 | 0.229 |

Example 10 Rapid Screening of Antigen-Specific
Polypeptide

Figure 8:
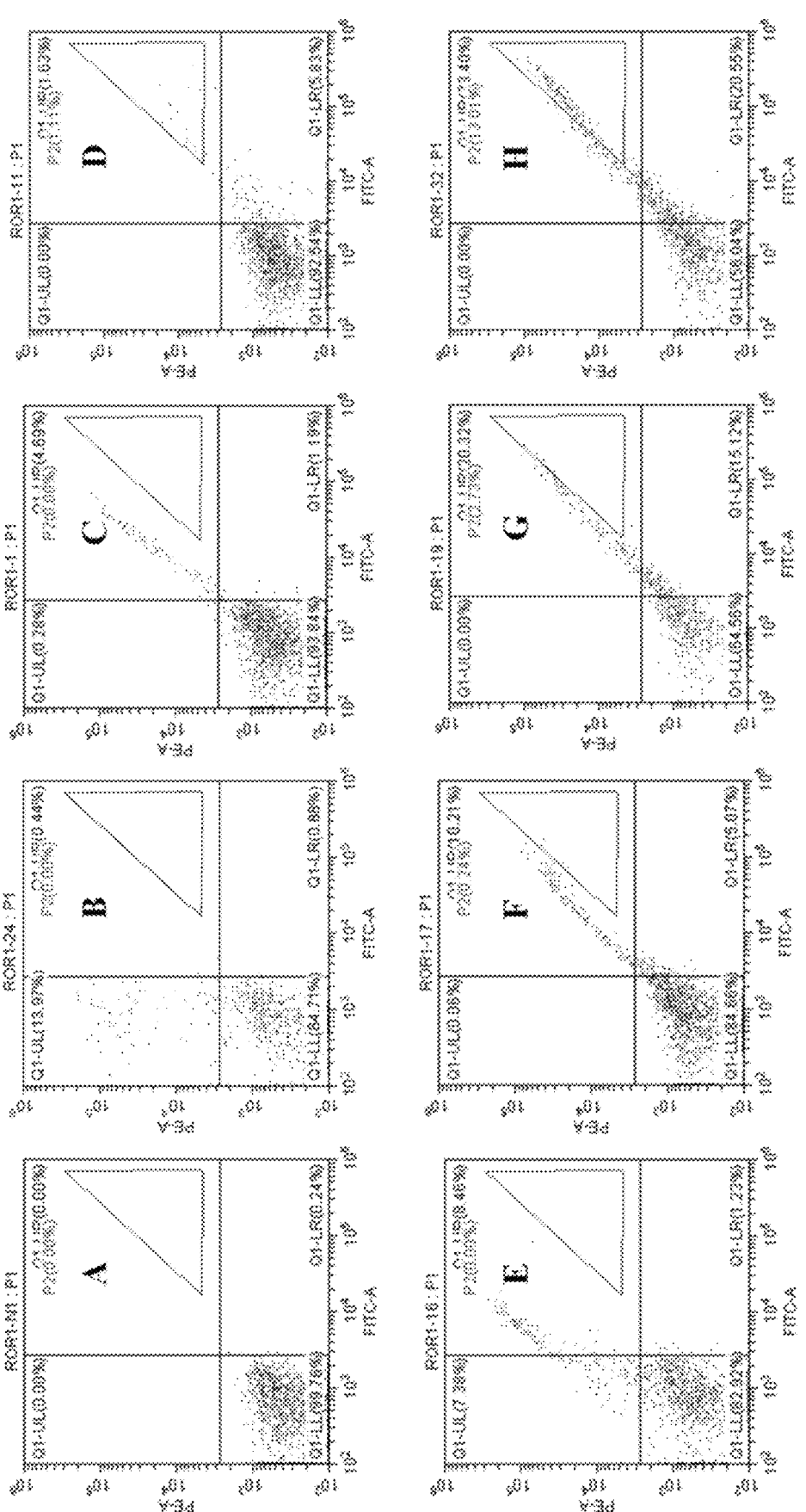
FIG. 8 shows the FACS analysis results of positive antibodies screened by the method of the present application.

According to the ELISA data of positive clones obtained by screening from the phage library in Example 4, 15 clones with ELISA readings of greater than 0.8 were selected from Tables 3-1 and 3-2. After mixing with an equal amount of bacterial liquid, the vector DNA was mini-extracted. According to the procedures in Example 5, the antigen-specific VH and antigen-specific LC of 15 clones were respectively amplified by PCR, and purified by digestion. According to the procedures in Example 6, an antigen-specific binding polypeptide display library was constructed. Then, 48 colonies were randomly sorted and sent for sequencing. After analyzing the sequencing results, 36 clones with correct VH and LC were sorted, from which the vector DNA was mini-extracted and transiently transfected into CHO cells. 60 hours later, the cells were digested with 0.5 mM of EDTA-PBS buffer. 36 cell populations were double-stained with a PE-labeled mouse anti-human kappa light chain antibody and an FITC-labeled ROR1 antigen (the antigen concentration was 0.15 ng/50 l). The FACS analysis results were shown in FIG. 8. Six PE and FITC double-positive cell clones were obtained, and the positive rate was 17% (6/36). FIG. 8 shows the cells double-stained with a PE-labeled mouse anti-human Kappa light chain antibody and an FITC-labeled ROR1 antigen, as well as the fluorescence signals on the cell surface as analyzed by FACS. A indicates the negative control; B indicates the cell clones expressing non-ROR1 specific antibodies; C-H indicates 6 exemplary positive cell clones expressing ROR1 specific antibodies.

What is claimed is:

1. A method for screening an antigen-specific binding polypeptide or fragments thereof, comprising:

a) obtaining the antigen-specific binding VH sequences and the antigen-specific binding LC sequences from a phage display library;

b) constructing the antigen-specific binding polypeptide gene display vectors;

c) introducing the antigen-specific binding polypeptide gene display vectors into the first bacteria to obtain an antigen-specific binding polypeptide gene display bacterial library;

d) acquiring an antigen-specific binding polypeptide gene library from the antigen-specific binding polypeptide gene display bacterial library;

e) acquiring the antigen-specific binding polypeptide gene display vector DNA from the antigen-specific binding polypeptide gene library;

f) introducing the antigen-specific binding polypeptide display vector DNA into cells; optionally wherein the cell is a mammalian cell;

g) acquiring the gene of antigen-specific binding polypeptide from the cell;

wherein constructing the antigen-specific binding polypeptide gene display vectors comprises the following steps:

i. providing the first display vector polynucleotides comprising B2-display VH-B3 in the direction from 5' to 3', inserting the first display vector polynucleotides into the display component vector to form the display VH storage ligation products, and introducing the display VH storage ligation products into the first display bacteria to obtain a display VH component bacterial library, acquiring the display VH component plasmids containing the first display vector polynucleotides from the display VH component bacterial library, and digesting the display VH component plasmids with a restriction endonuclease that specifically recognizes the B2 and B3, thus obtaining the cleaved first display vector polynucleotides;

ii. providing the second display vector polynucleotides comprising S5-display LC-S6 in the direction from 5' to 3', inserting the second display vector polynucleotides into the display component vector to form the display LC storage ligation products, and introducing the display LC storage ligation products into the second display bacteria to obtain a display LC component bacterial library, acquiring the display LC component plasmids containing the second display vector polynucleotides from the display LC component bacterial library, and digesting the display LC component plasmids with a restriction endonuclease that specifically recognizes the S5 and S6, thus obtaining the cleaved second display vector polynucleotides;

iii. providing the third display vector polynucleotides comprising B3-display vector fragment I-S5 in the direction from 5' to 3', cleaving the third display vector polynucleotide with restriction endonucleases that specifically recognizes B3 or S5 to obtain a cleaved third display vector polynucleotide;

iv. providing the fourth display vector polynucleotides comprising S6-display vector fragment II-B2 in the direction from 5' to 3', cleaving the fourth display vector polynucleotide with restriction endonucleases that specifically recognizes S6 or B2 to obtain a cleaved fourth display vector polynucleotide;

v. mixing the cleaved first display vector polynucleotides, the cleaved second display vector polynucleotides, the cleaved third display vector polynucleotides and the cleaved fourth display vector polynucleotides so that they are able to ligate direction ally and cyclized to form the antigen-specific binding polypeptide gene display vectors;

wherein, the display VH encodes a heavy chain variable region of the antigen-specific binding polypeptide, and the display LC encodes the light chain of the antigen-specific binding polypeptide;

wherein the B2 and B3 are able to be specifically recognized and cleaved by an enzyme selected from the group consisting of: BsmBI and Esp3I; and wherein the S5 and S6 are able to be specifically recognized and cleaved by SfiI; and wherein the B2 comprises a nucleic acid sequence as set forth in SEQ ID NO: 8, the B3 comprises a nucleic acid sequence as set forth in SEQ ID NO: 9, the S5 comprises a nucleic acid sequence as set forth in SEQ ID NO: 10, and/or the S6 comprises a nucleic acid sequence as set forth in SEQ ID NO: 11.

2. The method according to claim 1, wherein the display vector component vector is derived from a pUC vector.

3. The method according to claim 1, comprising:

a) providing the fifth polynucleotides each comprising a B-antigen-specific VH-B in the direction from 5' to 3';

b) providing a VH component vector, the VH component vector comprises a sixth polynucleotide comprising B3-VH component vector ligation fragment-B2 in the direction from 5' to 3';

c) cleaving the fifth polynucleotides and the VH component vector with the restriction endonuclease to obtain the cleaved fifth polynucleotides and a released sixth polynucleotide;

d) mixing the cleaved fifth polynucleotides and the released sixth polynucleotide so that they can be ligated directionally and cyclized to form an antigen-specific VH component library;

wherein the B is a recognition site for the restriction endonuclease that can specifically recognize B2 and/or B3, and the antigen-specific VH encodes the heavy chain variable region of the antigen-specific binding polypeptide.

4. The method according to claim 1, comprising:

a) providing the seventh polynucleotides each comprising a S-antigen-specific LC-S in the direction from 5' to 3';

b) providing an LC component vector, the LC component vector comprises an eighth polynucleotide comprising S6-LC component vector ligation fragment-S5 in the direction from 5' to 3';

c) cleaving the seventh polynucleotides and the LC component vector with the restriction endonuclease to obtain the cleaved seventh polynucleotides and a released eighth polynucleotide;

d) mixing the cleaved seventh polynucleotides and the released eighth polynucleotide so that they can be ligated directionally and cyclized to form an antigen-specific LC component library, wherein the S is a recognition site for the restriction endonuclease that can specifically recognize S5 and/or S5, and the antigen-specific LC encodes the light chain of the antigen-specific binding polypeptide.

5. The method according to claim 1, comprising, a) providing a ninth polynucleotide comprising B2-VH component vector tool fragment-B3 in the direction from 5' to 3';

b) inserting the ninth polynucleotide into an expression component vector to obtain the VH component vector.

6. The method according to claim 1, comprising, a) providing a tenth polynucleotide comprising S5-LC component vector tool fragment-S6 in the direction from 5' to 3';

b) inserting the tenth polynucleotide into the expression component vector to obtain the LC component vector.

7. The method according to claim 5, wherein the expression component vector is derived from a pMD vector.

8. The method according to claim 3, comprising the steps of:

introducing the VH component vector into a ninth bacterium to obtain a VH component vector storage bacterial library; acquiring a VH component vector storage plasmid from the VH component vector storage bacterial library; acquiring the released sixth polynucleotide from the VH component vector storage plasmid; and/or introducing the LC component vector into a tenth bacterium to obtain an LC component vector storage bacterial library; acquiring an LC component vector storage plasmid from the LC component vector storage bacterial library; acquiring the released eighth polynucleotide from the LC component vector storage plasmid.

9. The method according to claim 8, comprising digesting the VH component vector storage plasmid with the restriction endonuclease that specifically recognizes the B2 and B3, thus obtaining the released sixth polynucleotide; and/or digesting the LC component vector storage plasmid with the restriction endonuclease that specifically recognizes the S5 and S6, thus obtaining the released eighth polynucleotide.

10. The method according to claim 1, wherein the directional ligation involves using a ligase.

* * * * *